(12) United States Patent
Ekblad et al.

(10) Patent No.: US 10,329,331 B2
(45) Date of Patent: *Jun. 25, 2019

(54) POLYPEPTIDES

(71) Applicant: Affibody AB, Solna (SE)

(72) Inventors: Caroline Ekblad, Saltsjo-Boo (SE); Lars Abrahmsen, Bromma (SE)

(73) Assignee: AFFIBODY AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/955,647

(22) Filed: Dec. 1, 2015

(65) Prior Publication Data

US 2016/0108095 A1    Apr. 21, 2016

Related U.S. Application Data

(63) Continuation of application No. 13/808,713, filed as application No. PCT/EP2011/061623 on Jul. 8, 2011, now Pat. No. 9,211,344.

(60) Provisional application No. 61/403,561, filed on Sep. 17, 2010, provisional application No. 61/399,285, filed on Jul. 9, 2010.

(51) Int. Cl.
| | |
|---|---|
| *C07K 14/315* | (2006.01) |
| *C07K 14/00* | (2006.01) |
| *A61K 51/08* | (2006.01) |
| *A61K 38/00* | (2006.01) |

(52) U.S. Cl.
CPC .......... *C07K 14/315* (2013.01); *A61K 51/081* (2013.01); *C07K 14/001* (2013.01); *A61K 38/00* (2013.01); *C07K 2319/21* (2013.01); *C07K 2319/31* (2013.01); *C07K 2319/50* (2013.01); *C07K 2319/70* (2013.01); *Y02A 50/473* (2018.01)

(58) Field of Classification Search
CPC .............. A61K 38/00; A61K 47/48246; A61K 51/081; C07K 14/001; C07K 14/315; C07K 2319/21; C07K 2319/31; C07K 2319/50; C07K 2319/70
See application file for complete search history.

(56) References Cited

U.S. PATENT DOCUMENTS

| | | | |
|---|---|---|---|
| 6,362,225 B1 | 3/2002 | Andreakos | |
| 7,288,265 B1 | 10/2007 | Rolf | |
| 9,211,344 B2 | 12/2015 | Eckblad et al. | |
| 2003/0017203 A1 | 1/2003 | Crotts et al. | |
| 2004/0001827 A1 | 1/2004 | Dennis | |
| 2005/0215475 A1 | 9/2005 | Ong et al. | |
| 2005/0282756 A1 | 12/2005 | Mehta et al. | |
| 2007/0134279 A1 | 6/2007 | Stern | |
| 2009/0163408 A1 | 6/2009 | Fogelman et al. | |
| 2011/0014247 A1 | 1/2011 | Kidron | |
| 2011/0142800 A1 | 6/2011 | Kidron et al. | |
| 2013/0034597 A1 | 2/2013 | Maggio | |
| 2016/0009767 A9 | 1/2016 | Bejker et al. | |

FOREIGN PATENT DOCUMENTS

| | | |
|---|---|---|
| CN | 101294187 A | 10/2008 |
| WO | 9101743 A1 | 2/1991 |
| WO | 9519374 A1 | 7/1995 |
| WO | 0145746 A2 | 6/2001 |
| WO | 2005087797 A1 | 9/2005 |
| WO | 2008043821 A1 | 4/2008 |
| WO | 2009016043 A2 | 2/2009 |
| WO | 2009080811 A1 | 7/2009 |
| WO | 2010054699 A1 | 5/2010 |
| WO | 2010141329 A1 | 12/2010 |
| WO | 2012016043 A2 | 2/2012 |
| WO | 2012050930 A2 | 4/2012 |
| WO | 2013009539 A1 | 1/2013 |
| WO | 2014048977 A1 | 4/2014 |
| WO | 2015091957 A1 | 6/2015 |

OTHER PUBLICATIONS

International Search Report of the International Searching Authority for International Patent Application No. PCT/EP2013/055441; International Filing Date: Mar. 15, 2013; dated May 16, 2013; 6 Pages.
Written Opinion of the International Searching Authority for International Application No. PCT/EP2013/055441; International Filing Date: Mar. 15, 2013; 4 Pages.
De Chateau, M., "Protein PAB, a Mosaic Albumin-binding Bacterial Protein Representing the First Contemporary Example of Modulue Shuffling", The Journal of Biological Chemistry, Apr. 22, 1994; vol. 269 (16) pp. 12147-12151.
Labouesse "The Hydrolysis of Glucagon by Clostripain" Bulletin de la Societe de Chimie Biologique; 42(11); (1960); pp. 1293-1304. With English Abstract.
Labrou et al., "The Structure-Function Relationship in the Clostripain Family of Peptidases", Eur. J. Biochem. 271; (2004); pp. 983-992.
Mitchell et al., "Purification and Properties of Clostridiopeptidase B (Clostripain)", The Journal of Biological Chemistry; vol. 243; No. 18; (1968); pp. 4683-4692.
Tanaka et al., "High-level Production and Purification of Clostripain Expressed in a Virulence-Attenuated Strain of Clostridium Perfringens", Protein Expression and Purification; 76 (2011); pp. 83-89.
Yanan et al., "An Artificially Evolved Albumin Binding Module Facilitates Chemical Shift Epitope Mapping of GA Domain Interactions with Phylogenetically Diverse Albumins", Protein Science; 16; (2007); pp. 1490-1494.
Goetsch et al. "Identification of B- and T-Cell Epitopes of BB, a Carrier Protein Derived from the G Protein of *Streptococcus* Strain G148" Clinical and Diagnostic Laboratory Immunology; vol. 10, No. 1; Jan. 2003, pp. 125-132.

(Continued)

*Primary Examiner* — Rachael E Bredefeld
*Assistant Examiner* — Erinne R Dabkowski
(74) *Attorney, Agent, or Firm* — Cantor Colburn LLP

(57) ABSTRACT

The present disclosure relates to a class of engineered polypeptides having a binding affinity for albumin. It also relates to new methods and uses that exploit binding by these and other compounds to albumin in different contexts, some of which have significance for treatment or diagnosis of disease in mammals including humans.

60 Claims, 19 Drawing Sheets

Specification includes a Sequence Listing.

(56) References Cited

OTHER PUBLICATIONS

He et al., "An Artifically Evolved Albumin Binding Module Facilitates Chemical Shift Epitope Maping of GA Domain Interactions with Phylogenetically Diverse Albumins" The Protein Society, vol. 16, (2007) pp. 1490-1494.
International Preliminary Report on Patentability and Written Opinion of the International Searching Authority for International Patent Application No. PCT/EP2012/061623; International Filing Date: Jan. 12, 2012; dated Jan. 15, 2013; 5.
International Search Report of the International Searching Authority for International Patent Application No. PCT/EP2012/061623; International Filing Date: Jan. 12, 2012; dated Feb. 6, 2012, 5 Pages.
Jonsson; "Engineering of a femtomolar affinity binding protein to human serum albumin"; Protein Engineering, Design & Selection, vol. 21, No. 8; 2008; pp. 515-527.
Sletten et al.; "Bioorthogonal Chemistry: Fishing for Selectivity in a Sea of Functionality"; Angew Chem Int Ed Engl., 48 (38); 2009; 6974-6998.
Sosabowski et al.; "Conjugation of DOTA-like chelating agents to peptides and radiolabeling with trivalent metallic isotopes"; Nature Protocols, vol. 1,No. 2; 2006; 972-976.
Tanaka et al.; "N-Terminal glycine-specific protein conjugation catalyzed by microbial transglutaminase"; FEBS Letters; 579; 2005; 2092-2096.
The online Medical Dictionary; "Definition of Derivative"; accessed on Jul. 7, 2005; 3 pages.
Aboud-Pirak, E. et al., "Cytotoxic Activity of Daunorubicin or Vindesin Conjugated to a Monoclonal Antibody on Cultured MCF-7 Breast Carconoma Cells", Biochemical Pharmacology, vol. 38, No. 4, (1989) pp. 641-648.
Bauss, F. et al., "Effect of 17B-Estradiol-Bisphosphonate Conjugates, Potential Bone-Seeking Estrogen Pro-Drugs, on 17B-Estradiol Serum Kinetics and Bone Mass in Rats", Calcif Tissue Int (1996) 59, pp. 168-173.
Bonora, G.M. et al., "Antisense activity of an anti-HIV oligonucleotide conjugated to linear and branched high molecular weight polyethylene glycols", II Farmaco 53 (1998), pp. 634-637.
Guo, Neng-Hua et al., "Antiproliferative and antitumor activities of D-reverse peptides derived from the second type-1 repeat of thrombospondin-1", J. Peptide Res. 50, 1997, pp. 210-221.
"Arginine" [online], retrieved from the Internet on Aug. 7, 2017 <URL: http://www.russelllab.org/aas/Arg.html>(three pages) from M.J. Betts, R.B. Russell., Ch. 14. Amino acid properties and consequences of substitutions. In Bioinformatics for Geneticists, M.R. Barnes, I.C. Gray eds, Wiley, 2003.
"Lysine" [online], retrieved from the Internet on Aug. 7, 2017 <URL: http://www.russelllab.org/aas/Lys.html> (two pages) from M.J. Betts, R.B. Russell., Ch. 14. Amino acid properties and consequences of substitutions. In Bioinformatics for Geneticists, M.R. Barnes, I.C. Gray eds, Wiley, 2003.
Langer, M. et al., "Novel Peptide Conjugates for Tumor-Specific Chemotherapy", J. Med. Chem. 2001, 44, pp. 1341-1348.
Qui, Y. et al., "Oestrogen-induced apoptosis in colonocytes expressing oestrogen receptor B", Journal of Endocrinology (2002) 174, pp. 369-377.
Yamamoto, Akira "Improvement of Transmucosal Absorption of Biologically Active Peptide Drugs", published by Yakugaku, Zasshi (Journal of the Pharmaceutical Society of Japan), 2001, vol. 121, No. 12, p. 929-948 (English abstract only).
Parker, Andrew S. et al., "Optimization algorithms for functinal deimmunization of therapeutic proteins", BMC Bioinformatics 2010, 11:180; pp. 1-15.
Frye, C.A., et al., "P-3-BSA, but not P-11-PSA, implants in the VTA rapidly facilitate receptivity in hamsters after progesterone priming to the VMH", Behavioural Brain Research, 53 (1993) pp. 167-175.
Peppas, Nicholas A. et al., Hydrogels for oral delivery of therapeutic proteins, Expert Opin. Biol. Ther., 2004, 4, pp. 1-7.
Strohl, William R., "Fusion Proteins for Half-Life Extension of Biologics as a Strategy to Make Biobetters", BioDrugs (2015) 29 pp. 215-239.

| Polypeptide | Amino acid sequence | SEQ ID NO: |
|---|---|---|
| PP001 | LASAKEAANA ELDAYGVSDF YKRLIDKAKT VEGVEALKDA ILAALP | SEQ ID NO:1 |
| PP002 | LASAKEAANS ELDAYGVSDF YKRLIDKAKT VEGVEALKDA ILAALP | SEQ ID NO:2 |
| PP003 | LASAKESANA ELDAYGVSDF YKRLIDKAKT VEGVEALKDA ILAALP | SEQ ID NO:3 |
| PP004 | LASAKESANS ELDAYGVSDF YKRLIDKAKT VEGVEALKDA ILAALP | SEQ ID NO:4 |
| PP005 | LASAKSAANA ELDAYGVSDF YKRLIDKAKT VEGVEALKDA ILAALP | SEQ ID NO:5 |
| PP006 | LASAKSAANS ELDAYGVSDF YKRLIDKAKT VEGVEALKDA ILAALP | SEQ ID NO:6 |
| PP007 | LASAKSASNA ELDAYGVSDF YKRLIDKAKT VEGVEALKDA ILAALP | SEQ ID NO:7 |
| PP008 | LASAKSASNS ELDAYGVSDF YKRLIDKAKT VEGVEALKDA ILAALP | SEQ ID NO:8 |
| PP009 | LASAKEAANA ELDSYGVSDF YKRLIDKAKT VEGVEALKDA ILAALP | SEQ ID NO:9 |
| PP010 | LASAKEAANS ELDSYGVSDF YKRLIDKAKT VEGVEALKDA ILAALP | SEQ ID NO:10 |
| PP011 | LASAKESANA ELDSYGVSDF YKRLIDKAKT VEGVEALKDA ILAALP | SEQ ID NO:11 |
| PP012 | LASAKESANS ELDSYGVSDF YKRLIDKAKT VEGVEALKDA ILAALP | SEQ ID NO:12 |
| PP013 | LASAKSAANA ELDSYGVSDF YKRLIDKAKT VEGVEALKDA ILAALP | SEQ ID NO:13 |
| PP014 | LASAKSAANS ELDSYGVSDF YKRLIDKAKT VEGVEALKDA ILAALP | SEQ ID NO:14 |
| PP015 | LAEAKEAANA ELDSYGVSDF YKRLIDKAKT VEGVEALKDA ILAALP | SEQ ID NO:15 |
| PP016 | LAEAKEAANS ELDSYGVSDF YKRLIDKAKT VEGVEALKDA ILAALP | SEQ ID NO:16 |
| PP017 | LAEAKESANA ELDSYGVSDF YKRLIDKAKT VEGVEALKDA ILAALP | SEQ ID NO:17 |
| PP018 | LAEAKESANS ELDSYGVSDF YKRLIDKAKT VEGVEALKDA ILAALP | SEQ ID NO:18 |
| PP019 | LAEAKSAANA ELDSYGVSDF YKRLIDKAKT VEGVEALKDA ILAALP | SEQ ID NO:19 |
| PP020 | LAEAKSAANS ELDSYGVSDF YKRLIDKAKT VEGVEALKDA ILAALP | SEQ ID NO:20 |
| PP021 | LAEAKEAANA ELDAYGVSDF YKRLIDKAKT VEGVEALKDA ILAALP | SEQ ID NO:21 |
| PP022 | LAEAKEAANS ELDAYGVSDF YKRLIDKAKT VEGVEALKDA ILAALP | SEQ ID NO:22 |
| PP023 | LAEAKESANA ELDAYGVSDF YKRLIDKAKT VEGVEALKDA ILAALP | SEQ ID NO:23 |
| PP024 | LAEAKESANS ELDAYGVSDF YKRLIDKAKT VEGVEALKDA ILAALP | SEQ ID NO:24 |
| PP025 | LAEAKSAANA ELDAYGVSDF YKRLIDKAKT VEGVEALKDA ILAALP | SEQ ID NO:25 |
| PP026 | LAEAKSAANS ELDAYGVSDF YKRLIDKAKT VEGVEALKDA ILAALP | SEQ ID NO:26 |
| PP027 | LAQAKEAANA ELDAYGVSDF YKRLIDKAKT VEGVEALKDA ILAALP | SEQ ID NO:27 |
| PP028 | LAQAKEAANS ELDAYGVSDF YKRLIDKAKT VEGVEALKDA ILAALP | SEQ ID NO:28 |
| PP029 | LAQAKESANA ELDAYGVSDF YKRLIDKAKT VEGVEALKDA ILAALP | SEQ ID NO:29 |
| PP030 | LAQAKESANS ELDAYGVSDF YKRLIDKAKT VEGVEALKDA ILAALP | SEQ ID NO:30 |
| PP031 | LAQAKSAANA ELDAYGVSDF YKRLIDKAKT VEGVEALKDA ILAALP | SEQ ID NO:31 |
| PP032 | LAQAKSAANS ELDAYGVSDF YKRLIDKAKT VEGVEALKDA ILAALP | SEQ ID NO:32 |
| PP033 | LAQAKEAANA ELDSYGVSDF YKRLIDKAKT VEGVEALKDA ILAALP | SEQ ID NO:33 |
| PP034 | LAQAKESANA ELDSYGVSDF YKRLIDKAKT VEGVEALKDA ILAALP | SEQ ID NO:34 |
| PP035 | LAQAKSAANA ELDSYGVSDF YKRLIDKAKT VEGVEALKDA ILAALP | SEQ ID NO:35 |
| PP036 | LAQAKSAANS ELDSYGVSDF YKRLIDKAKT VEGVEALKDA ILAALP | SEQ ID NO:36 |

Figure 1A

| | | | | | |
|---|---|---|---|---|---|
| PP037 | LASAKEAANA | ELDCYGVSDF | YKRLIDKAKT | VEGVEALKDA | ILAALP | SEQ ID NO:37 |
| PP038 | LASAKEAANS | ELDCYGVSDF | YKRLIDKAKT | VEGVEALKDA | ILAALP | SEQ ID NO:38 |
| PP039 | LASAKESANS | ELDCYGVSDF | YKRLIDKAKT | VEGVEALKDA | ILAALP | SEQ ID NO:39 |
| PP040 | LASAKSAANA | ELDCYGVSDF | YKRLIDKAKT | VEGVEALKDA | ILAALP | SEQ ID NO:40 |
| PP041 | LASAKSAANS | ELDCYGVSDF | YKRLIDKAKT | VEGVEALKDA | ILAALP | SEQ ID NO:41 |
| PP042 | LASAKSESANA | ELDCYGVSDF | YKRLIDKAKT | VEGVEALKDA | ILAALP | SEQ ID NO:42 |
| PP043 | LASAKEAANS | ELDKYGVSDF | YKRLIDKAKT | VEGVEALKDA | ILAALP | SEQ ID NO:43 |
| PP044 | LASAKEAANS | ELDKYGVSDF | YKRLIDKAKT | VEGVEALKDA | ILAALP | SEQ ID NO:44 |
| PP045 | LASAKESANS | ELDKYGVSDF | YKRLIDKAKT | VEGVEALKDA | ILAALP | SEQ ID NO:45 |
| PP046 | LASAKSAANA | ELDKYGVSDF | YKRLIDKAKT | VEGVEALKDA | ILAALP | SEQ ID NO:46 |
| PP047 | LASAKSAANS | ELDKYGVSDF | YKRLIDKAKT | VEGVEALKDA | ILAALP | SEQ ID NO:47 |
| PP048 | LASAKSESANA | ELDKYGVSDF | YKRLIDKAKT | VEGVEALKDA | ILAALP | SEQ ID NO:48 |
| PP049 | LAEAKEAANA | ELDCYGVSDF | YKRLIDKAKT | VEGVEALKDA | ILAALP | SEQ ID NO:49 |
| PP050 | LAEAKEAANS | ELDCYGVSDF | YKRLIDKAKT | VEGVEALKDA | ILAALP | SEQ ID NO:50 |
| PP051 | LAEAKESANS | ELDCYGVSDF | YKRLIDKAKT | VEGVEALKDA | ILAALP | SEQ ID NO:51 |
| PP052 | LAEAKSAANA | ELDCYGVSDF | YKRLIDKAKT | VEGVEALKDA | ILAALP | SEQ ID NO:52 |
| PP053 | LAEAKSAANS | ELDCYGVSDF | YKRLIDKAKT | VEGVEALKDA | ILAALP | SEQ ID NO:53 |
| PP054 | LAEAKSESANA | ELDCYGVSDF | YKRLIDKAKT | VEGVEALKDA | ILAALP | SEQ ID NO:54 |
| PP055 | LAEAKEAANA | ELDKYGVSDF | YKRLIDKAKT | VEGVEALKDA | ILAALP | SEQ ID NO:55 |
| PP056 | LAEAKEAANS | ELDKYGVSDF | YKRLIDKAKT | VEGVEALKDA | ILAALP | SEQ ID NO:56 |
| PP057 | LAEAKESANS | ELDKYGVSDF | YKRLIDKAKT | VEGVEALKDA | ILAALP | SEQ ID NO:57 |
| PP058 | LAEAKSAANA | ELDKYGVSDF | YKRLIDKAKT | VEGVEALKDA | ILAALP | SEQ ID NO:58 |
| PP059 | LAEAKSAANS | ELDKYGVSDF | YKRLIDKAKT | VEGVEALKDA | ILAALP | SEQ ID NO:59 |
| PP060 | LAEAKSESANA | ELDKYGVSDF | YKRLIDKAKT | VEGVEALKDA | ILAALP | SEQ ID NO:60 |
| PP061 | LAQAKEAANA | ELDCYGVSDF | YKRLIDKAKT | VEGVEALKDA | ILAALP | SEQ ID NO:61 |
| PP062 | LAQAKEAANS | ELDCYGVSDF | YKRLIDKAKT | VEGVEALKDA | ILAALP | SEQ ID NO:62 |
| PP063 | LAQAKESANS | ELDCYGVSDF | YKRLIDKAKT | VEGVEALKDA | ILAALP | SEQ ID NO:63 |
| PP064 | LAQAKSAANA | ELDCYGVSDF | YKRLIDKAKT | VEGVEALKDA | ILAALP | SEQ ID NO:64 |
| PP065 | LAQAKSAANS | ELDCYGVSDF | YKRLIDKAKT | VEGVEALKDA | ILAALP | SEQ ID NO:65 |
| PP066 | LAQAKSESANA | ELDCYGVSDF | YKRLIDKAKT | VEGVEALKDA | ILAALP | SEQ ID NO:66 |
| PP067 | LAQAKEAANA | ELDKYGVSDF | YKRLIDKAKT | VEGVEALKDA | ILAALP | SEQ ID NO:67 |
| PP068 | LAQAKEAANS | ELDKYGVSDF | YKRLIDKAKT | VEGVEALKDA | ILAALP | SEQ ID NO:68 |
| PP069 | LAQAKESANS | ELDKYGVSDF | YKRLIDKAKT | VEGVEALKDA | ILAALP | SEQ ID NO:69 |
| PP070 | LAQAKSAANA | ELDKYGVSDF | YKRLIDKAKT | VEGVEALKDA | ILAALP | SEQ ID NO:70 |
| PP071 | LAQAKSAANS | ELDKYGVSDF | YKRLIDKAKT | VEGVEALKDA | ILAALP | SEQ ID NO:71 |
| PP072 | LAQAKSESANA | ELDKYGVSDF | YKRLIDKAKT | VEGVEALKDA | ILAALP | SEQ ID NO:72 |
| PP073 | LACAKEAANA | ELDCYGVSDF | YKRLIDKAKT | VEGVEALKDA | ILAALP | SEQ ID NO:73 |

Figure 1B

| | | | | | |
|---|---|---|---|---|---|
| PP074 | LACAKEAANS | ELDCYGVSDF | YKRLIDKAKT | VEGVEALKDA ILAALP | SEQ ID NO:74 |
| PP075 | LACAKESANS | ELDCYGVSDF | YKRLIDKAKT | VEGVEALKDA ILAALP | SEQ ID NO:75 |
| PP076 | LACAKESANA | ELDCYGVSDF | YKRLIDKAKT | VEGVEALKDA ILAALP | SEQ ID NO:76 |
| PP077 | LACAKSAANA | ELDCYGVSDF | YKRLIDKAKT | VEGVEALKDA ILAALP | SEQ ID NO:77 |
| PP078 | LACAKSAANS | ELDCYGVSDF | YKRLIDKAKT | VEGVEALKDA ILAALP | SEQ ID NO:78 |
| PP079 | LACAKEAANA | ELDKYGVSDF | YKRLIDKAKT | VEGVEALKDA ILAALP | SEQ ID NO:79 |
| PP080 | LACAKEAANS | ELDKYGVSDF | YKRLIDKAKT | VEGVEALKDA ILAALP | SEQ ID NO:80 |
| PP081 | LACAKESANS | ELDKYGVSDF | YKRLIDKAKT | VEGVEALKDA ILAALP | SEQ ID NO:81 |
| PP082 | LACAKESANA | ELDKYGVSDF | YKRLIDKAKT | VEGVEALKDA ILAALP | SEQ ID NO:82 |
| PP083 | LACAKSAANA | ELDKYGVSDF | YKRLIDKAKT | VEGVEALKDA ILAALP | SEQ ID NO:83 |
| PP084 | LACAKSAANS | ELDKYGVSDF | YKRLIDKAKT | VEGVEALKDA ILAALP | SEQ ID NO:84 |
| PP085 | LACAKEAANA | ELDSYGVSDF | YKRLIDKAKT | VEGVEALKDA ILAALP | SEQ ID NO:85 |
| PP086 | LACAKEAANS | ELDSYGVSDF | YKRLIDKAKT | VEGVEALKDA ILAALP | SEQ ID NO:86 |
| PP087 | LACAKESANS | ELDSYGVSDF | YKRLIDKAKT | VEGVEALKDA ILAALP | SEQ ID NO:87 |
| PP088 | LACAKESANA | ELDSYGVSDF | YKRLIDKAKT | VEGVEALKDA ILAALP | SEQ ID NO:88 |
| PP089 | LACAKSAANA | ELDSYGVSDF | YKRLIDKAKT | VEGVEALKDA ILAALP | SEQ ID NO:89 |
| PP090 | LACAKSAANS | ELDSYGVSDF | YKRLIDKAKT | VEGVEALKDA ILAALP | SEQ ID NO:90 |
| PP091 | LACAKEAANA | ELDAYGVSDF | YKRLIDKAKT | VEGVEALKDA ILAALP | SEQ ID NO:91 |
| PP092 | LACAKEAANS | ELDAYGVSDF | YKRLIDKAKT | VEGVEALKDA ILAALP | SEQ ID NO:92 |
| PP093 | LACAKESANS | ELDAYGVSDF | YKRLIDKAKT | VEGVEALKDA ILAALP | SEQ ID NO:93 |
| PP094 | LACAKESANA | ELDAYGVSDF | YKRLIDKAKT | VEGVEALKDA ILAALP | SEQ ID NO:94 |
| PP095 | LACAKSAANA | ELDAYGVSDF | YKRLIDKAKT | VEGVEALKDA ILAALP | SEQ ID NO:95 |
| PP096 | LACAKSAANS | ELDAYGVSDF | YKRLIDKAKT | VEGVEALKDA ILAALP | SEQ ID NO:96 |
| PP097 | LAQAKCAANA | ELDAYGVSDF | YKRLIDKAKT | VEGVEALKDA ILAALP | SEQ ID NO:97 |
| PP098 | LAQAKCAANS | ELDAYGVSDF | YKRLIDKAKT | VEGVEALKDA ILAALP | SEQ ID NO:98 |
| PP099 | LAQAKCSANS | ELDAYGVSDF | YKRLIDKAKT | VEGVEALKDA ILAALP | SEQ ID NO:99 |
| PP100 | LAQAKCSANA | ELDAYGVSDF | YKRLIDKAKT | VEGVEALKDA ILAALP | SEQ ID NO:100 |
| PP101 | LAQAKCAANA | ELDCYGVSDF | YKRLIDKAKT | VEGVEALKDA ILAALP | SEQ ID NO:101 |
| PP102 | LAQAKCAANS | ELDCYGVSDF | YKRLIDKAKT | VEGVEALKDA ILAALP | SEQ ID NO:102 |
| PP103 | LAQAKCAANS | ELDSYGVSDF | YKRLIDKAKT | VEGVEALKDA ILAALP | SEQ ID NO:103 |
| PP104 | LAQAKCAANS | ELDSYGVSDF | YKRLIDKAKT | VEGVEALKDA ILAALP | SEQ ID NO:104 |
| PP105 | LAQAKCSANS | ELDSYGVSDF | YKRLIDKAKT | VEGVEALKDA ILAALP | SEQ ID NO:105 |
| PP106 | LAQAKCSANA | ELDSYGVSDF | YKRLIDKAKT | VEGVEALKDA ILAALP | SEQ ID NO:106 |
| PP107 | LAQAKCAANA | ELDKYGVSDF | YKRLIDKAKT | VEGVEALKDA ILAALP | SEQ ID NO:107 |
| PP108 | LAQAKCAANS | ELDKYGVSDF | YKRLIDKAKT | VEGVEALKDA ILAALP | SEQ ID NO:108 |
| PP109 | LASAKCAANA | ELDAYGVSDF | YKRLIDKAKT | VEGVEALKDA ILAALP | SEQ ID NO:109 |
| PP110 | LASAKCAANS | ELDAYGVSDF | YKRLIDKAKT | VEGVEALKDA ILAALP | SEQ ID NO:110 |

Figure 1C

| | | | | | |
|---|---|---|---|---|---|
| PP111 | LASAKCSANS | ELDAYGVSDF | YKRLIDKAKT | VEGVEALKDA | ILAALP | SEQ ID NO:111 |
| PP112 | LASAKCSANA | ELDAYGVSDF | YKRLIDKAKT | VEGVEALKDA | ILAALP | SEQ ID NO:112 |
| PP113 | LASAKCAANA | ELDCYGVSDF | YKRLIDKAKT | VEGVEALKDA | ILAALP | SEQ ID NO:113 |
| PP114 | LASAKCAANA | ELDCYGVSDF | YKRLIDKAKT | VEGVEALKDA | ILAALP | SEQ ID NO:114 |
| PP115 | LASAKCAANS | ELDSYGVSDF | YKRLIDKAKT | VEGVEALKDA | ILAALP | SEQ ID NO:115 |
| PP116 | LASAKCAANS | ELDSYGVSDF | YKRLIDKAKT | VEGVEALKDA | ILAALP | SEQ ID NO:116 |
| PP117 | LASAKCSANS | ELDSYGVSDF | YKRLIDKAKT | VEGVEALKDA | ILAALP | SEQ ID NO:117 |
| PP118 | LASAKCSANA | ELDSYGVSDF | YKRLIDKAKT | VEGVEALKDA | ILAALP | SEQ ID NO:118 |
| PP119 | LASAKCAANA | ELDKYGVSDF | YKRLIDKAKT | VEGVEALKDA | ILAALP | SEQ ID NO:119 |
| PP120 | LASAKCAANS | ELDKYGVSDF | YKRLIDKAKT | VEGVEALKDA | ILAALP | SEQ ID NO:120 |
| PP121 | LAEAKCAANA | ELDAYGVSDF | YKRLIDKAKT | VEGVEALKDA | ILAALP | SEQ ID NO:121 |
| PP122 | LAEAKCAANS | ELDAYGVSDF | YKRLIDKAKT | VEGVEALKDA | ILAALP | SEQ ID NO:122 |
| PP123 | LAEAKCSANS | ELDAYGVSDF | YKRLIDKAKT | VEGVEALKDA | ILAALP | SEQ ID NO:123 |
| PP124 | LAEAKCAANA | ELDCYGVSDF | YKRLIDKAKT | VEGVEALKDA | ILAALP | SEQ ID NO:124 |
| PP125 | LAEAKCAANA | ELDCYGVSDF | YKRLIDKAKT | VEGVEALKDA | ILAALP | SEQ ID NO:125 |
| PP126 | LAEAKCSANS | ELDCYGVSDF | YKRLIDKAKT | VEGVEALKDA | ILAALP | SEQ ID NO:126 |
| PP127 | LAEAKCAANA | ELDSYGVSDF | YKRLIDKAKT | VEGVEALKDA | ILAALP | SEQ ID NO:127 |
| PP128 | LAEAKCAANS | ELDSYGVSDF | YKRLIDKAKT | VEGVEALKDA | ILAALP | SEQ ID NO:128 |
| PP129 | LAEAKCSANS | ELDSYGVSDF | YKRLIDKAKT | VEGVEALKDA | ILAALP | SEQ ID NO:129 |
| PP130 | LAEAKCSANA | ELDSYGVSDF | YKRLIDKAKT | VEGVEALKDA | ILAALP | SEQ ID NO:130 |
| PP131 | LAEAKCAANA | ELDAYGVSDF | YKRLIDKAKT | VEGVEALKDA | ILAALP | SEQ ID NO:131 |
| PP132 | LAEAKCAANS | ELDAYGVSDF | YKRLIDKAKT | VEGVEALKDA | ILAALP | SEQ ID NO:132 |
| PP133 | LACAKCAANA | ELDCYGVSDF | YKRLIDKAKT | VEGVEALKDA | ILAALP | SEQ ID NO:133 |
| PP134 | LACAKCAANA | ELDCYGVSDF | YKRLIDKAKT | VEGVEALKDA | ILAALP | SEQ ID NO:134 |
| PP135 | LACAKCSANS | ELDSYGVSDF | YKRLIDKAKT | VEGVEALKDA | ILAALP | SEQ ID NO:135 |
| PP136 | LACAKCSANA | ELDAYGVSDF | YKRLIDKAKT | VEGVEALKDA | ILAALP | SEQ ID NO:136 |
| PP137 | LACAKCAANA | ELDCYGVSDF | YKRLIDKAKT | VEGVEALKDA | ILAALP | SEQ ID NO:137 |
| PP138 | LACAKCAANS | ELDSYGVSDF | YKRLIDKAKT | VEGVEALKDA | ILAALP | SEQ ID NO:138 |
| PP139 | LACAKCAANA | ELDKYGVSDF | YKRLIDKAKT | VEGVEALKDA | ILAALP | SEQ ID NO:139 |
| PP140 | LACAKCAANA | ELDSYGVSDF | YKRLIDKAKT | VEGVEALKDA | ILAALP | SEQ ID NO:140 |
| PP141 | LACAKCSANS | ELDSYGVSDF | YKRLIDKAKT | VEGVEALKDA | ILAALP | SEQ ID NO:141 |
| PP142 | LACAKCSANA | ELDAYGVSDF | YKRLIDKAKT | VEGVEALKDA | ILAALP | SEQ ID NO:142 |
| PP143 | LACAKCAANA | ELDCYGVSDF | YKRLIDKAKT | VEGVEALKDA | ILAALP | SEQ ID NO:143 |
| PP144 | LACAKCAANA | ELDKYGVSDF | YKRLIDKAKT | VEGVEALKDA | ILAALP | SEQ ID NO:144 |
| PP145 | GSLASAKEAA | NAELDSYGVS | DFYKRLIDKA | KTVEGVEALK | DAILAALPG | SEQ ID NO:145 |
| PP146 | GSLAEAKEAA | NAELDSYGVS | DFYKRLIDKA | KTVEGVEALK | DAILAALPG | SEQ ID NO:146 |
| PP147 | GSLASAKEAA | NAELDCYGVS | DFYKRLIDKA | KTVEGVEALK | DAILAALPG | SEQ ID NO:147 |

Figure 1D

| | | | | |
|---|---|---|---|---|
| PEP08185 | GSLAEAKEAA NAELDCYGVS DFYKRLIDKA KTVEGVEALK DAILAALPG | SEQ ID NO:148 |
| PP149 | GSLASAKEAA NAELDSYGVS DFYKRLIDKA KTVEGVEALK DAILAALPCG | SEQ ID NO:149 |
| PP150 | GSLAEAKEAA NAELDSYGVS DFYKRLIDKA KTVEGVEALK DAILAALPCG | SEQ ID NO:150 |
| PP151 | GCSLASAKEA ANAELDKYGV SDFYKRLIDK AKTVEGVEAL KDAILAALPG | SEQ ID NO:151 |
| PP152 | GCSLAEAKEA ANAELDKYGV SDFYKRLIDK AKTVEGVEAL KDAILAALPG | SEQ ID NO:152 |
| PEP07913 | GLAEAKVLAN RELDKYGVSD YYKNLINNAK TVEGVKALID EILAALP | SEQ ID NO:153 |
| PEP06923 | GSSLAEAKVL ANRELDKYGV SDFYKRLINK AKTVEGVEAL KLHILAALP | SEQ ID NO:154 |
| PEP07271 | GSSLASAKEA ANAELDAYGV SDFYKRLIDK AKTVEGVEAL KDAILAALP | SEQ ID NO:155 |
| PEP07554 | GSSLASAKEA ANAELDSYGV SDFYKRLIDK AKTVEGVEAL KDAILAALP | SEQ ID NO:156 |
| PEP07912 | GLASAKEAAN AELDSYGVSD FYKRLIDKAK TVEGVEALKD AILAALP | SEQ ID NO:157 |
| PEP07914 | GLAEAKEAAN AELDSYGVSD FYKRLIDKAK TVEGVEALKD AILAALP | SEQ ID NO:158 |
| PEP07911 | GLASAKEAAN AELDCYGVSD FYKRLIDKAK TVEGVEALKD AILAALP | SEQ ID NO:159 |
| PEP07834 | ALASAKEAAN AELDCYGVSD FYKRLIDKAK TVEGVEALKD AILAALP | SEQ ID NO:160 |
| PEP07844 | GSSLASAKEA ANAELDKYGV SDFYKRLIDK AKTVEGVEALK KDAILAALP | SEQ ID NO:161 |
| PEP07983 | GSSLASAKEA NAELDSYGVS DFYKRLIDKA KTVEGVEALK DAILAALP | SEQ ID NO:162 |
| PEP07986 | GSLAEAKEAA NAELDSYGVS DFYKRLIDKA KTVEGVEALK DAILAALP | SEQ ID NO:163 |
| PP164 | LAEAKEAANR ELDSYGVSDF YKRLIDKAKT VEGVEALKDA ILAALP | SEQ ID NO:164 |
| PP165 | LAEAKEAANA ELDSYGVSDF YKRLIEKAKT VEGVEALKDA ILAALP | SEQ ID NO:165 |
| PP166 | LAEAKEAANA ELDSYGVSDF YKRLIDKAKT VEGVEALKEA ILAALP | SEQ ID NO:166 |
| PP167 | LAEAKEAANR ELDSYGVSDF YKRLIEKAKT VEGVEALKEA ILAALP | SEQ ID NO:167 |
| PP168 | LAEAKEAANA ELDSYGVSDF YKRLIDKAKT VEGVEALKDA ILKALP | SEQ ID NO:168 |
| PP169 | LAEAKEAANR ELDSYGVSDF YKRLIDKAKT VEGVEALKDA ILKALP | SEQ ID NO:169 |
| PP170 | LAEAKEAANA ELDSYGVSDF YKRLIDKAKT VEGVEALKDA ILASLP | SEQ ID NO:170 |
| PP171 | LAEAKEAANR ELDSYGVSDF YKRLIDKAKT VEGVEALKDA ILAALP | SEQ ID NO:171 |
| PP172 | LAEAKEAANA ELDAYGVSDF YKRLIEKAKT VEGVEALKEA ILAALP | SEQ ID NO:172 |
| PP173 | LAEAKEAANR ELDAYGVSDF YKRLIDKAKT VEGVEALKEA ILAALP | SEQ ID NO:173 |
| PP174 | LAEAKEAANA ELDAYGVSDF YKRLIEKAKT VEGVEALKEA ILAALP | SEQ ID NO:174 |
| PP175 | LAEAKEAANR ELDAYGVSDF YKRLIEKAKT VEGVEALKEA ILAALP | SEQ ID NO:175 |
| PP176 | LAEAKEAANA ELDAYGVSDF YKRLIDKAKT VEGVEALKDA ILKALP | SEQ ID NO:176 |
| PP177 | LAEAKEAANA ELDAYGVSDF YKRLIDKAKT VEGVEALKDA ILASLP | SEQ ID NO:177 |
| PP178 | LAQAKEAANA ELDAYGVSDF YKRLIDKAKT VEGVEALKDA ILAALP | SEQ ID NO:178 |
| PP179 | LAQAKEAANR ELDAYGVSDF YKRLIEKAKT VEGVEALKDA ILAALP | SEQ ID NO:179 |
| PP180 | LAQAKEAANA ELDAYGVSDF YKRLIDKAKT VEGVEALKEA ILAALP | SEQ ID NO:180 |
| PP181 | LAQAKEAANR ELDAYGVSDF YKRLIEKAKT VEGVEALKEA ILAALP | SEQ ID NO:181 |
| PP182 | LAQAKEAANA ELDAYGVSDF YKRLIDKAKT VEGVEALKDA ILKALP | SEQ ID NO:182 |
| PP183 | LAQAKEAANR ELDAYGVSDF YKRLIDKAKT VEGVEALKDA ILKALP | SEQ ID NO:183 |
| PP184 | LAQAKEAANA ELDAYGVSDF YKRLIDKAKT VEGVEALKDA ILASLP | SEQ ID NO:184 |

Figure 1E

| | | | | | |
|---|---|---|---|---|---|
| PP185 | LAQAKEAANR | ELDSYGVSDF | YKRLIDKAKT | VEGVEALKDA | ILAALP | SEQ ID NO:185 |
| PP186 | LAQAKEAANA | ELDSYGVSDF | YKRLIEKAKT | VEGVEALKDA | ILAALP | SEQ ID NO:186 |
| PP187 | LAQAKEAANA | ELDSYGVSDF | YKRLIDKAKT | VEGVEALKEA | ILAALP | SEQ ID NO:187 |
| PP188 | LAQAKEAANA | ELDSYGVSDF | YKRLIEKAKT | VEGVEALKEA | ILAALP | SEQ ID NO:188 |
| PP189 | LAQAKEAANR | ELDSYGVSDF | YKRLIEKAKT | VEGVEALKEA | ILAALP | SEQ ID NO:189 |
| PP190 | LAQAKEAANA | ELDSYGVSDF | YKRLIDKAKT | VEGVEALKDA | ILKALP | SEQ ID NO:190 |
| PP191 | LAQAKEAANA | ELDSYGVSDF | YKRLIDKAKT | VEGVEALKDA | ILASLP | SEQ ID NO:191 |
| PP192 | LAEAKEAANR | ELDCYGVSDF | YKRLIEKAKT | VEGVEALKDA | ILAALP | SEQ ID NO:192 |
| PP193 | LAEAKEAANA | ELDCYGVSDF | YKRLIDKAKT | VEGVEALKEA | ILAALP | SEQ ID NO:193 |
| PP194 | LAEAKEAANA | ELDCYGVSDF | YKRLIEKAKT | VEGVEALKEA | ILAALP | SEQ ID NO:194 |
| PP195 | LAEAKEAANA | ELDCYGVSDF | YKRLIEKAKT | VEGVEALKEA | ILAALP | SEQ ID NO:195 |
| PP196 | LAEAKEAANR | ELDCYGVSDF | YKRLIEKAKT | VEGVEALKEA | ILAALP | SEQ ID NO:196 |
| PP197 | LAEAKEAANA | ELDCYGVSDF | YKRLIEKAKT | VEGVEALKDA | ILKALP | SEQ ID NO:197 |
| PP198 | LAEAKEAANA | ELDCYGVSDF | YKRLIDKAKT | VEGVEALKDA | IIASLP | SEQ ID NO:198 |
| PP199 | LAEAKEAANA | ELDSYGVSDF | YKRLIDKAKT | VEGVEALKDA | ILAAL | SEQ ID NO:199 |
| PP200 | LAEAKEAANR | ELDAYGVSDF | YKRLIDKAKT | VEGVEALKDA | ILAAL | SEQ ID NO:200 |
| PP201 | LAQAKEAANA | ELDSYGVSDF | YKRLIDKAKT | VEGVEALKDA | ILAAL | SEQ ID NO:201 |
| PP202 | LAQAKEAAAA | ELDCYGVSDF | YKRLIDKAKT | VEGVEALKDA | ILAAL | SEQ ID NO:202 |
| PP203 | LAEAKEAANA | ELDCYGVSDF | YKRLIDKAKT | VEGVEALKDA | ILAAL | SEQ ID NO:203 |

Figure 1F

SEQUENCE LISTING

```
<160> NUMBER OF SEQ ID NOS: 212

<210> SEQ ID NO 1
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 1

Leu Ala Ser Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 2
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 2

Leu Ala Ser Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 3
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 3

Leu Ala Ser Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 4
<211> LENGTH: 46
<212> TYPE: PRT
<213> ORGANISM: Artificial
<220> FEATURE:
```

<223> OTHER INFORMATION: Engineered albumin-binding polypeptide

<400> SEQUENCE: 4

Leu Ala Ser Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 5
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 5

Leu Ala Ser Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 6
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 6

Leu Ala Ser Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 7
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 7

Leu Ala Ser Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 8
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 8

```
Leu Ala Ser Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 9
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 9

```
Leu Ala Ser Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 10
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 10

```
Leu Ala Ser Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 11
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 11

```
Leu Ala Ser Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 12
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 12

```
Leu Ala Ser Ala Lys Ser Ala Ala Asn Ser Glu Leu Asp Ser Tyr Gly
1               5                   10                  15
```

```
Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 13
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 13

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 14
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 14

Leu Ala Glu Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 15
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 15

Leu Ala Glu Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 16
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 16

Leu Ala Glu Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30
```

-continued

```
Gly Val Glu Ala Leu Lys Asp Ala Ile Leu Ala Ala Leu Pro
        35                  40                  45

<210> SEQ ID NO 17
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 17

Leu Ala Glu Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 18
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 18

Leu Ala Glu Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 19
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 19

Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 20
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 20

Leu Ala Glu Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

```
<210> SEQ ID NO 21
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 21

Leu Ala Glu Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 22
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 22

Leu Ala Glu Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 23
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 23

Leu Ala Glu Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 24
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 24

Leu Ala Glu Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 25
```

```
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 25

Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 26
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 26

Leu Ala Gln Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 27
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 27

Leu Ala Gln Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 28
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 28

Leu Ala Gln Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 29
<211> LENGTH: 46
<212> TYPE: PRT
<213> ORGANISM: Artificial
```

<220> FEATURE:
<223> OTHER INFORMATION: Engineered albumin-binding polypeptide

<400> SEQUENCE: 29

Leu Ala Gln Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 30
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 30

Leu Ala Gln Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 31
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 31

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 32
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 32

Leu Ala Gln Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 33
<211> LENGTH: 46
<212> TYPE: PRT
<213> ORGANISM: Artificial
<220> FEATURE:
<223> OTHER INFORMATION: Engineered albumin-binding polypeptide -continued

<400> SEQUENCE: 33

Leu Ala Gln Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 34
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 34

Leu Ala Gln Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 35
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 35

Leu Ala Gln Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 36
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 36

Leu Ala Gln Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 37
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 37

Leu Ala Ser Ala Lys Glu Ala Ala Asn Ala Glu Leu Asp Cys Tyr Gly

```
1               5                  10                 15
Val Ser Asp Phe Tyr Lys Arg Leu Ile Asp Lys Ala Lys Thr Val Glu
            20                 25                 30

Gly Val Glu Ala Leu Lys Asp Ala Ile Leu Ala Ala Leu Pro
        35                 40                 45

<210> SEQ ID NO 38
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 38

Leu Ala Ser Ala Lys Glu Ala Ala Asn Ser Glu Leu Asp Cys Tyr Gly
1               5                  10                 15

Val Ser Asp Phe Tyr Lys Arg Leu Ile Asp Lys Ala Lys Thr Val Glu
            20                 25                 30

Gly Val Glu Ala Leu Lys Asp Ala Ile Leu Ala Ala Leu Pro
        35                 40                 45

<210> SEQ ID NO 39
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 39

Leu Ala Ser Ala Lys Glu Ser Ala Asn Ser Glu Leu Asp Cys Tyr Gly
1               5                  10                 15

Val Ser Asp Phe Tyr Lys Arg Leu Ile Asp Lys Ala Lys Thr Val Glu
            20                 25                 30

Gly Val Glu Ala Leu Lys Asp Ala Ile Leu Ala Ala Leu Pro
        35                 40                 45

<210> SEQ ID NO 40
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 40

Leu Ala Ser Ala Lys Glu Ser Ala Asn Ala Glu Leu Asp Cys Tyr Gly
1               5                  10                 15

Val Ser Asp Phe Tyr Lys Arg Leu Ile Asp Lys Ala Lys Thr Val Glu
            20                 25                 30

Gly Val Glu Ala Leu Lys Asp Ala Ile Leu Ala Ala Leu Pro
        35                 40                 45

<210> SEQ ID NO 41
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 41

Leu Ala Ser Ala Lys Ser Ala Ala Asn Ala Glu Leu Asp Cys Tyr Gly
1               5                  10                 15

Val Ser Asp Phe Tyr Lys Arg Leu Ile Asp Lys Ala Lys Thr Val Glu
```

```
                    20                  25                  30

Gly Val Glu Ala Leu Lys Asp Ala Ile Leu Ala Ala Leu Pro
            35                  40                  45

<210> SEQ ID NO 42
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 42

Leu Ala Ser Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 43
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 43

Leu Ala Ser Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 44
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 44

Leu Ala Ser Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 45
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 45

Leu Ala Ser Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
```

```
                35                  40                  45
```

<210> SEQ ID NO 46
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 46

```
Leu Ala Ser Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 47
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 47

```
Leu Ala Ser Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 48
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 48

```
Leu Ala Ser Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 49
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 49

```
Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

-continued

<210> SEQ ID NO 50
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 50

Leu Ala Glu Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 51
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 51

Leu Ala Glu Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 52
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 52

Leu Ala Glu Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 53
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 53

Leu Ala Glu Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 54
<211> LENGTH: 46
<212> TYPE: PRT

<213> ORGANISM: Artificial
<220> FEATURE:
<223> OTHER INFORMATION: Engineered albumin-binding polypeptide

<400> SEQUENCE: 54

```
Leu Ala Glu Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 55
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 55

```
Leu Ala Glu Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 56
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 56

```
Leu Ala Glu Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 57
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 57

```
Leu Ala Glu Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 58
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 58

Leu Ala Glu Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 59
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 59

Leu Ala Glu Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 60
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 60

Leu Ala Glu Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 61
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 61

Leu Ala Gln Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 62
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 62

Leu Ala Gln Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 63
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 63

Leu Ala Gln Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 64
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 64

Leu Ala Gln Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 65
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 65

Leu Ala Gln Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 66
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 66

Leu Ala Gln Ala Lys Ser Ala Ala Asn Ser Glu Leu Asp Cys Tyr Gly
1               5                   10                  15

```
Val Ser Asp Phe Tyr Lys Arg Leu Ile Asp Lys Ala Lys Thr Val Glu
             20                  25                  30

Gly Val Glu Ala Leu Lys Asp Ala Ile Leu Ala Ala Leu Pro
         35                  40                  45

<210> SEQ ID NO 67
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 67

Leu Ala Gln Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
             20                  25                  30

Gly Val Glu Ala Leu Lys Asp Ala Ile Leu Ala Ala Leu Pro
         35                  40                  45

<210> SEQ ID NO 68
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 68

Leu Ala Gln Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
             20                  25                  30

Gly Val Glu Ala Leu Lys Asp Ala Ile Leu Ala Ala Leu Pro
         35                  40                  45

<210> SEQ ID NO 69
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 69

Leu Ala Gln Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
             20                  25                  30

Gly Val Glu Ala Leu Lys Asp Ala Ile Leu Ala Ala Leu Pro
         35                  40                  45

<210> SEQ ID NO 70
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 70

Leu Ala Gln Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
             20                  25                  30
```

Gly Val Glu Ala Leu Lys Asp Ala Ile Leu Ala Ala Leu Pro
            35                  40                  45

<210> SEQ ID NO 71
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 71

Leu Ala Gln Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 72
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 72

Leu Ala Gln Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 73
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 73

Leu Ala Cys Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 74
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 74

Leu Ala Cys Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 75
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 75

Leu Ala Cys Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 76
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 76

Leu Ala Cys Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 77
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 77

Leu Ala Cys Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 78
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 78

Leu Ala Cys Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 79
<211> LENGTH: 46

```
<212> TYPE: PRT
<213> ORGANISM: Artificial
<220> FEATURE:
<223> OTHER INFORMATION: Engineered albumin-binding polypeptide

<400> SEQUENCE: 79

Leu Ala Cys Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 80
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 80

Leu Ala Cys Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 81
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 81

Leu Ala Cys Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 82
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 82

Leu Ala Cys Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 83
<211> LENGTH: 46
<212> TYPE: PRT
<213> ORGANISM: Artificial
<220> FEATURE:
```

<223> OTHER INFORMATION: Engineered albumin-binding polypeptide

<400> SEQUENCE: 83

Leu Ala Cys Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 84
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 84

Leu Ala Cys Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 85
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 85

Leu Ala Cys Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 86
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 86

Leu Ala Cys Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 87
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 87

```
Leu Ala Cys Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 88
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 88

```
Leu Ala Cys Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 89
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 89

```
Leu Ala Cys Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 90
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 90

```
Leu Ala Cys Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 91
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 91

```
Leu Ala Cys Ala Lys Glu Ala Ala Asn Ala Glu Leu Asp Ala Tyr Gly
1               5                   10                  15
```

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 92
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 92

Leu Ala Cys Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 93
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 93

Leu Ala Cys Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 94
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 94

Leu Ala Cys Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 95
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 95

Leu Ala Cys Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

-continued

Gly Val Glu Ala Leu Lys Asp Ala Ile Leu Ala Ala Leu Pro
        35                  40                  45

<210> SEQ ID NO 96
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 96

Leu Ala Cys Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 97
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 97

Leu Ala Gln Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 98
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 98

Leu Ala Gln Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 99
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 99

Leu Ala Gln Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 100
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 100

Leu Ala Gln Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 101
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 101

Leu Ala Gln Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 102
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 102

Leu Ala Gln Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 103
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 103

Leu Ala Gln Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 104

```
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 104

Leu Ala Gln Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 105
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 105

Leu Ala Gln Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 106
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 106

Leu Ala Gln Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 107
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 107

Leu Ala Gln Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 108
<211> LENGTH: 46
<212> TYPE: PRT
<213> ORGANISM: Artificial
```

<220> FEATURE:
<223> OTHER INFORMATION: Engineered albumin-binding polypeptide

<400> SEQUENCE: 108

Leu Ala Gln Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 109
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 109

Leu Ala Ser Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 110
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 110

Leu Ala Ser Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 111
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 111

Leu Ala Ser Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 112
<211> LENGTH: 46
<212> TYPE: PRT
<213> ORGANISM: Artificial
<220> FEATURE:
<223> OTHER INFORMATION: Engineered albumin-binding polypeptide -continued

```
<400> SEQUENCE: 112

Leu Ala Ser Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 113
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 113

Leu Ala Ser Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 114
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 114

Leu Ala Ser Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 115
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 115

Leu Ala Ser Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 116
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 116

Leu Ala Ser Ala Lys Cys Ala Ala Asn Ser Glu Leu Asp Ser Tyr Gly
```

```
1               5                  10                 15
Val Ser Asp Phe Tyr Lys Arg Leu Ile Asp Lys Ala Lys Thr Val Glu
            20                 25                 30

Gly Val Glu Ala Leu Lys Asp Ala Ile Leu Ala Ala Leu Pro
            35                 40             45

<210> SEQ ID NO 117
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 117

Leu Ala Ser Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40              45

<210> SEQ ID NO 118
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 118

Leu Ala Ser Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40              45

<210> SEQ ID NO 119
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 119

Leu Ala Ser Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40              45

<210> SEQ ID NO 120
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 120

Leu Ala Ser Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
```

```
                20                  25                  30

Gly Val Glu Ala Leu Lys Asp Ala Ile Leu Ala Ala Leu Pro
        35                  40                  45

<210> SEQ ID NO 121
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 121

Leu Ala Glu Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 122
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 122

Leu Ala Glu Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 123
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 123

Leu Ala Glu Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 124
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 124

Leu Ala Glu Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
```

35                  40                  45

<210> SEQ ID NO 125
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 125

Leu Ala Glu Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 126
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 126

Leu Ala Glu Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 127
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 127

Leu Ala Glu Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 128
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 128

Leu Ala Glu Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 129
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 129

Leu Ala Glu Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 130
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 130

Leu Ala Glu Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 131
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 131

Leu Ala Glu Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 132
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 132

Leu Ala Glu Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 133
<211> LENGTH: 46
<212> TYPE: PRT

<213> ORGANISM: Artificial
<220> FEATURE:
<223> OTHER INFORMATION: Engineered albumin-binding polypeptide

<400> SEQUENCE: 133

Leu Ala Cys Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 134
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 134

Leu Ala Cys Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 135
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 135

Leu Ala Cys Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 136
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 136

Leu Ala Cys Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 137
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 137

Leu Ala Cys Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 138
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 138

Leu Ala Cys Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 139
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 139

Leu Ala Cys Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 140
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 140

Leu Ala Cys Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 141
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 141

```
Leu Ala Cys Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 142
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 142

```
Leu Ala Cys Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 143
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 143

```
Leu Ala Cys Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 144
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 144

```
Leu Ala Cys Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 145
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 145

```
Gly Ser Leu Ala Ser Ala Lys Glu Ala Ala Asn Ala Glu Leu Asp Ser
1               5                   10                  15
```

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 146
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 146

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 147
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 147

Gly Ser Leu Ala Ser Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 148
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 148

Gly Ser Leu Ala Glu Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 149
<211> LENGTH: 50
<212> TYPE: PRT
<213> ORGANISM: Artificial
<220> FEATURE:
<223> OTHER INFORMATION: Engineered albumin-binding polypeptide

```
<400> SEQUENCE: 149

Gly Ser Leu Ala Ser Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Cys Gly
    50

<210> SEQ ID NO 150
<211> LENGTH: 50
<212> TYPE: PRT
<213> ORGANISM: Artificial
<220> FEATURE:
<223> OTHER INFORMATION: Engineered albumin-binding polypeptide

<400> SEQUENCE: 150

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Cys Gly
    50

<210> SEQ ID NO 151
<211> LENGTH: 50
<212> TYPE: PRT
<213> ORGANISM: Artificial
<220> FEATURE:
<223> OTHER INFORMATION: Engineered albumin-binding polypeptide

<400> SEQUENCE: 151

Gly Cys Ser Leu Ala Ser Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro Gly
    50

<210> SEQ ID NO 152
<211> LENGTH: 50
<212> TYPE: PRT
<213> ORGANISM: Artificial
<220> FEATURE:
<223> OTHER INFORMATION: Engineered albumin-binding polypeptide

<400> SEQUENCE: 152

Gly Cys Ser Leu Ala Glu Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro Gly
    50
```

-continued

```
<210> SEQ ID NO 153
<211> LENGTH: 47
<212> TYPE: PRT
<213> ORGANISM: Artificial
<220> FEATURE:
<223> OTHER INFORMATION: Engineered albumin-binding polypeptide

<400> SEQUENCE: 153

Gly Leu Ala Glu Ala Lys Val Leu Ala Asn Arg Glu Leu Asp Lys Tyr
1               5                   10                  15

Gly Val Ser Asp Tyr Tyr Lys Asn Leu Ile Asn Asn Ala Lys Thr Val
            20                  25                  30

Glu Gly Val Lys Ala Leu Ile Asp Glu Ile Leu Ala Ala Leu Pro
        35                  40                  45

<210> SEQ ID NO 154
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 154

Gly Ser Ser Leu Ala Glu Ala Lys Val Leu Ala Asn Arg Glu Leu Asp
1               5                   10                  15

Lys Tyr Gly Val Ser Asp Phe Tyr Lys Arg Leu Ile Asn Lys Ala Lys
            20                  25                  30

Thr Val Glu Gly Val Glu Ala Leu Lys Leu His Ile Leu Ala Ala Leu
        35                  40                  45

Pro

<210> SEQ ID NO 155
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 155

Gly Ser Ser Leu Ala Ser Ala Lys Glu Ala Ala Asn Ala Glu Leu Asp
1               5                   10                  15

Ala Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 156
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 156

Gly Ser Ser Leu Ala Ser Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
```

35               40               45

Pro

<210> SEQ ID NO 157
<211> LENGTH: 47
<212> TYPE: PRT
<213> ORGANISM: Artificial
<220> FEATURE:
<223> OTHER INFORMATION: Engineered albumin-binding polypeptide

<400> SEQUENCE: 157

Gly Leu Ala Ser Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 158
<211> LENGTH: 47
<212> TYPE: PRT
<213> ORGANISM: Artificial
<220> FEATURE:
<223> OTHER INFORMATION: Engineered albumin-binding polypeptide

<400> SEQUENCE: 158

Gly Leu Ala Glu Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 159
<211> LENGTH: 47
<212> TYPE: PRT
<213> ORGANISM: Artificial
<220> FEATURE:
<223> OTHER INFORMATION: Engineered albumin-binding polypeptide

<400> SEQUENCE: 159

Gly Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 160
<211> LENGTH: 47
<212> TYPE: PRT
<213> ORGANISM: Artificial
<220> FEATURE:
<223> OTHER INFORMATION: Engineered albumin-binding polypeptide

<400> SEQUENCE: 160

Ala Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 161
<211> LENGTH: 49
<212> TYPE: PRT
<213> ORGANISM: Artificial
<220> FEATURE:
<223> OTHER INFORMATION: Engineered albumin-binding polypeptide

<400> SEQUENCE: 161

Gly Ser Ser Leu Ala Ser Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala Leu
            35                  40                  45

Pro

<210> SEQ ID NO 162
<211> LENGTH: 48
<212> TYPE: PRT
<213> ORGANISM: Artificial
<220> FEATURE:
<223> OTHER INFORMATION: Engineered albumin-binding polypeptide

<400> SEQUENCE: 162

Gly Ser Leu Ala Ser Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu Pro
            35                  40                  45

<210> SEQ ID NO 163
<211> LENGTH: 48
<212> TYPE: PRT
<213> ORGANISM: Artificial
<220> FEATURE:
<223> OTHER INFORMATION: Engineered albumin-binding polypeptide

<400> SEQUENCE: 163

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu Pro
            35                  40                  45

<210> SEQ ID NO 164
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 164

Leu Ala Glu Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 165
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 165

Leu Ala Glu Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 166
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 166

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 167
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 167

Leu Ala Glu Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 168
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 168

Leu Ala Glu Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 169
<211> LENGTH: 46

```
<212> TYPE: PRT
<213> ORGANISM: Artificial
<220> FEATURE:
<223> OTHER INFORMATION: Engineered albumin-binding polypeptide

<400> SEQUENCE: 169

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 170
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 170

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45

<210> SEQ ID NO 171
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 171

Leu Ala Glu Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 172
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 172

Leu Ala Glu Ala Lys Glu Ala Ala Asn Ala Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 173
<211> LENGTH: 46
<212> TYPE: PRT
<213> ORGANISM: Artificial
<220> FEATURE:
```

<223> OTHER INFORMATION: Engineered albumin-binding polypeptide

<400> SEQUENCE: 173

Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 174
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 174

Leu Ala Glu Ala Lys Glu Ala Ala Asn Ala Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 175
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 175

Leu Ala Glu Ala Lys Glu Ala Ala Asn Arg Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 176
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 176

Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 177
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 177

```
Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 178
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 178

```
Leu Ala Gln Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 179
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 179

```
Leu Ala Gln Ala Lys Glu Ala Ala Asn Ala Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 180
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 180

```
Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Glu Ala Ile Leu Ala Ala Leu Pro
        35                  40                  45
```

<210> SEQ ID NO 181
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 181

```
Leu Ala Gln Ala Lys Glu Ala Ala Asn Ala Glu Leu Asp Ala Tyr Gly
1               5                   10                  15
```

```
Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45
```

<210> SEQ ID NO 182
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 182

```
Leu Ala Gln Ala Lys Glu Ala Ala Asn Arg Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45
```

<210> SEQ ID NO 183
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 183

```
Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45
```

<210> SEQ ID NO 184
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 184

```
Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 185
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 185

```
Leu Ala Gln Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30
```

Gly Val Glu Ala Leu Lys Asp Ala Ile Leu Ala Ala Leu Pro
            35                  40                  45

<210> SEQ ID NO 186
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 186

Leu Ala Gln Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 187
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 187

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Glu Ala Ile Leu Ala Ala Leu Pro
            35                  40                  45

<210> SEQ ID NO 188
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 188

Leu Ala Gln Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
            35                  40                  45

<210> SEQ ID NO 189
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 189

Leu Ala Gln Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
            35                  40                  45

<210> SEQ ID NO 190
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 190

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 191
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 191

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45

<210> SEQ ID NO 192
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 192

Leu Ala Glu Ala Lys Glu Ala Ala Asn Arg Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 193
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 193

Leu Ala Glu Ala Lys Glu Ala Ala Asn Ala Glu Leu Asp Cys Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 194

```
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 194

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 195
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 195

Leu Ala Glu Ala Lys Glu Ala Ala Asn Ala Glu Leu Asp Cys Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 196
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 196

Leu Ala Glu Ala Lys Glu Ala Ala Asn Arg Glu Leu Asp Cys Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 197
<211> LENGTH: 46
<212> TYPE: PRT
<213> ORGANISM: Artificial
<220> FEATURE:
<223> OTHER INFORMATION: Engineered albumin-binding polypeptide

<400> SEQUENCE: 197

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 198
<211> LENGTH: 46
<212> TYPE: PRT
<213> ORGANISM: Artificial
```

<220> FEATURE:
<223> OTHER INFORMATION: Engineered albumin-binding polypeptide

<400> SEQUENCE: 198

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45

<210> SEQ ID NO 199
<211> LENGTH: 45
<212> TYPE: PRT
<213> ORGANISM: Artificial
<220> FEATURE:
<223> OTHER INFORMATION: Engineered albumin binding polypeptide

<400> SEQUENCE: 199

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 200
<211> LENGTH: 45
<212> TYPE: PRT
<213> ORGANISM: Artificial
<220> FEATURE:
<223> OTHER INFORMATION: Engineered albumin binding polypeptide

<400> SEQUENCE: 200

Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 201
<211> LENGTH: 45
<212> TYPE: PRT
<213> ORGANISM: Artificial
<220> FEATURE:
<223> OTHER INFORMATION: Engineered albumin binding polypeptide

<400> SEQUENCE: 201

Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 202
<211> LENGTH: 45
<212> TYPE: PRT
<213> ORGANISM: Artificial
<220> FEATURE:
<223> OTHER INFORMATION: Engineered albumin binding polypeptide

<400> SEQUENCE: 202

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 203
<211> LENGTH: 45
<212> TYPE: PRT
<213> ORGANISM: Artificial
<220> FEATURE:
<223> OTHER INFORMATION: Engineered albumin binding polypeptide

<400> SEQUENCE: 203

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 204
<211> LENGTH: 46
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(3)
<223> OTHER INFORMATION: X is selected from E, S, Q and C
<220> FEATURE:
<221> NAME/KEY: MISC_FEATURE
<222> LOCATION: (6)..(6)
<223> OTHER INFORMATION: X is selected from E, S and C
<220> FEATURE:
<221> NAME/KEY: MISC_FEATURE
<222> LOCATION: (7)..(7)
<223> OTHER INFORMATION: X is selected from A and S
<220> FEATURE:
<221> NAME/KEY: MISC_FEATURE
<222> LOCATION: (10)..(10)
<223> OTHER INFORMATION: X is selected from A, S and R
<220> FEATURE:
<221> NAME/KEY: MISC_FEATURE
<222> LOCATION: (14)..(14)
<223> OTHER INFORMATION: X is selected from A, S, C and K
<220> FEATURE:
<221> NAME/KEY: MISC_FEATURE
<222> LOCATION: (26)..(26)
<223> OTHER INFORMATION: X is selected from D and E
<220> FEATURE:
<221> NAME/KEY: MISC_FEATURE
<222> LOCATION: (39)..(39)
<223> OTHER INFORMATION: X is selected from D and E
<220> FEATURE:
<221> NAME/KEY: MISC_FEATURE
<222> LOCATION: (40)..(40)
<223> OTHER INFORMATION: X is selected from A and E
<220> FEATURE:
<221> NAME/KEY: MISC_FEATURE
<222> LOCATION: (43)..(43)
<223> OTHER INFORMATION: X is selected from A and K
<220> FEATURE:
<221> NAME/KEY: MISC_FEATURE
<222> LOCATION: (44)..(44)
<223> OTHER INFORMATION: X is selected from A, S and E
<220> FEATURE:
<221> NAME/KEY: MISC_FEATURE

```
<222> LOCATION: (45)..(45)
<223> OTHER INFORMATION: L in position 45 is present or absent
<220> FEATURE:
<221> NAME/KEY: MISC_FEATURE
<222> LOCATION: (46)..(46)
<223> OTHER INFORMATION: P in position 46 is present or absent

<400> SEQUENCE: 204

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 205
<211> LENGTH: 27
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (27)..(27)
<223> OTHER INFORMATION: PP### albumin binding polypeptide

<400> SEQUENCE: 205

Met Gly Ser Ser His His His His His His Leu Gln Ser Ser Gly Val
1               5                   10                  15

Asp Leu Gly Thr Glu Asn Leu Tyr Phe Gln Gly
            20                  25

<210> SEQ ID NO 206
<211> LENGTH: 27
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (27)..(27)
<223> OTHER INFORMATION: PP013 albumin binding polypeptide

<400> SEQUENCE: 206

Met Gly Ser Ser His His His His His His Leu Gln Ser Ser Gly Val
1               5                   10                  15

Asp Leu Gly Thr Glu Asn Leu Tyr Phe Gln Gly
            20                  25

<210> SEQ ID NO 207
<211> LENGTH: 28
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (28)..(28)
<223> OTHER INFORMATION: PP013 albumin binding polypeptide

<400> SEQUENCE: 207

Met Gly Ser Ser His His His His His His Leu Gln Ser Ser Gly Val
1               5                   10                  15

Asp Leu Gly Thr Glu Asn Leu Tyr Phe Gln Gly Ser
            20                  25
```

```
<210> SEQ ID NO 208
<211> LENGTH: 28
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (28)..(28)
<223> OTHER INFORMATION: PP049 albumin binding polypeptide

<400> SEQUENCE: 208

Met Gly Ser Ser His His His His His His Leu Gln Ser Ser Gly Val
1               5                   10                  15

Asp Leu Gly Thr Glu Asn Leu Tyr Phe Gln Gly Ser
            20                  25

<210> SEQ ID NO 209
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (28)..(29)
<223> OTHER INFORMATION: PP049 albumin binding polypeptide

<400> SEQUENCE: 209

Met Gly Ser Ser His His His His His His Leu Gln Ser Ser Gly Val
1               5                   10                  15

Asp Leu Gly Thr Glu Asn Leu Tyr Phe Gln Gly Ser Gly
            20                  25

<210> SEQ ID NO 210
<211> LENGTH: 10
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Z variant with specificity for Cytokine X
<220> FEATURE:
<221> NAME/KEY: MISC_FEATURE
<222> LOCATION: (10)..(10)
<223> OTHER INFORMATION: PP013 albumin binding polypeptide

<400> SEQUENCE: 210

Met Gly Ser Ser Leu Gln Val Asp Ser Ser
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Z variant with specificity for Cytokine Y
<220> FEATURE:
<221> NAME/KEY: MISC_FEATURE
<222> LOCATION: (10)..(10)
<223> OTHER INFORMATION: PP013 albumin binding polypeptide

<400> SEQUENCE: 211

Met Gly Ser Ser Leu Gln Val Asp Ser Ser
```

```
<210> SEQ ID NO 212
<211> LENGTH: 10
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Zneg is an irrelevant protein
<220> FEATURE:
<221> NAME/KEY: MISC_FEATURE
<222> LOCATION: (10)..(10)
<223> OTHER INFORMATION: PP013 albumin binding polypeptide

<400> SEQUENCE: 212

Met Gly Ser Ser Leu Gln Val Asp Ser Ser
1               5                   10
```

POLYPEPTIDES

CROSS-REFERENCE TO RELATED APPLICATIONS

This application is a Continuation of U.S. application Ser. No. 13/808,713 filed Aug. 20, 2013, now U.S. Pat. No. 9,211,344, which is a U.S. National Stage application of International Patent Application No. PCT/EP2011/061623 filed Jul. 8, 2011, which claims priority to U.S. Ser. No. 61/399,285 filed Jul. 9, 2010 and U.S. Ser. No. 61/403,561 filed Sep. 17, 2010. All of these applications are incorporated by reference herein in their entireties.

TECHNICAL FIELD

The present disclosure relates to a class of engineered polypeptides having a binding affinity for albumin. It also relates to new methods and uses that exploit binding by these and other compounds to albumin in different contexts, some of which have significance for the treatment of disease in mammals including humans.

BACKGROUND

Serum Albumin

Serum albumin is the most abundant protein in mammalian sera (40 g/l; approximately 0.7 mM in humans), and one of its functions is to bind molecules such as lipids and bilirubin (Peters, Advances in Protein Chemistry 37:161, 1985). Serum albumin is devoid of any enzymatic or immunological function. Furthermore, human serum albumin (HSA) is a natural carrier involved in the endogenous transport and delivery of numerous natural as well as therapeutic molecules (Sellers and Koch-Weser, *Albumin Structure, Function and Uses*, eds Rosenoer et al, Pergamon, Oxford, p 159, 1977). The half life of serum albumin is directly proportional to the size of the animal, where for example human serum albumin has a half life of 19 days and rabbit serum albumin has a half life of about 5 days (McCurdy et al, J Lab Clin Med 143:115, 2004). HSA is widely distributed throughout the body, in particular in the interstitial and blood compartments, where it is mainly involved in the maintenance of osmolarity. Structurally, albumins are single-chain proteins comprising three homologous domains and in total 584 or 585 amino acids (Dugaiczyk et al, Proc Natl Acad Sci USA 79:71, 1982). Albumins contain 17 disulfide bridges and a single reactive thiol, cysteine in position 34, but lack N-linked and O-linked carbohydrate moieties (Peters, 1985, supra; Nicholson et al, Br J Anaesth 85:599, 2000).

Fusion or Association with HSA Results in Increased In Vivo Half Life of Proteins Several strategies have been reported to either covalently couple proteins directly to serum albumins or to a peptide or protein that will allow in vivo association to serum albumins. Examples of the latter approach have been described e.g. in WO91/01743, in WO01/45746 and in Dennis et al (J Biol Chem 277:35035-43, 2002). The first document describes inter alia the use of albumin binding peptides or proteins derived from streptococcal protein G (SpG) for increasing the half life of other proteins. The idea is to fuse the bacterially derived, albumin binding peptide/protein to a therapeutically interesting peptide/protein, which has been shown to have a rapid elimination from blood. The thus generated fusion protein binds to serum albumin in vivo, and benefits from its longer half life, which increases the net half life of the fused therapeutically interesting peptide/protein. WO01/45746 and Dennis et al relate to the same concept, but here, the authors utilize relatively short peptides to bind serum albumin. The peptides were selected from a phage displayed peptide library. In Dennis et al, earlier work is mentioned in which the enhancement of an immunological response to a recombinant fusion of the albumin binding domain of streptococcal protein G to human complement receptor Type 1 was found. US patent application published as US2004/0001827 (Dennis) also discloses the use of constructs comprising peptide ligands, again identified by phage display technology, which bind to serum albumin and which are conjugated to bioactive compounds for tumor targeting.

Albumin Binding Domains of Bacterial Receptor Proteins

Streptococcal protein G (SpG) is a bi-functional receptor present on the surface of certain strains of streptococci and is capable of binding to both IgG and serum albumin (Björck et al, Mol Immunol 24:1113, 1987). The structure is highly repetitive with several structurally and functionally different domains (Guss et al, EMBO J 5:1567, 1986), more precisely three Ig-binding domains and three serum albumin binding domains (Olsson et al, Eur J Biochem 168:319, 1987). The structure of one of the three serum albumin binding domains in SpG has been determined, showing a three-helix bundle fold (Kraulis et al, FEBS Lett 378:190, 1996, Johansson et al, J. Biol. Chem. 277:8114-20, 2002). A 46 amino acid motif was defined as ABD (albumin binding domain) and has subsequently also been designated G148-GA3 (GA for protein G-related albumin binding). In for example WO09/016043, albumin binding variants of the 46 amino acid motif ABD are disclosed.

Other bacterial albumin binding domains than the ones in protein G have also been identified, some of which are structurally similar to the ones of protein G. Examples of proteins containing such albumin binding domains are the PAB, PPL, MAG and ZAG proteins (Rozak et al, Biochemistry 45:3263-3271, 2006). Studies of structure and function of such albumin binding domains have been carried out and reported e.g. by Johansson and co-workers (Johansson et al, J Mol Biol 266:859-865, 1997). Furthermore, Rozak et al have reported on the creation of artificial variants of G148-GA3, which were selected and studied with regard to different species specificity and stability (Rozak et al, Biochemistry 45:3263-3271, 2006), whereas Jonsson et al developed artificial variants of G148-GA3 having very much improved affinity for human serum albumin (Jonsson et al, Prot Eng Des Sel 21:515-27, 2008). For some of the variants a higher affinity was achieved at the cost of reduced thermal stability.

In addition to the three-helix containing proteins described above, there are also other unrelated bacterial proteins that bind albumin.

ABD and Immunization

Recently, a few T- and B-cell epitopes were experimentally identified within the albumin binding region of Streptococcal protein G strain 148 (G148) (Goetsch et al, Clin Diagn Lab Immunol 10:125-32, 2003). The authors behind the study were interested in utilizing the T-cell epitopes of G148 in vaccines, i.e. to utilize the inherent immune-stimulatory property of the albumin binding region. Goetsch et al additionally found a B-cell epitope, i.e. a region bound by antibodies after immunization, in the sequence of G148.

In pharmaceutical compositions for human administration no immune-response is desired. Therefore, the albumin binding domain G148 is as such unsuitable for use in such compositions due to its abovementioned immune-stimulatory properties.

Description

The above drawbacks and deficiencies of the prior art are overcome or alleviated by, in a first aspect, an albumin binding polypeptide, comprising an amino acid sequence selected from i)
(SEQ ID NO: 204)
LAX$_3$AKX$_6$X$_7$ANX$_{10}$ ELDX$_{14}$YGVSDF YKRLIX$_{26}$KAKT

VEGVEALKX$_{39}$X$_{40}$ILX$_{43}$X$_{44}$LP wherein independently of each other
X$_3$ is selected from E, S, Q and C;
X$_6$ is selected from E, S and C;
X$_7$ is selected from A and S;
X$_{10}$ is selected from A, S and R;
X$_{14}$ is selected from A, S, C and K;
X$_{26}$ is selected from D and E;
X$_{39}$ is selected from D and E;
X$_{40}$ is selected from A and E;
X$_{43}$ is selected from A and K;
X$_{44}$ is selected from A, S and E;
L in position 45 is present or absent; and
P in position 46 is present or absent;
and
ii) An Amino Acid Sequence which has at Least 95% Identity to the Sequence Defined in i).

The above defined class of sequence related polypeptides having a binding affinity for albumin is derived from a common parent polypeptide sequence, which folds into a three alpha helix bundle domain. More specifically, the polypeptides as described above are derived from a model building based on a structure of a complex between serum albumin and the albumin binding domain G148-GA3 (Lejon et al, J Biol Chem 279:42924-8, 2004), as well as analyses of binding and structural properties of a number of mutational variants of the common parent polypeptide sequence. The above defined amino acid sequence i) comprises amino acid substitutions as compared to the parent polypeptide sequence that result in a class of polypeptides which are expected to fold into an almost identical three helix bundle domain. While the parent polypeptide sequence already comprises a binding surface for interaction with albumin, that binding surface is modified by some of the substitutions according to the above definition. The substitutions according to the above definition provide an improved albumin binding ability as compared to the parent polypeptide sequence.

The albumin binding polypeptides according to the first aspect of the disclosure exhibit a set of characteristics, which, for example, make them suitable for use as fusion or conjugate partners for therapeutic molecules for human administration. The albumin binding polypeptides according to the present disclosure demonstrate, for example in comparison with related albumin binding polypeptides such as the albumin binding domain G148-GA3 and the albumin binding polypeptides disclosed in WO09/016043, at least five of the following six characteristics:

The polypeptides display a different surface compared to, for example, G148-GA3 and other bacterially derived albumin binding domains. The difference may decrease or eliminate any risk for antibody reactions in a subject, such as a human, which has been previously exposed to such bacterial proteins.

The polypeptides comprise fewer potential T-cell epitopes than, for example, G148-GA3 and other related, but different, mutational variants of the common parent polypeptide sequence, and hence exhibit low immunogenicity when administered to a subject, such as a human.

The polypeptides display a lower reactivity with circulating antibodies when administered to a subject, such as a human. Thus, by amino acid substitutions in the surface of the polypeptides exposed to circulating antibodies, i.e. in the polypeptide surface not involved in the binding interaction with albumin, antibody cross-reactivity is reduced as compared to, for example, antibody cross-reactivity caused by G148-GA3 as measured in a test set of human sera.

The polypeptides have a high albumin binding ability, both in terms of a higher binding affinity, as defined by a $K_D$ value, and in terms of a slower off-rate, as defined by a $k_{off}$ value, than, for example, known naturally occurring albumin binding polypeptides, such as the albumin binding domains derived from bacterial proteins.

The polypeptides comprise fewer amino acid residues that are associated with stability problems of polypeptides than, for example, known naturally occurring albumin binding polypeptides, such as the albumin binding domains derived from bacterial proteins. Thus, the polypeptides comprise, for example, no oxidation-prone methionines or tryptophanes and only one asparagine.

The polypeptides have a higher structural stability, as defined by a melting point of above 55° C., than previous albumin binding polypeptides, such as those disclosed in WO09/016043.

In one embodiment, the albumin binding polypeptide according to the first aspect display all six of the above listed characteristics. In another embodiment, the albumin binding polypeptide according to the first aspect displays, when bound to albumin, a more hydrophilic profile than, for example, previous albumin binding polypeptides, such as those disclosed in WO09/016043. The surface of the albumin binding polypeptide which is exposed to the surroundings when the polypeptide interacts with albumin comprises fewer amino acid residues that confer surface hydrophobicity.

As the skilled person will realize, the function of any polypeptide, such as the albumin binding capacity of the polypeptides according to the first aspect, is dependent on the tertiary structure of the polypeptide. It is however possible to make changes to the sequence of amino acids in an α-helical polypeptide without affecting the structure thereof (Taverna and Goldstein, J Mol Biol 315(3):479-84, 2002; He et al, Proc Natl Acad Sci USA 105(38):14412-17, 2008). Thus, modified variants of i), which are such that the resulting sequence is at least 95% identical to a sequence belonging to the class defined by i), are also encompassed by the first aspect. For example, it is possible that an amino acid residue belonging to a certain functional grouping of amino acid residues (e.g. hydrophobic, hydrophilic, polar etc) could be exchanged for another amino acid residue from the same functional group.

The term "% identical" or "% identity", as used in the specification and claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The shortest of the aligned sequences may in some instances be the target sequence, such as the albumin binding polypeptide disclosed herein. In other instances, the query sequence may constitute the shortest of the aligned sequences. The query sequence may for example consist of at least 10 amino acid residues, such as at least 20 amino acid residues, such as at least 30 amino acid residues, such as at least 40 amino acid residues, for example 45 amino acid residues. The amino acid residues at each position are compared, and the percentage of positions in the query sequence that have identical correspondences in the target sequence is reported as % identity.

In one embodiment of the albumin binding polypeptide according to the first aspect, $X_6$ is E.

In another embodiment of the albumin binding polypeptide according to this aspect, $X_3$ is S.

In another embodiment of the albumin binding polypeptide according to this aspect, $X_3$ is E.

In another embodiment of the albumin binding polypeptide according to this aspect, $X_7$ is A.

In another embodiment of the albumin binding polypeptide according to this aspect, $X_{14}$ is S.

In another embodiment of the albumin binding polypeptide according to this aspect, $X_{14}$ is C.

In another embodiment of the albumin binding polypeptide according to this aspect, $X_{10}$ is A.

In another embodiment of the albumin binding polypeptide according to this aspect, $X_{10}$ is S.

In another embodiment of the albumin binding polypeptide according to this aspect, $X_{26}$ is D.

In another embodiment of the albumin binding polypeptide according to this aspect, $X_{26}$ is E.

In another embodiment of the albumin binding polypeptide according to this aspect, $X_{39}$ is D.

In another embodiment of the albumin binding polypeptide according to this aspect, $X_{39}$ is E.

In another embodiment of the albumin binding polypeptide according to this aspect, $X_{40}$ is A.

In another embodiment of the albumin binding polypeptide according to this aspect, $X_{43}$ is A.

In another embodiment of the albumin binding polypeptide according to this aspect, $X_{44}$ is A.

In another embodiment of the albumin binding polypeptide according to this aspect, $X_{44}$ is S.

In another embodiment of the albumin binding polypeptide according to this aspect, the L residue in position 45 is present.

In another embodiment of the albumin binding polypeptide according to this aspect, the P residue in position 46 is present.

In another embodiment of the albumin binding polypeptide according to this aspect, the P residue in position 46 is absent.

In another embodiment, the albumin binding polypeptide according to this aspect is subject to the proviso that $X_7$ is neither L, E nor D.

The albumin binding polypeptide according to the first aspect may be prepared for conjugation with a suitable conjugation partner by the replacement of surface exposed amino acid residues with, for example, either a cysteine or a lysine. These replacements may be introduced into the N-terminal helix, i.e. helix one, of the polypeptide, which is the helix situated furthest away from the serum albumin when the albumin binding polypeptide is bound to serum albumin. Thus, a lysine residue in position $X_{14}$ of the sequence defined in i) may be used to enable site-directed conjugation. This may furthermore be advantageous when the molecule is made by chemical peptide synthesis, since orthogonal protection of the epsilon-amino group of said lysine may be utilized. Furthermore, a cysteine residue may be introduced into the amino acid sequence to enable site-directed conjugation. For example, a cysteine residue may be introduced into any one of the positions $X_3$, $X_6$ and/or $X_{14}$ in accordance with the above definition.

Coupling of a conjugation partner to the epsilon-amine of a lysine or the thiol group of a cysteine represents two chemically different alternatives to obtain site-directed conjugation using an amino acid residue within the amino acid sequence i). As the skilled person understands, other chemical alternatives for preparing an amino acid sequence for conjugation exist, and are as such also within the scope of the present disclosure. One example of such a chemistry is the click-like chemistry enabled by the introduction of a tyrosine as presented by Ban et al (J Am Chem Soc 132: 1523-5, 2009).

The terms "albumin binding" and "binding affinity for albumin" as used in this specification refer to a property of a polypeptide which may be tested for example by the use of surface plasmon resonance technology, such as in a Biacore instrument. For example as described in the examples below, albumin binding affinity may be tested in an experiment in which albumin, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing albumin, or a fragment thereof, is passed over the chip. Albumin may, in this regard, be a serum albumin from a mammal, such as human serum albumin. The skilled person may then interpret the results obtained by such experiments to establish at least a qualitative measure of the binding affinity of the polypeptide for albumin. If a quantitative measure is desired, for example to determine a $K_D$ value for the interaction, surface plasmon resonance methods may also be used. Binding values may for example be defined in a Biacore2000 instrument (GE Healthcare). Albumin is suitably immobilized on a sensor chip of the measurement, and samples of the polypeptide whose affinity is to be determined are prepared by serial dilution and injected. $K_D$ values may then be calculated from the results using for example the 1:1 Langmuir binding model of the BIAevaluation 4.1 software provided by the instrument manufacturer (GE Healthcare).

In one embodiment, the albumin binding polypeptide according to this aspect binds to albumin such that the $k_{off}$ value of the interaction is at most $5 \times 10^{-5}$ $s^{-1}$, such as at most $5 \times 10^{-6}$ $s^{-1}$.

As described above, the albumin binding polypeptides as defined by the amino acid sequence i) are derived from a common parent polypeptide sequence which folds into a three alpha helix bundle domain. In one embodiment, the three helix domain of this parent polypeptide sequence forms part of protein G from *Streptococcus* strain G148, in particular domain GA3.

In another embodiment, the amino acid sequence of the albumin binding polypeptide is selected from any one of SEQ ID NO:1-144 and SEQ ID NO:164-203, such as selected from any one of SEQ ID NO:1-144. More specifically, the amino acid sequence is selected from SEQ ID NO:4-5, SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:41-42, SEQ ID NO:49-50, SEQ ID NO:164-170 and SEQ ID NO:192-203. Thus, the amino acid sequence may be selected from SEQ ID NO:4-5, SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:41-42 and SEQ ID NO:49-50.

In one embodiment, the albumin binding polypeptide according to this aspect further comprises one or more additional amino acid residues positioned at the N- and/or the C-terminal of the sequence defined in i). These additional amino acid residues may play a role in enhancing the binding of albumin by the polypeptide, and improving the conformational stability of the folded albumin binding domain, but may equally well serve other purposes, related for example to one or more of production, purification, stabilization in vivo or in vitro, coupling, labeling or detection of the polypeptide, as well as any combination thereof. Such additional amino acid residues may comprise one or more amino acid residue(s) added for purposes of chemical coupling, e.g. to a chromatographic resin to obtain an affinity matrix or to a chelating moiety for complexing with a radiometal.

The amino acids directly preceding or following the alpha helix at the N- or C-terminus of the amino acid sequence i) may thus in one embodiment affect the conformational stability. One example of an amino acid residue which may contribute to improved conformational stability is a serine residue positioned at the N-terminal of the amino acid sequence i) as defined above. The N-terminal serine residue may in some cases form a canonical S-X-X-E capping box, by involving hydrogen bonding between the gamma oxygen of the serine side chain and the polypeptide backbone NH of the glutamic acid residue. This N-terminal capping may contribute to stabilization of the first alpha helix of the three helix domain constituting the albumin binding polypeptide according to the first aspect of the disclosure.

Thus, in one embodiment, the additional amino acids comprise at least one serine residue at the N-terminal of the polypeptide. The amino acid sequence is in other words preceded by one or more serine residue(s). In another embodiment of the albumin binding polypeptide, the additional amino acids comprise a glycine residue at the N-terminal of the polypeptide. It is understood that the amino acid sequence i) may be preceded by one, two, three, four or any suitable number of amino acid residues. Thus, the amino acid sequence may be preceded by a single serine residue, a single glycine residue or a combination of the two, such as a glycine-serine (GS) combination or a glycine-serine-serine (GSS) combination. Examples of albumin binding polypeptides comprising additional amino residues at the N-terminal are set out in SEQ ID NO:145-163, such as in SEQ ID NO:145-148 and SEQ ID NO:162-163. In yet another embodiment, the additional amino acid residues comprise a glutamic acid at the N-terminal of the polypeptide as defined by the sequence i).

Similarly, C-terminal capping may be exploited to improve stability of the third alpha helix of the three helix domain constituting the albumin binding polypeptide. A proline residue, when present at the C-terminal of the amino acid sequence defined in i), may at least partly function as a capping residue. In such a case, a lysine residue following the proline residue at the C-terminal may contribute to further stabilization of the third helix of the albumin binding polypeptide, by hydrogen bonding between the epsilon amino group of the lysine residue and the carbonyl groups of the amino acids located two and three residues before the lysine in the polypeptide backbone, e.g., when both L45 and P46 are present, the carbonyl groups of the leucine and alanine residues of the amino acid sequence defined in i). Thus, in one embodiment, the additional amino acids comprise a lysine residue at the C-terminal of the polypeptide.

As discussed above, the additional amino acids may be related to the production of the albumin binding polypeptide. In particular, when an albumin binding polypeptide according to an embodiment in which P46 is present is produced by chemical peptide synthesis, one or more optional amino acid residues following the C-terminal proline may provide advantages. Such additional amino acid residues may for example prevent formation of undesired substances, such as diketopiperazine at the dipeptide stage of the synthesis. One example of such an amino acid residue is glycine. Thus, in one embodiment, the additional amino acids comprise a glycine residue at the C-terminal of the polypeptide, directly following the proline residue or following an additional lysine and/or glycine residue as accounted for above. Alternatively, polypeptide production may benefit from amidation of the C-terminal proline residue of the amino acid sequence i), when present. In this case, the C-terminal proline comprises an additional amine group at the carboxyl carbon. In one embodiment of the polypeptides described herein, particularly those ending at its C-terminus with proline or other amino acid known to racemize during peptide synthesis, the above-mentioned addition of a glycine to the C-terminus or amidation of the proline, when present, can also counter potential problems with racemization of the C-terminal amino acid residue. If the polypeptide, amidated in this way, is intended to be produced by recombinant means, rather than by chemical synthesis, amidation of the C-terminal amino acid can be performed by several methods known in the art, e.g. through the use of amidating PAM enzyme.

Examples of albumin binding polypeptides comprising additional amino acid residues at the C-terminal are set out in SEQ ID NO:145-152, such as in SEQ ID NO:148-150. The skilled person is aware of methods for accomplishing C-terminal modification, such as by different types of pre-made matrices for peptide synthesis.

In another embodiment, the additional amino acid residues comprise a cysteine residue at the N- and/or C-terminal of the polypeptide. Such a cysteine residue may directly precede and/or follow the amino acid sequence as defined in i) or may precede and/or follow any other additional amino acid residues as described above. Examples of albumin binding polypeptides comprising a cysteine residue at the N- and/or C-terminal of the polypeptide chain are set out in SEQ ID NO:149-150 (C-terminal) and SEQ ID NO:151-152 (N-terminal). By the addition of a cysteine residue to the polypeptide chain, a thiol group for site directed conjugation of the albumin binding polypeptide may be obtained. Alternatively, a selenocysteine residue may be introduced at the C-terminal of the polypeptide chain, in a similar fashion as for the introduction of a cysteine residue, to facilitate site-specific conjugation (Cheng et al, Nat Prot 1:2, 2006).

In one embodiment, the albumin binding polypeptide comprises no more than two cysteine residues. In another embodiment, the albumin binding polypeptide comprises no more than one cysteine residue.

In another embodiment, the additional amino acid residues of the albumin binding polypeptide comprise a "tag" for purification or detection of the polypeptide, such as a hexahistidyl (His$_6$) tag, or a "myc" ("c-Myc") tag or a "FLAG" tag for interaction with antibodies specific to the tag and/or to be used in purification. The skilled person is aware of other alternatives.

In yet another embodiment, the albumin binding polypeptide according to this aspect binds to human serum albumin. In other embodiments, the albumin binding polypeptide binds to albumin from other species than the human species, such as albumin from mouse, rat, dog and cynomolgus macaques.

The "additional amino acid residues" discussed above may also constitute one or more polypeptide domain(s) with any desired function, such as the same binding function as the first, albumin binding domain, or another binding function, or a therapeutic function, or an enzymatic function, or a fluorescent function, or mixtures thereof.

There is consequently in another, related aspect, provided a fusion protein or conjugate comprising
i) a first moiety consisting of an albumin binding polypeptide according to the first aspect as described herein; and
ii) a second moiety consisting of a polypeptide having a desired biological activity.

A fusion protein or conjugate comprising an albumin binding polypeptide according to the first aspect of the disclosure and a second moiety may increase the in vitro and/or the in vivo half life of the second moiety, as compared to the in vivo half life of the second moiety per se. As a consequence, when a fusion protein or conjugate according to this aspect is administered to a subject, such as a human subject, the in vivo exposure to the second moiety may increase, which may lead to improved potency of the biological activity of the second moiety, as compared to the potency of in vivo exposure of the second moiety when administered by itself.

The desired biological activity may, for example, be a therapeutic activity, a binding activity or an enzymatic activity. When the desired biological activity is a therapeutic activity, the second moiety showing this activity may be a therapeutically active polypeptide. Non-limiting examples of therapeutically active polypeptides are biomolecules, such as molecules selected from the group consisting of human endogenous enzymes, hormones, growth factors, chemokines, cytokines and lymphokines, and non-human biologically active proteins, such as proteins selected from the group consisting of bacterial toxins (e.g. *pseudomonas* exotoxin and staphylococcal and streptococcal superantigens), enzymes (e.g. RNase and beta-lactamase) and activating proteins (e.g. streptokinase). Non-limiting examples of therapeutically active biomolecules which may prove useful in a fusion or conjugate with the albumin binding polypeptide are selected from the group consisting of IL-2, GLP-1, BNP (Alb-beta-natriuretic peptide), IL-1-RA (interleukin-1 receptor antagonist), KGF (keratinocyte growth factor), STEMGEN, growth hormone (GH), G-CSF, CTLA-4, myostatin, Factor VII, Factor VIII and Factor IX.

The leaky defective blood vessels of tumor tissue make its vasculature (endothelial barrier) permeable for macromolecules, whereas in blood vessels of healthy tissue only small molecules can pass the endothelial barrier. Likewise, the permeability of the blood-joint barrier for albumin in inflamed joints of rheumatoid arthritis patients is markedly increased. Thus, fusion proteins or conjugates according to this aspect are likely to permeate blood vessels in tumor tissue and the blood-joint barrier in inflamed joints.

When said desired biological activity of the second moiety is a binding activity, said second moiety may be a binding polypeptide capable of selective interaction with a target molecule. Such a binding polypeptide may for example be selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, other three helix domains, lipocalins, ankyrin repeat domains, cellulose binding domains, γ crystallines, green fluorescent protein, human cytotoxic T lymphocyte-associated antigen 4, protease inhibitors such as Kunitz domains, PDZ domains, SH3 domains, peptide aptamers, staphylococcal nuclease, tendamistats, fibronectin type III domain, transferrin, zinc fingers and conotoxins.

In some embodiments, the target molecule for binding of said target binding polypeptide may be selected from the group consisting of amyloid β (Aβ) peptide of Alzheimer's disease; other disease-associated amyloid peptides; toxins, such as bacterial toxins and snake venoms; blood clotting factors, such as von Willebrand factor; interleukins, such as IL-13; myostatin; pro-inflammatory factors, such as TNF-α, TNF-α receptor, IL-1, IL-8 and IL-23; complement factors, such as C3 and C5; hypersensitivity mediators, such as histamine and IgE; tumor-related antigens, such as CD19, CD20, CD22, CD30, CD33, CD40, CD52, CD70, cMet, HER1, HER2, HER3, HER4, CAIX (carbonic anhydrase IX), CEA, IL-2 receptor, MUC1, PSMA, TAG-72; and other biological molecules such as G-CSF, GM-CSF, growth hormone (GH), insulin and somatostatin.

As the skilled person understands, the albumin binding polypeptide according to the first aspect may be useful in a fusion protein or as a conjugate partner to any other moiety. Therefore, the above lists of therapeutically active polypeptides, binding polypeptides and target molecules should not be construed as limiting in any way.

In one embodiment of a fusion protein or conjugate according to the present disclosure, the second moiety is conjugated to the albumin binding polypeptide via a lysine or cysteine residue added to the N- or C-terminal of the albumin binding polypeptide or via a lysine or cysteine residue at a position within the albumin binding polypeptide, such as at a position selected from $X_3$, $X_6$ and $X_{14}$. If the conjugation site is one within the amino acid sequence i) of the albumin binding polypeptide, such as a cysteine in position $X_{14}$, no additional amino acids need to be added to the albumin binding polypeptide for the purpose of enabling conjugation to the second moiety. A conjugation site within the polypeptide chain as defined by i) may moreover shield the polypeptide against cross-reacting antibodies, in particular the portion of the polypeptide close to the conjugation site. Without wishing to be bound by theory, when the conjugate via the albumin binding polypeptide is bound to serum albumin in vivo, i.e. situated in the binding pocket of serum albumin, the second moiety, conjugated at a position within for example helix one of the three helix domain constituting the albumin binding polypeptide, is likely to point away from the serum albumin to which the albumin binding polypeptide is bound. In addition, a conjugation site within the albumin binding polypeptide may impair the presentation of the portion of the peptides otherwise derived from this portion of the polypeptide to T-cells due to, for example, effects on processing in the antigen presenting cell, impaired fit of potential peptides in the peptide binding grove of the MCH class II molecule, and remodeled peptide surface available to the T-cell receptor (due to the conjugated portion sticking out). Thus, the immunogenicity of the portion of the conjugate near the conjugation site is expected to become further reduced after conjugation.

Due to the high affinity between the albumin binding polypeptide of the present disclosure and serum albumin, a conjugate or fusion protein comprising such an albumin binding polypeptide might be regarded as an indirect complex with serum albumin. A conjugate or a fusion protein according to the present disclosure thus provides an alternative to the frequently used method of exploiting direct conjugates or fusions with serum albumin. Such direct conjugates with serum albumin are frequently inhomogeneous, irrespective of what method is used for coupling. When a specific molecule is coupled to serum albumin via an amino group of a lysine residue, any one of a large number of lysines on the surface of the serum albumin molecule may be targeted, which gives a random conjugation site and a random product. Although thiol coupling via the single unpaired cysteine in human serum albumin (in position 34, Peters, 1985, supra) seems to offer an alternative method for obtaining a direct conjugate, such a methodology frequently does not lead to a homogeneous product. Only 20-60% of the molecules in commercially available (human) serum albumin display a free thiol group, whereas the rest are blocked by thiol compounds such as cysteine, homocysteine or glutathione. In contrast, conjugation to the three helix domain of the albumin binding polypeptide according to the present disclosure may be performed site-specifically. This may be accomplished, as discussed above, either by coupling to one or more cysteines, to a selenocysteine, or to a designated lysine (orthogonally protected during synthesis).

According to this aspect of the present disclosure, the second moiety having the desired biological activity may either be conjugated to the three helix domain of the albumin binding polypeptide or produced as a fusion protein with the same. A non-limiting example of a conjugate according to the present disclosure is given below. Glucagon-like peptide 1 (GLP-1), or a derivative thereof, is a small polypeptide which may suitably be present as a second moiety in a conjugate with the albumin binding polypeptide. Conjugation of GLP-1 to the albumin binding polypeptide may be performed in any one of the positions of the polypeptide sequence as described above. The conjugate may as such be produced in a non-biological process and is expected to display a significantly enhanced potency as compared to the potency of GLP-1 per se. Conjugation may be employed with both small polypeptides or proteins, such as GLP-1, or with larger polypeptides or proteins. A conjugate according to the present disclosure may typically comprise a non-amino acid spacer moiety, such as polyethylene glycol (PEG).

Other polypeptides or proteins may be combined with the amino acid sequence of the albumin binding polypeptide in the form of a fusion protein. Such a fusion protein may furthermore comprise one or more spacer amino acid residues between the first and second moieties.

As described above, the albumin binding polypeptide according to the first aspect binds serum albumin from several species, including mouse, rat, dog and cynomolgus macaques. Thus, a fusion protein or conjugate according to the present disclosure may contribute to enhancing the biological effect of a second moiety, not only in a human subject, but also in animal models. A number of endogenous proteins have been produced as direct fusions with human serum albumin, examples of such proteins include G-CSF, GH, interferons, CD4, IL-2, insulin, glucagon, GLP-1, antibody Fab fragments and protease inhibitors like Kunitz-domain derived proteins. Such direct fusions may however not be fully evaluated in animal models. This is due to the fact that human serum albumin does not interact properly with the endogenous Fc neonatal receptor (FcRn), e.g. in the commonly used animal models mouse and rat, and that this interaction is an important factor contributing to the long circulation time of serum albumin. As described above, a conjugate or a fusion protein according to the present disclosure may, in the presence of serum albumin, combine with albumin and function as an indirect fusion with albumin. This makes a conjugate or a fusion protein comprising an albumin binding polypeptide according to the first aspect useful in preclinical model species, provided that the second moiety is biologically active in the selected species.

In one embodiment, there is provided a fusion protein or conjugate comprising a further moiety consisting of a polypeptide having a further, desired biological activity, which may be the same as or different from that of the second moiety. One specific example of such a fusion protein or conjugate comprises a therapeutically active polypeptide as defined above as a second moiety and a binding polypeptide as defined above as a further moiety.

With regard to the description above of fusion proteins or conjugates incorporating an albumin binding polypeptide according to the first aspect, it is to be noted that the designation of first, second and further moieties is made for clarity reasons to distinguish between albumin binding polypeptide or polypeptides according to the present disclosure on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate.

In a related aspect, there is provided an albumin binding polypeptide, fusion protein or conjugate as defined in the present disclosure, further comprising an organic molecule, such as a cytotoxic agent. Non-limiting examples of cytotoxic agents which may be fused or conjugated to an albumin binding polypeptide according to the first aspect, or combined with a fusion protein or conjugate according to the second aspect, are selected from calicheamycin, auristatin, doxorubicin, maytansinoid, taxol, ecteinascidin, geldanamycin, methotrexate and their derivatives, and combinations thereof. Previously, attempts have been made to treat various disorders with direct albumin conjugates. Such direct albumin conjugates have been exploited e.g. with doxorubicin in cancer (Kratz et al, J Med Chem 45: 5523-33, 2002) and metotrexate in rheumatoid arthritis (Wunder et al, J Immunol 170:4793-4801, 2003). It is to be understood that the albumin binding polypeptide, either by itself or as a moiety in a fusion protein or conjugate, by its high albumin binding ability provides indirect means of construing albumin complexes, and thus may provide an alternative treatment method compared to the attempts mentioned above.

The above aspects furthermore encompass polypeptides in which the albumin binding polypeptide according to the first aspect, or the albumin binding polypeptide as comprised in a fusion protein or conjugate according to the second aspect, has been provided with a label group, such as a label selected from the group consisting of fluorescent dyes and metals, chromophoric dyes, chemiluminescent compounds and bioluminescent proteins, enzymes, radionuclides and particles, for example for purposes of detection of the polypeptide. In particular, the disclosure encompasses a radiolabeled polypeptide consisting of a radiochelate of an albumin binding polypeptide, fusion protein or conjugate as described herein and a radionuclide, such as a radioactive metal.

In embodiments where the labeled albumin binding polypeptide comprises an albumin binding polypeptide according to the first aspect of the disclosure and a label, the labeled polypeptide may for example be used for labeling serum albumin indirectly. Due to the strong association between the labeled polypeptide and serum albumin, the labeled polypeptide may be used for example to study vascular permeability and blood pool.

In other embodiments, the labeled albumin binding polypeptide is present as a moiety in a fusion protein or conjugate also comprising a second moiety having a desired biological activity. The label may in some instances be coupled only to the albumin binding polypeptide, and in some instances both to the albumin binding polypeptide and to the second moiety of the conjugate or fusion protein. When reference is made to a labeled polypeptide, this should be understood as a reference to all aspects of polypeptides as described herein, including fusion proteins and conjugates comprising an albumin binding polypeptide and a second and optionally further moieties. Thus, a labeled polypeptide may contain only the albumin binding polypeptide and e.g. a therapeutic radionuclide, which may be chelated or covalently coupled to the albumin binding polypeptide, or contain the albumin binding polypeptide, a therapeutic radionuclide and a second moiety such as a small molecule having a desired biological activity such as therapeutic efficacy. In embodiments where the albumin binding polypeptide, fusion protein or conjugate is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the albumin binding polypeptide, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators. In one embodiment, the albumin binding polypeptide, fusion protein or conjugate comprises a chelating environment provided by a polyaminopolycarboxylate chelator conjugated to the albumin binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, the chelating environment of the albumin binding polypeptide, fusion protein or conjugate is provided by DOTA or a derivative thereof. More specifically, one group of chelating polypeptides encompassed by the present disclosure is made by reacting the DOTA derivative 1,4,7,10-tetraazacyclododecane-1,4,7-tris-acetic acid-10-maleimidoethylacetamide (maleimidomonoamide-DOTA) with, for example, a thiol group of the albumin binding polypeptide, for example as described in Example 5.

The high kinetic inertness, i.e. the slow rate of dissociation of metal from DOTA, favors stable attachment of a radionuclide. However, elevated temperatures are required for labeling due to a slow association rate. For this reason, DOTA derivatives are widely used for labeling of short peptides, such as the albumin binding polypeptides of the present disclosure, which display binding functionality following incubation at temperatures required for the labeling reaction.

The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

It has been found that backbone-modified semi-rigid variants of DTPA provide adequate stability for labeling with $^{90}$Y of e.g. ZEVALIN. Though acyclic chelators are less inert, and consequently, less stable than macrocyclic ones, their labeling is rapid enough even at ambient temperature. For this reason, they might be used for labeling of fusion proteins or conjugates according to the present disclosure. Detailed protocols for coupling of polyaminopolycarboxylate chelators to targeting proteins and peptides have been published by Cooper et al (Nat Prot 1: 314-7, 2006) and by Sosabowski and Mather (Nat Prot 1:972-6, 2006).

An albumin binding polypeptide, a fusion protein or conjugate according to the aspects described herein coupled to a polyaminopolycarboxylate chelator may be used to provide a radiolabeled polypeptide consisting of a radiochelate of the albumin binding polypeptide, fusion protein or conjugate coupled to the chelator and a radionuclide suitable for medical imaging, the radionuclide being selected from the group consisting of $^{61}$Cu, $^{64}$Cu, $^{66}$Ga, $^{67}$Ga, $^{68}$Ga, $^{110}$In, $^{111}$In, $^{44}$Sc and $^{86}$Y, or with a radionuclide suitable for therapy, the radionuclide being selected from the group consisting of $^{225}$Ac, $^{212}$Bi, $^{213}$Bi, $^{67}$Cu $^{166}$Ho, $^{177}$Lu, $^{212}$Pb, $^{149}$Pm, $^{153}$Sm, $^{227}$Th and $^{90}$Y, wherein the radionuclide is complexed with the albumin binding polypeptide via a chelator.

In embodiments thereof, the polypeptide may also be radiolabeled with non-metal radioisotopes using so called indirect labeling. Thus, for labeling with for example $^{18}$F, $^{76}$Br, different iodine isotopes and $^{211}$At, intermediate "linker molecules" are used for labeling. Such a linker molecule should contain two functional moieties, one providing rapid and efficient radiolabeling, and another enabling rapid and efficient coupling to the proteins, e.g. to amine groups, or preferably to the thiol group of a unique cysteine, such as in position $X_{14}$ of the albumin binding polypeptide. For example a malemide group reacts with thiol groups to form a stable thioether bond. The "linker molecule" may first be reacted with the radiolabel and subsequently with the thiol or the selenothiol group of the protein.

In another aspect, there is provided a polynucleotide encoding an albumin binding polypeptide or a fusion protein as described herein. Also encompassed is a method of producing an albumin binding polypeptide or a fusion protein as described above, comprising expressing the polynucleotide, an expression vector comprising the polynucleotide and a host cell comprising the expression vector.

The albumin binding polypeptide of the present disclosure may alternatively be produced by non-biological peptide synthesis using amino acids and/or amino acid derivatives having protected reactive side-chains, the non-biological peptide synthesis comprising step-wise coupling of the amino acids and/or the amino acid derivatives to form a polypeptide according to the first aspect having protected reactive side-chains, removal of the protecting groups from the reactive side-chains of the polypeptide, and folding of the polypeptide in aqueous solution.

Thus, normal amino acids (e.g. glycine, alanine, phenylalanine, isoleucine, leucine and valine) and pre-protected amino acid derivatives are used to sequentially build a polypeptide sequence, in solution or on a solid support in an organic solvent. One specific example of peptide synthesis on solid support is described in Example 5. When a complete polypeptide sequence is built, the protecting groups are removed and the polypeptide is allowed to fold in an aqueous solution. Each polypeptide according to the present disclosure reversibly folds into a three helix bundle domain without added factors, and hence folds spontaneously.

The conjugate according to the second aspect may be produced by a method comprising producing an albumin binding polypeptide according to any of the methods described above, such as by non-biological peptide synthesis, and conjugating the produced albumin binding polypeptide with a second and/or further moiety as defined in connection with the second aspect.

In one embodiment of a fusion protein or conjugate, there is moreover provided a fusion protein or conjugate as defined herein for use in therapy, e.g. for use as a medicament. Such a fusion protein or conjugate may exhibit a half-life in vivo which is longer than the half-life in vivo of the polypeptide having a desired biological activity per se. The fusion protein or conjugate may moreover elicit no or a reduced immune response upon administration to the mammal, such as a human, as compared to the immune response elicited upon administration to the mammal of the polypeptide having a desired biological activity per se. Alternatively speaking, this provides a method for decreasing the immunogenicity of a polypeptide having a desired biological activity, through the fusion or conjugation of such a polypeptide to an albumin binding polypeptide, fusion protein or conjugate according to aspects disclosed herein. In addition, this may enable enhancement of the biological activity of a second moiety.

In another embodiment, there is provided a fusion protein or conjugate according to the present disclosure, for use in diagnosis, e.g. for use as a diagnostic agent.

The present disclosure also concerns different aspects of using the above-described albumin binding polypeptide, as well as various methods for treatment, diagnosis and detection in which the polypeptide is useful due to its binding and other characteristics. When referring to the "albumin binding polypeptide" in the following description of these uses and methods, this term is intended to encompass the albumin binding polypeptide alone, but also all those molecules based on this polypeptide described above that e.g. incorporate the albumin binding polypeptide as a moiety in a fusion protein or conjugate, and/or are conjugated to a label, a chelator, a therapeutic and/or diagnostic agent and/or are provided with additional amino acid residues as a tag or for other purposes. As explained above, such fusion proteins, derivatives etc form a part of the present disclosure.

Another set of aspects concern the provision of new means to increase the solubility in aqueous solution of a poorly soluble compound, through conjugation thereof to an albumin binding polypeptide, fusion protein or conjugate. The ensuing complex of poorly soluble compound and an albumin binding polypeptide, alone or incorporated as a moiety in a fusion protein or conjugate, is able to associate with albumin in vivo or in vitro, which association increases the solubility in aqueous solution. Thus, in an embodiment of this further aspect, there is provided a composition, comprising a compound which per se has a solubility in water of no more than 100 µg/ml; coupled to an albumin binding polypeptide, a fusion protein or conjugate as described herein, wherein the compound and the albumin binding polypeptide, fusion protein or conjugate are covalently coupled.

In one embodiment, the compound per se has a solubility of no more than 10 µg/ml. In yet another embodiment, said solubility is no more than 1 µg/ml.

In some embodiments, the compound may be a pharmaceutically active compound, for example a cytotoxic agent. Non-limiting examples of cytotoxic agents are those selected from calicheamycin, auristatin, doxorubicin, maytansinoid, taxol, ecteinascidin, geldanamycin and their derivatives, and combinations thereof. Alternatively, the cytotoxic agent may be a synthetic chemotoxin made by organic synthesis and not derived from a naturally occurring compound.

In addition to the poorly soluble compound and albumin binding polypeptide, fusion protein or conjugate, the composition according to this aspect of the disclosure may, in some embodiments, also comprise a binding polypeptide with an affinity for a clinically relevant target. This binding polypeptide is suitably different from the albumin binding polypeptide, and may be non-covalently or covalently coupled to the other components of the inventive composition. As non-limiting examples, the binding polypeptide with an affinity for a clinically relevant target may be selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, other three helix domains, lipocalins, ankyrin repeat domains, cellulose binding domains, γ crystallines, green fluorescent protein, human cytotoxic T lymphocyte-associated antigen 4, protease inhibitors such as Kunitz domains, PDZ domains, SH3 domains, peptide aptamers, staphylococcal nuclease, tendamistats, fibronectin type III domain, transferrin, zinc fingers and conotoxins.

The composition according to the above aspect of the present disclosure has an ability to associate with albumin in vivo or in vitro, through the provision in the composition of an albumin binding polypeptide, by itself or as present in a fusion protein or conjugate. In certain cases, it may be of benefit to form a complex of the composition with albumin outside of a living organism, i.e. to add exogenous albumin to the composition. Such a composition may be lyophilized, providing a formulation that is suitable for storage at ambient temperature. Thus, the present disclosure also provides a composition as defined above which further comprises albumin, such as human serum albumin.

The present disclosure also provides the composition according to the above aspect for use as a medicament, i.e. for use in therapy, in cases where the compound is a therapeutically active compound. Suitably, the provision of an albumin binding polypeptide, fusion protein or conjugate and optionally albumin does not deleteriously affect the therapeutic efficacy of the active compound, so the inventive composition will be useful in those therapeutic or prophylactic settings where the compound per se is indicated.

In another embodiment, there is provided the composition according to the above aspect for use as a diagnostic agent, i.e. for use in diagnosis.

A related aspect of the present disclosure provides a method of preparation of a composition as described immediately above. The method comprises
  providing a compound which per se has a solubility in water of no more than 100 μg/ml; and
  covalently coupling the compound to an albumin binding polypeptide, fusion protein or conjugate according aspects as described herein, thus forming a composition comprising a covalent complex of compound and albumin binding polypeptide, fusion protein or conjugate.

In embodiments of the present disclosure where albumin is included into the composition, the method may comprise the additional step of mixing said complex of compound and albumin binding polypeptide, fusion protein or conjugate with albumin, thus forming a composition comprising a non-covalent complex of i) the covalent complex of compound and albumin binding polypeptide, fusion protein or conjugate, and ii) albumin. The relative proportions of the two components of this non-covalent complex may for example be 1:1, so that one unit of the complex of poorly soluble compound and albumin binding polypeptide, fusion protein or conjugate is associated with one molecule of albumin. In one embodiment, the method additionally comprises lyophilizing the non-covalent complex to obtain a lyophilized composition.

In another closely related aspect, the present disclosure provides a method of increasing the aqueous solubility of a compound, comprising providing a compound which per se has a solubility in water of no more than 100 μg/ml;
  covalently coupling the compound to an albumin binding polypeptide, fusion protein or conjugate according aspects as described herein, thus forming a covalent complex of compound and albumin binding polypeptide, fusion protein or conjugate; and mixing said complex of compound and albumin binding polypeptide, fusion protein or conjugate with albumin under conditions that promote the non-covalent association of the albumin binding polypeptide with albumin; whereby the solubility in water of the compound in said complex is greater than the solubility in water of the compound per se.

In these method aspects concerning the solubility of a poorly soluble compound, the optional features of the various components are as described in connection with the immediately preceding composition aspect.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated for carrying out this invention, but that the invention will include all embodiments falling within the scope of the appended claims.

FIGURES

FIG. 1A-1F is a listing of the amino acid sequences of examples of albumin binding polypeptides of the present disclosure (SEQ ID NO:1-152, SEQ ID NO:155-203), the GA3 domain from protein G of *Streptococcus* strain G148 extended by a N-terminal glycine residue (SEQ ID NO:153) and an albumin binding polypeptide derived from G148-GA3 as previously described by Jonsson et al (supra, SEQ ID NO:154).

Figure 3A:
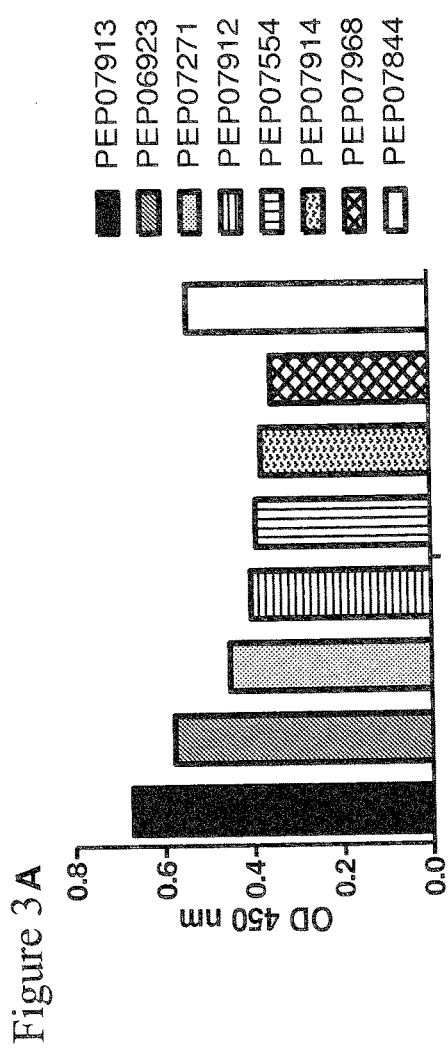
Figure 3B:
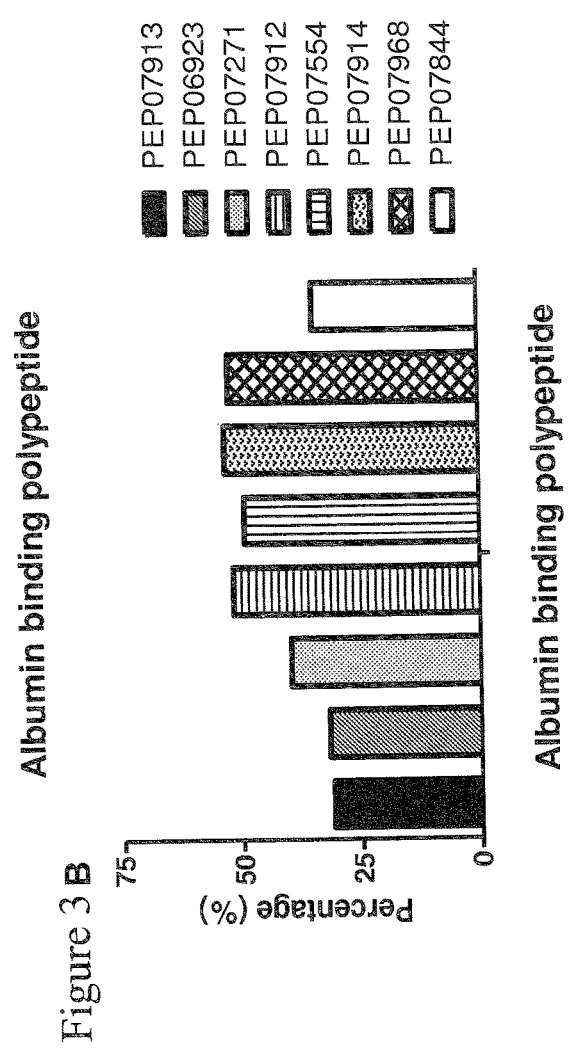
Figure 3C:
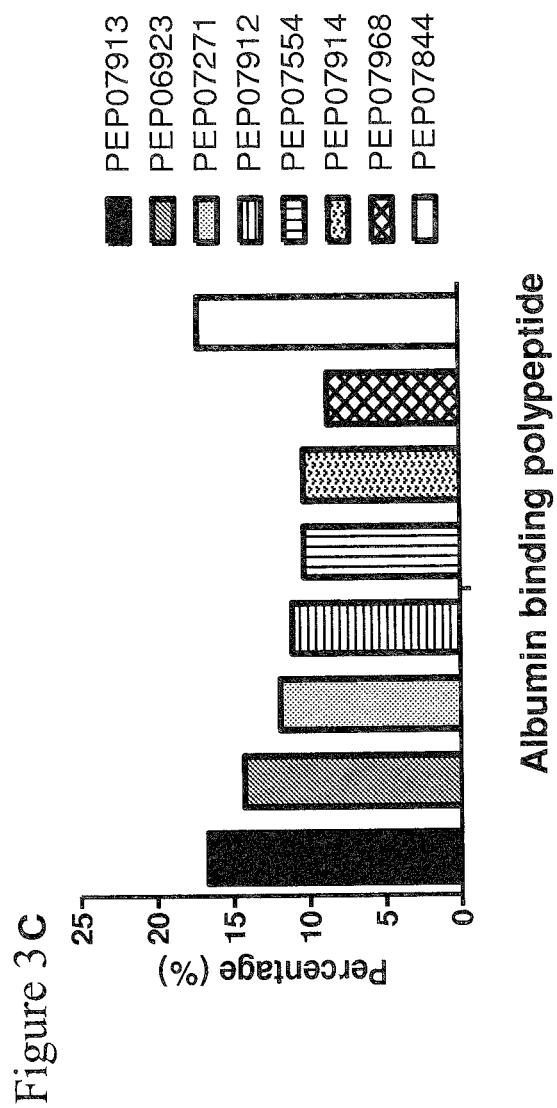

FIGS. 3A-C show the result of binding analysis performed by ELISA for investigating the binding of the albumin binding polypeptides PEP07913 (SEQ ID NO:153), PEP06923 (SEQ ID NO:154), PEP07271 (SEQ ID NO:155), PEP07912 (SEQ ID NO:157), PEP07554 (SEQ ID NO:156), PEP07914 (SEQ ID NO:158), PEP07968 (DOTA-conjugated PEP07911, SEQ ID NO:159) and PEP07844 (SEQ ID NO:161), to IgG molecules present in 126 individual normal human sera, where A) shows the average OD-value, B) shows the percentage of negative sera (defined as OD<0.15), and C) shows the percentage of positive sera (defined as OD>1.0).

Figures 4A, 4B:
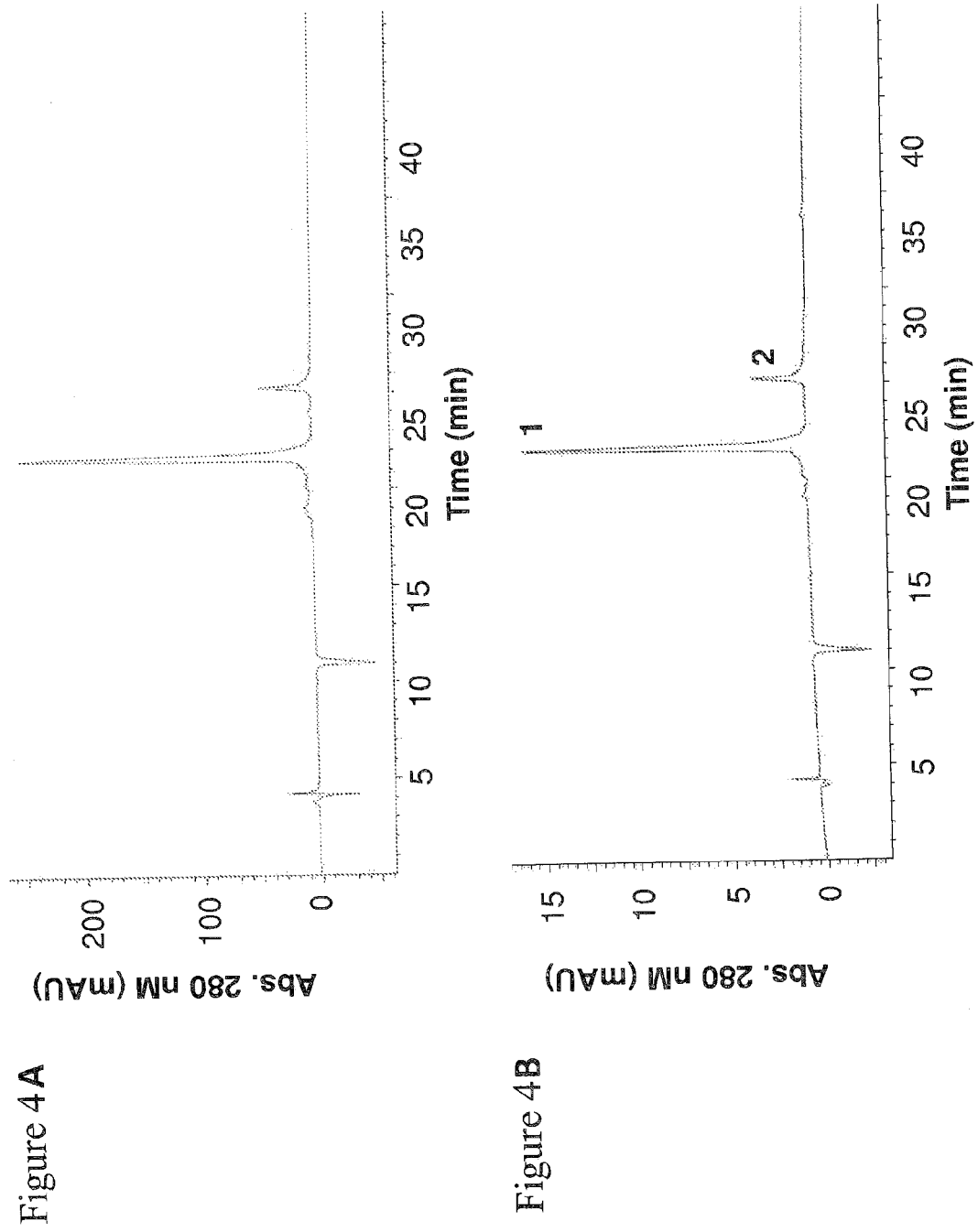

FIGS. 4A-B are chromatograms showing analysis of purified, chemically produced albumin binding polypeptide PEP07834 (SEQ ID NO:160), where A) shows the absorbance signal at 220 nm, blank subtracted, and B) shows the absorbance signal at 280 nm, blank subtracted. Two peaks appeared at both wavelengths.

Figure 5A:
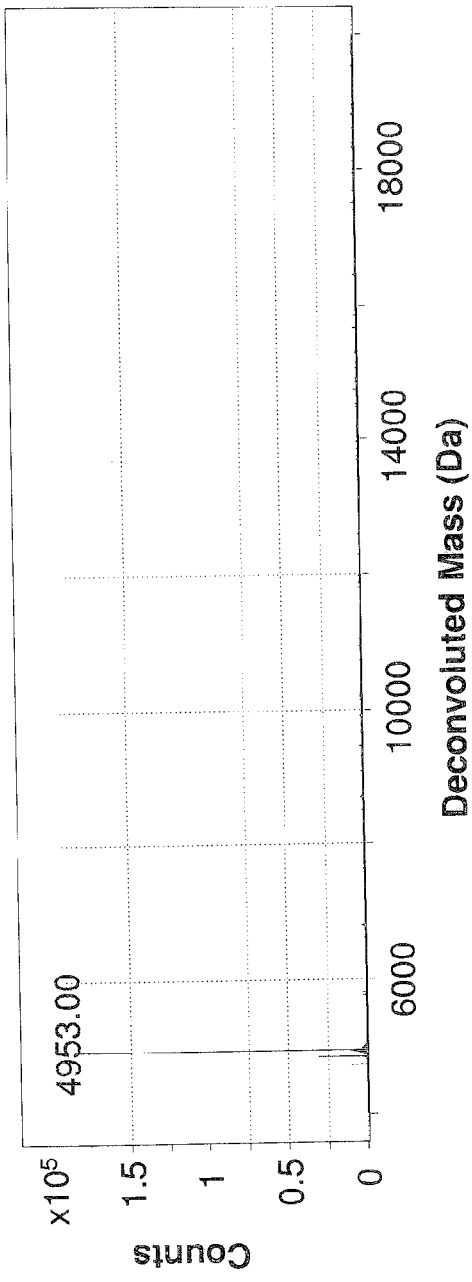
Figure 5B:
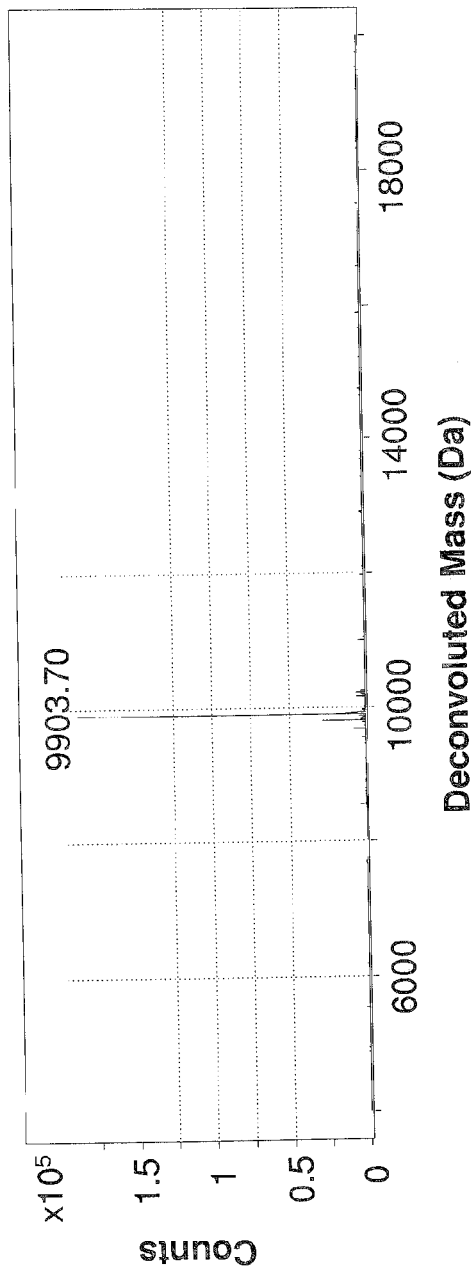

FIGS. 5A-B are spectrograms showing masspectrometric analysis of the two peaks identified in FIGS. 4A) and B). A) is the spectrogram of the first peak, i.e. the monomer of PEP07834 (SEQ ID NO:160), and B) is the spectrogram of the dimer of PEP07834.

Figure 6B:
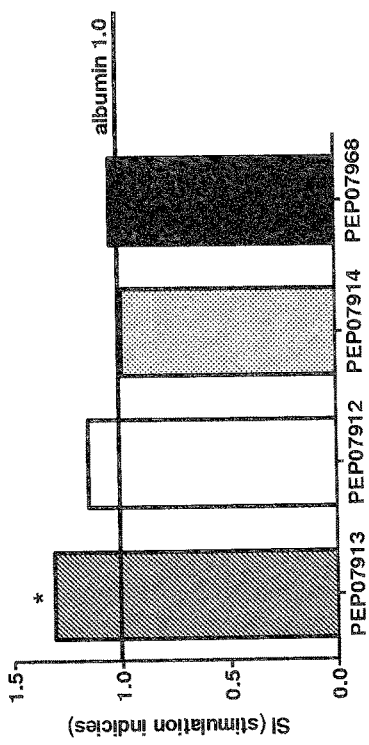
Figure 6A:
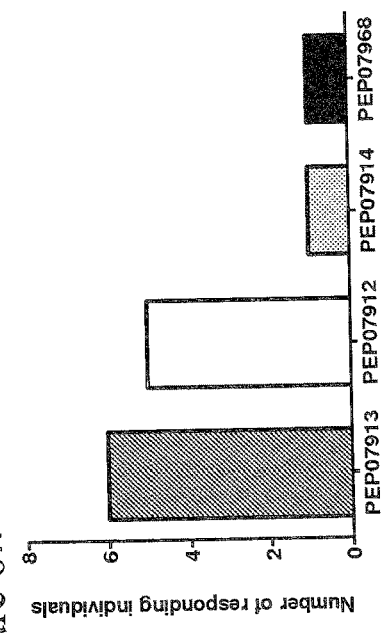
Figure 6C:
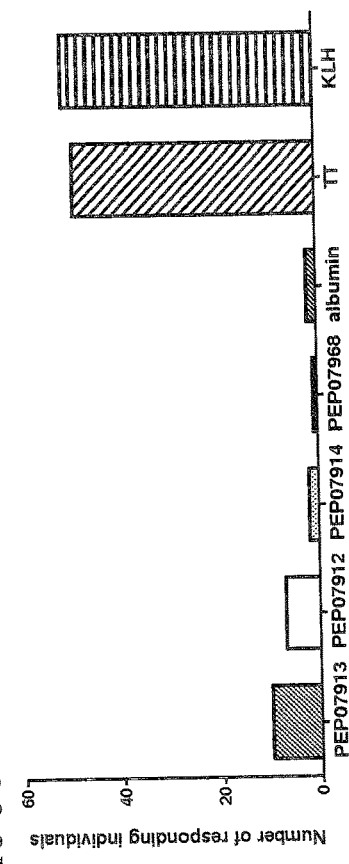

FIGS. 6A-C are diagrams showing an immunogenicity assessment of albumin binding polypeptides PEP07913 (SEQ ID NO:153), PEP07912 (SEQ ID NO:157), PEP07914 (SEQ ID NO:158) and PEP07968 (DOTA-conjugated PEP07911, SEQ ID NO:159) in a $CD3^+$ $CD4^+$ T cell proliferation assay. A) shows the number of individuals responding to the albumin binding polypeptides compared to recombinant human albumin in a cohort of 52 Caucasian donors. B) shows the average stimulation indices (SI) for PEP07913, PEP07912, PEP07914 and PEP07968 compared to the negative control containing recombinant human albumin. C) shows the number of responding individuals against all proteins in the study as compared to the buffer control.

Figure 7A:
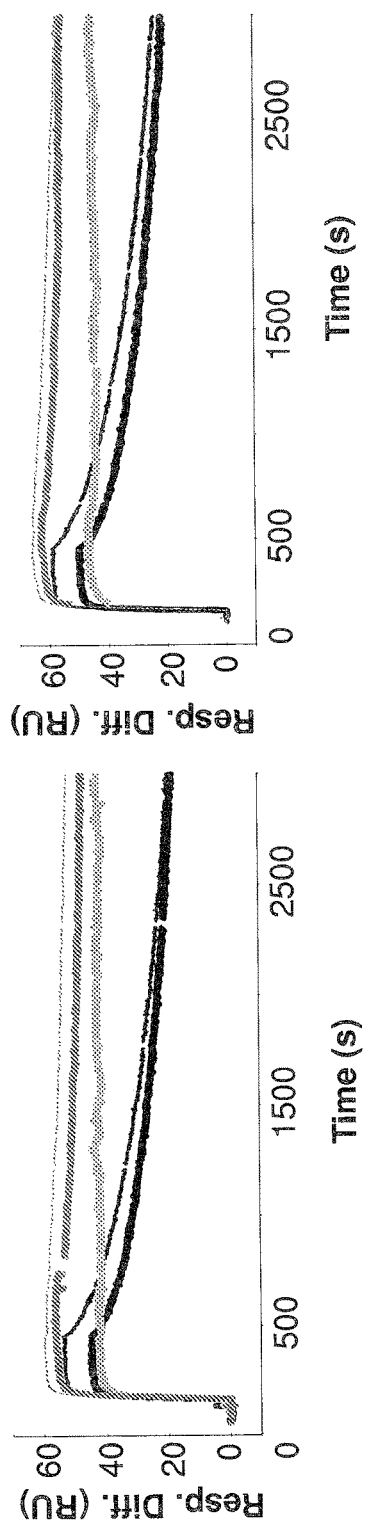
Figure 7B:
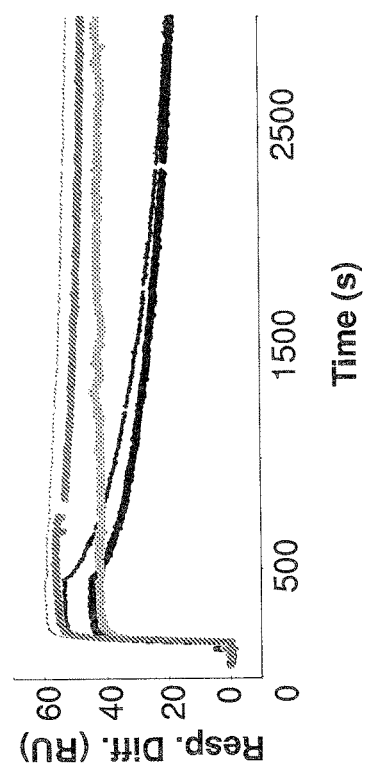
Figure 7C:
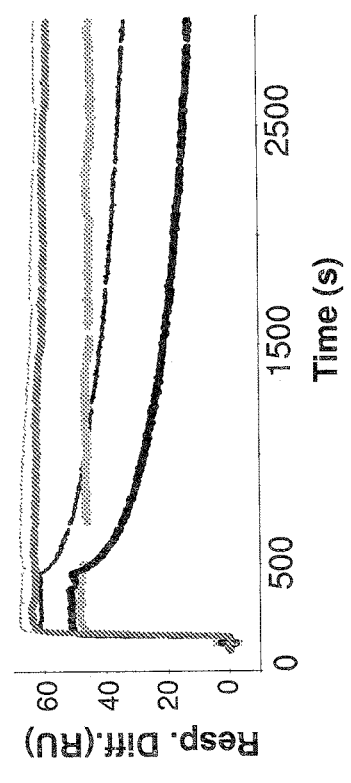

FIGS. 7A-C shows the result of binding analysis performed in a Biacore instrument for investigating the binding of the albumin binding polypeptides A) PEP07986 (SEQ ID NO:163), B) PEP08296 (DOTA-conjugated PEP08185, SEQ ID NO:148) and C) PEP06923 (SEQ ID NO:154) to albumin from different species. The sensorgrams shown correspond to protein injected at a concentration of 40 nM over surfaces immobilized with albumin from human (1130 RU), thin gray line; cynomolgus monkey (1046 RU), thick gray line; rat (831 RU), thick light gray line; dog (1053 RU), thin black line; and mouse (858 RU), thick black line.

Figure 8:
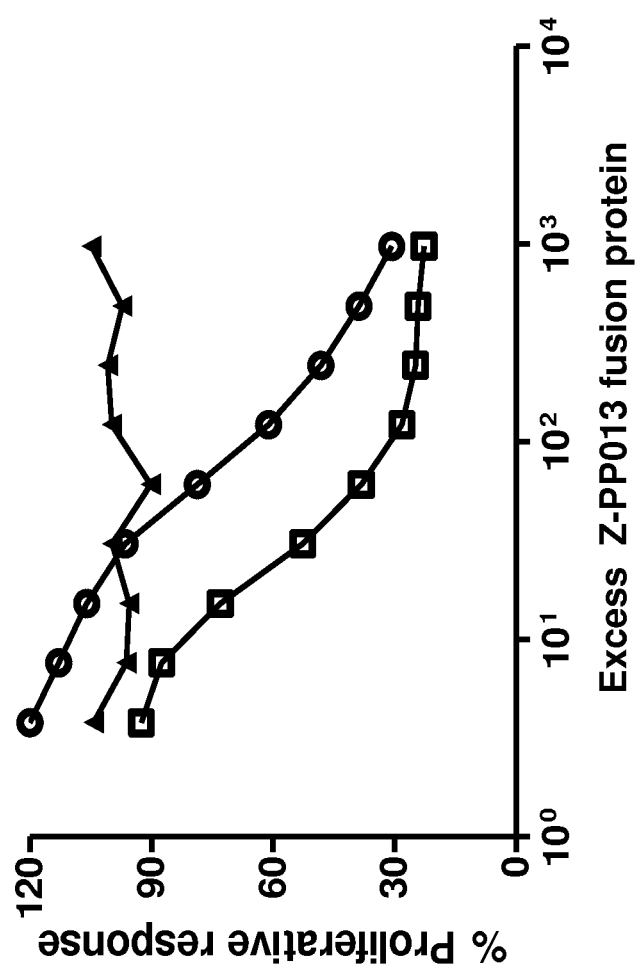

FIG. 8 shows the inhibitory effect of $Z_X$-PP013 (open circles), $Z_Y$-PP013 (open squares) and $Z_{neg}$-PP013 (closed triangles) on cytokine induced TF-1 cell proliferation in the presence of five times molar excess of HSA.

Figure 9:
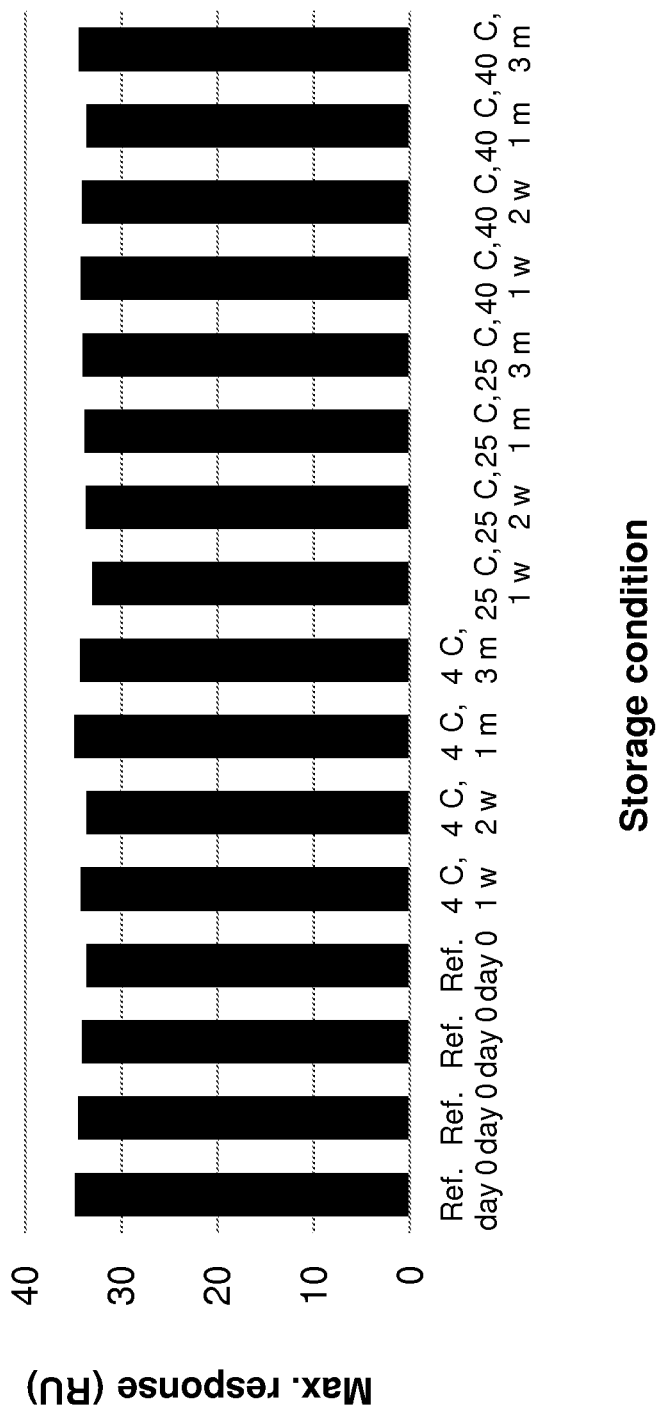

FIG. 9 shows the maximum binding responses obtained by Biacore analysis of PEP07986 (SEQ ID NO:163) stored at 4, 25 or 40° C. for one week, two weeks, one month and three months as indicated, at a concentration of 2 mg/ml, injected over immobilized HSA (704 RU) at a concentration of 10 nM. Non-treated samples from time=0 are shown as references.

Figure 10:
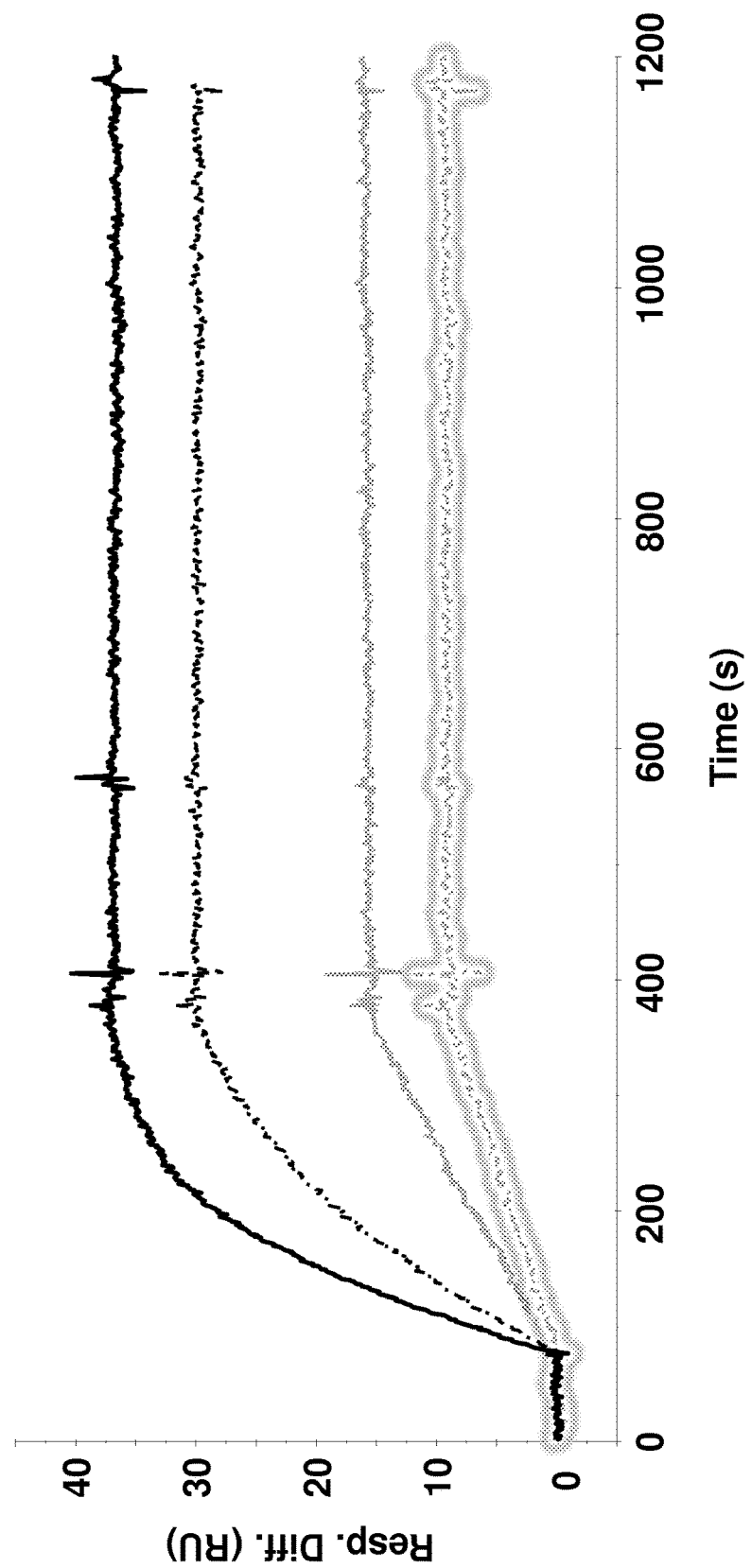

FIG. 10 shows the result of binding analysis performed in a Biacore instrument for investigating the binding of the albumin binding polypeptide PEP08296 (DOTA-conjugated PEP08185, SEQ ID NO:148) to human serum albumin before and after heat treatment. Two concentrations of PEP08296 (0.8 nM, grey lines; 4 nM, black lines) were injected over a surface with 724 RU of immobilized human serum albumin. Solid lines are before heat treatment and hatched lines after heat treatment for 10 minutes at 90° C.

Figure 11A:
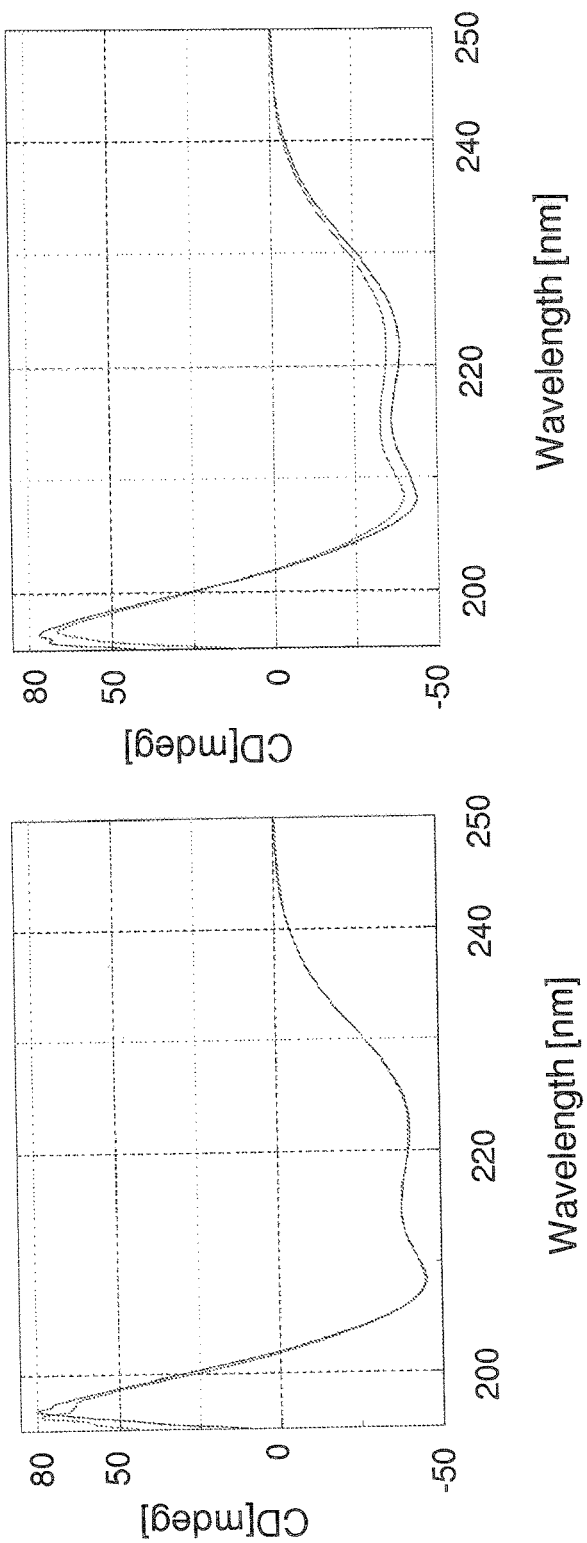
Figure 11B:
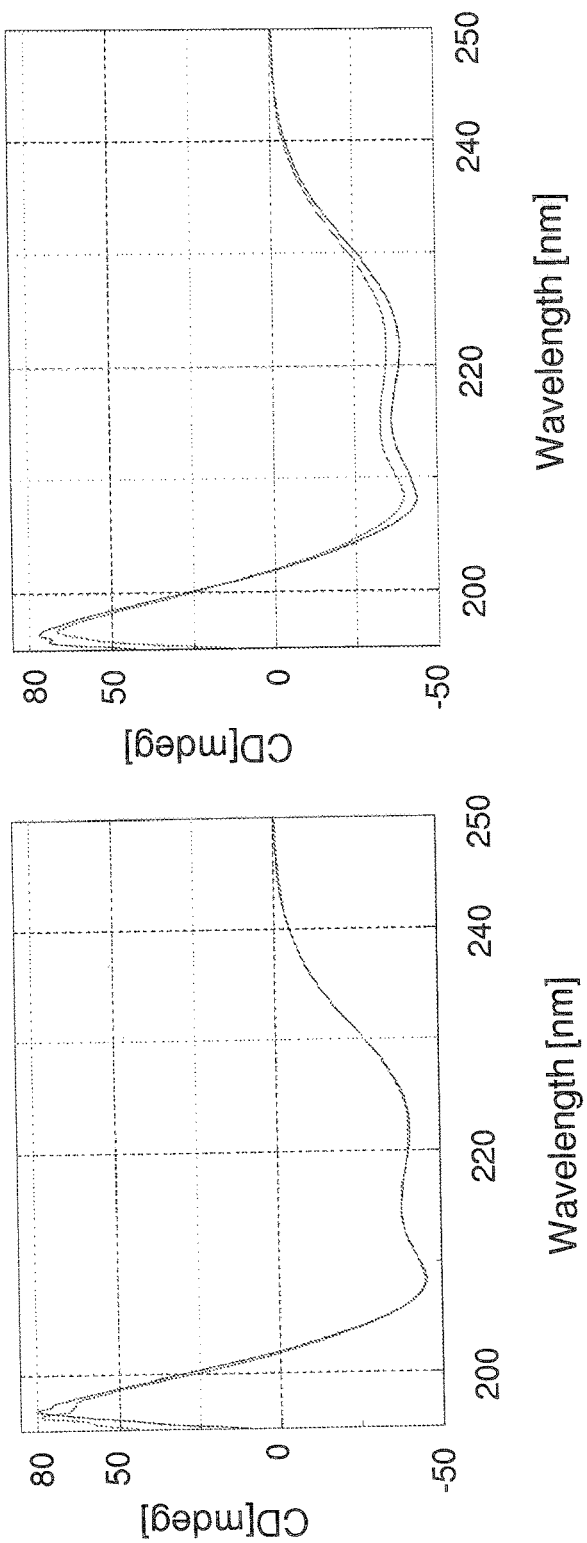

FIGS. 11A-B show the overlay of two CD spectra of PEP08296 (DOTA-conjugated PEP08185, SEQ ID NO:148) before and after heat treatment for 12 min at 90° C. A) Sample incubated in PBS pH 7.2. B) Sample incubated in PBS pH 4.0.

Figure 12:
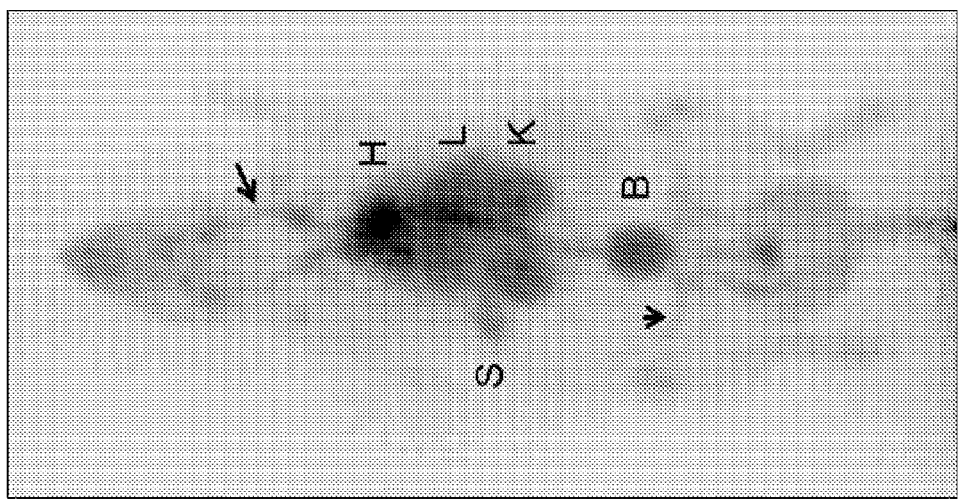

FIG. 12 shows the maximum intensity projection (MIP) image of the whole body distribution of $^{68}$Ga-PEP08296 in a healthy rat, summed during 1.5 h of data collection immediately following intravenous injection (tail vein). Circulating radioactivity in the major vessels (e.g. the jugular (long arrow) and femoral (short arrow)), the heart (H), liver (L), spleen (S), kidney (K) and bladder (B) are readily delineated.

Figure 13:
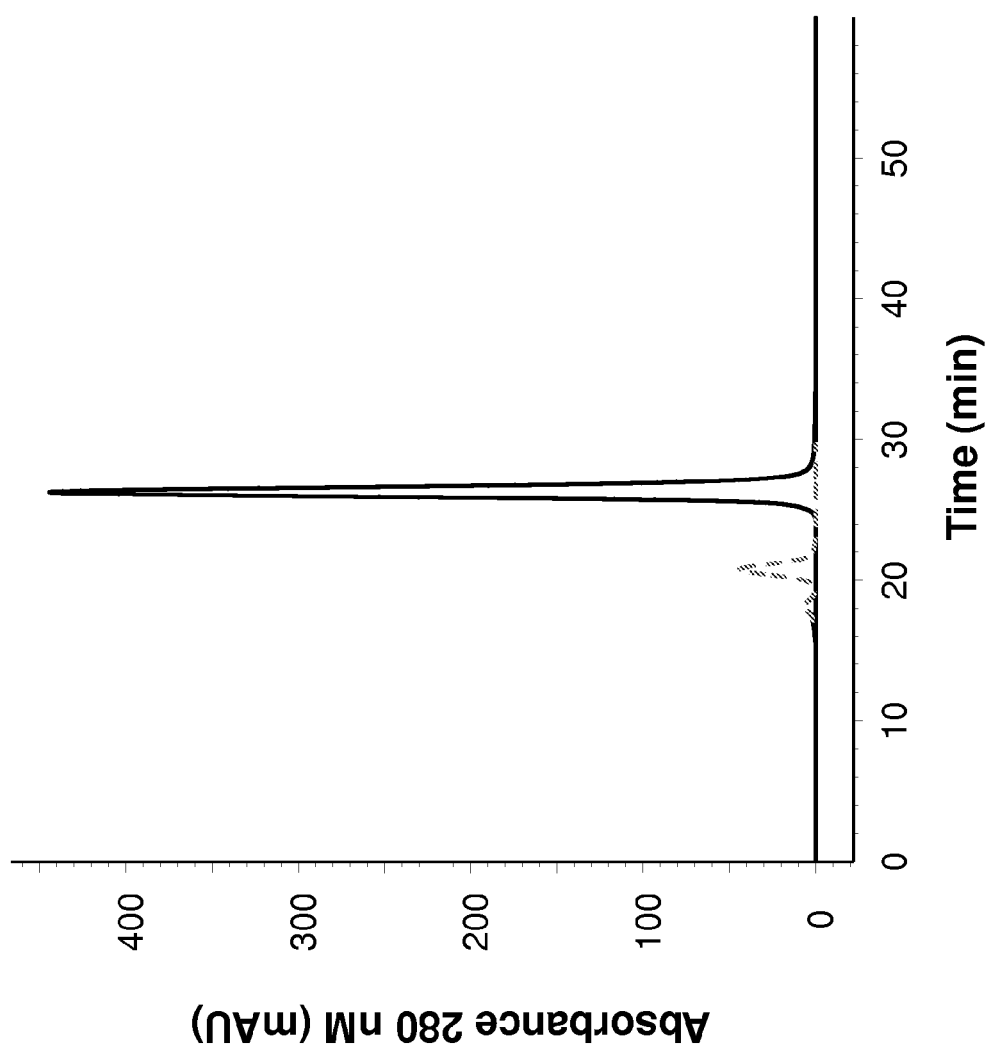

FIG. 13 shows a gel filtration chromatogram of PEP07986 (SEQ ID NO:163) injected at a concentration of 42 mg/ml, black solid line. A chromatogram of ovalbumin (Mw 43 kDa) injected at a concentration of 5 mg/ml, gray broken line, is included for comparison, confirming that the peak for PEP07986 is not an aggregate, which would have been expected in the void volume eluted at an earlier time point than ovalbumin.

The invention will now be illustrated further through the non-limiting description of experiments conducted in accordance therewith. Unless otherwise specified, conventional chemistry and molecular biology methods were used throughout.

EXAMPLES

Example 1

Cloning, Expression, Purification and Characterization of Albumin Binding Polypeptides In this example, ten different albumin binding polypeptides, PEP07913 (SEQ ID NO:153), PEP07912 (SEQ ID NO:157), PEP07914 (SEQ ID NO:158), PEP07968 (DOTA-conjugated PEP07911, SEQ ID NO:159), PEP06923 (SEQ ID NO:154), PEP07271 (SEQ ID NO:155), PEP07554 (SEQ ID NO:156), PEP07844 (SEQ ID NO:161), PEP07986 (SEQ ID NO:163) and PEP08296 (DOTA-conjugated PEP08185, SEQ ID NO:148), the amino acid sequences of which are set out in FIG. 1 and in the appended sequence listing, were cloned, purified and characterized.
Material and Methods
Cloning of Albumin Binding Polypeptide Variants Mutations in G148-GA3 were generated using site directed mutagenesis with the appropriate oligonucleotides to obtain the desired albumin binding polypeptide variants. The gene fragments were amplified by PCR with primers adding specific endonuclease sites as well as an N-terminal MGSS sequence preceding the albumin binding polypeptide variants. The fragments were cleaved with NdeI and NotI, purified and ligated to a cloning vector, the plasmid pAY02556 (containing an origin of replication from pBR322, a kanamycin resistance gene and a T7 promoter for expression of the gene of interest), restricted with the same enzymes. Ligations were transformed to electrocompetent E. coli TOP10 cells. The transformed cells were spread on TBAB plates (30 g/l tryptose blood agar base) supplemented with 50 µg/ml of kanamycin, followed by incubation at 37° C. overnight. The colonies were screened using PCR and sequencing of amplified fragments was performed using the biotinylated oligonucleotide and a BIGDYE Terminator v3.1 Cycle Sequencing Kit (Applied Biosystems), used in accordance with the manufacturer's protocol. The sequencing reactions were purified by binding to magnetic streptavidin coated beads using a Magnatrix 8000 (NorDiag AB), and analyzed on ABI PRISM 3100 Genetic Analyzer (PE Applied Biosystems). All albumin binding polypeptide variants were subcloned as monomers and the constructs encoded by the expression vectors were MGSS-[PP###], where PP### corresponds to the amino acid residues constituting the sequence of the albumin binding polypeptide.

In addition, the gene fragments of G148-GA3, PP007 (SEQ ID NO:7), PP013 (SEQ ID NO:13) and PP037 (SEQ ID NO:37) were amplified by PCR with primers adding specific endonuclease sites as well as a hexahistidin sequence, a TEV protease site and a glycine residue before the amino acid residues constituting the sequence of the albumin binding polypeptide. The polypeptides PEP07913 (SEQ ID NO:153), PEP07912 (SEQ ID NO:157), PEP07914 (SEQ ID NO:158) and PEP07968 (SEQ ID NO:159) correspond to the albumin binding polypeptides G148-GA3, PP007 (SEQ ID NO:7), PP013 (SEQ ID NO:13) and PP037 (SEQ ID NO:37) with glycine residues added. The fragments were cleaved with XbaI and NotI, purified and ligated to a cloning vector, the plasmid pAY02512 (containing an origin of replication from pBR322, a kanamycin resistance gene and a T7 promoter for expression of the gene of interest. The cloning site is preceded by a sequence encoding a peptide containing a hexahistidine tag followed by a cleavage site for the TEV protease), restricted with the same enzymes. Ligation, transformation and sequence verification were performed as described above. The four albumin binding polypeptide variants G148-GA3, PP007, PP013 and PP037 were subcloned as monomers and the constructs encoded by the expression vectors were MGSSHHHHHHLQSSGVDLGTENLYFQG-[PP###] (SEQ ID NO:205).

The expression vector encoding MGSSHHHHHHLQSSGVDLGTENLY-FQG-[PP013] (SEQ ID NO:206) was further modified by site directed mutagenesis using oligonucleotides, resulting in the insertion of a serine residue before the amino acid residues constituting the sequence of the albumin binding polypeptide, to obtain the construct MGSSHHHH-HHLQSSGVDLGTENLYFQ-GS-[PP013] (SEQ ID NO:207). This construct was further modified by 1) site directed mutagenesis to replace the serine residue at position 14 (within PP013) with a cysteine residue, generating MGSSHHHHHHLQSSGVDLGTENLYFQGS-[PP049] (SEQ ID NO:208), and 2) addition of a glycine residue C-terminally, generating MGSSHHHHHHLQSSGVDL-GTENLYFQGS-[PP049]-G (SEQ ID NO:209).

The addition of glycine C-terminally was accomplished by PCR amplification with primers including nucleotides encoding the glycine residue and specific endonuclease sites. The fragment was cleaved with Xba I and Not I, purified and ligated to a cloning vector, the plasmid pAY02641 (containing an origin of replication from pBR322, a kanamycin resistance gene and a T7 promoter for expression of the gene of interest), restricted with the same enzymes. Ligation, transformation and sequence verification were performed as described above.

Protein Expression

The albumin binding polypeptide variants were expressed in *E. coli* BL21 (DE3) either with an N-terminal MGSS-extension or with an N-terminal His$_6$-tag followed by a TEV-protease recognition site and a glycine residue. A colony of each albumin binding polypeptide variant was used to inoculate 4 ml TSB+YE medium supplemented with kanamycin to a concentration of 50 μg/ml. The cultures were grown at 37° C. for approximately 5 hours. 3 ml from each of the cultures was used to inoculate 800 ml TSB+YE supplemented with kanamycin to a concentration of 50 μg/ml in parallel bio reactors (Greta system, Belach Bioteknik AB). The cultivations were performed at 37° C., with aeration at 800 ml/minute and an agitation profile to keep dissolved oxygen levels above 30%, to an OD600 of 2, which was followed by addition of IPTG to a final concentration of 0.5 mM. Cultivation was continued for five hours after which the cultivation was cooled to 10° C., aeration was stopped and agitation lowered to 300 rpm. Cell pellets were harvested by centrifugation (15600×g, 4° C., 20 minutes) and stored at −20° C. until purification.

Purification of Albumin Binding Polypeptide Variants with a His$_6$-Tag and a TEV-Protease Site Frozen cell pellets harboring soluble hexahistidine-tagged polypeptides PEP07913 (SEQ ID NO:153), PEP07912 (SEQ ID NO:157), PEP07914 (SEQ ID NO:158), PEP07968 (SEQ ID NO:159), PEP07986 (SEQ ID NO:163) and PEP08185 (SEQ ID NO:148) were suspended in 35 ml binding buffer (20 mM sodium phosphate, 0.5 M NaCl, 20 mM imidazole, pH 7.4) with an addition of 1000 U BENZONASE (1.01654.001, Merck) and disrupted by ultrasonication. For each of the polypeptides, the ultrasonicated suspension was clarified by centrifugation (1 h, 37000×g, 4° C.) and the supernatant was loaded onto a His GRAVITRAP column (11-0033-99, GE Healthcare). The column was washed with 10 ml washing buffer (20 mM sodium phosphate, 0.5 M NaCl, 60 mM imidazole, pH 7.4), before eluting the polypeptide with 3 ml elution buffer (20 mM sodium phosphate, 0.5 M NaCl, 0.5 M imidazole, pH 7.4). The buffer was exchanged to a cleavage buffer (50 mM Tris-HCl, 150 mM NaCl, pH 8) using PD-10 desalting column (17-0851-01, GE Healthcare). The amount of polypeptide product was determined by measuring the absorbance at 280 nm before adding DTT to a final concentration of 5 mM. His$_6$-tagged TEV protease was added to the cleavage buffer at a 1:10 mass ratio relative to the polypeptide product. The cleavage was performed over night under slow mixing at 4° C. Imidazole was added to the cleavage mix, to a concentration of 20 mM, before loading the mix onto a His GRAVITRAP column (11-0033-99, GE Healthcare) for removing cleaved His$_6$-tags, His$_6$-tagged TEV protease and His$_6$-tagged uncleaved product.

For each variant, the flow-through, containing the albumin binding polypeptide variant, was further purified by reversed phase chromatography (RPC), as follows. The flow-through fraction was loaded on 1 ml Resource 15 RPC column (GE Healthcare), previously equilibrated with RPC A Buffer (0.1% TFA in water). After column wash with 10 column volumes (CV) RPC A Buffer, bound polypeptides were eluted with a linear gradient of 0-50% RPC B Buffer (0.1% TFA in acetonitrile) during 10 CV. The flow rate was 2 ml/min and the absorbance at 280 nm was monitored. Fractions containing albumin binding polypeptide variant were identified by SDS-PAGE analysis and pooled.

The RPC-purified albumin binding polypeptide variants were further purified by gel filtration on 120 ml Superdex 75 (GE Healthcare) packed in an XK16 column (GE Healthcare). The running buffer was 1×PBS, and the flow rate 2 ml/min. Fractions containing pure albumin binding polypeptide variant were pooled and concentrated to approximately 1.3 mg/ml. Finally, the concentrate was purified from trace amounts of remaining endotoxins by using 1 ml columns of AffinityPak Detoxi-Gel Endotoxin removing gel (Pierce, prod#20344), according to the manufacture's recommendations.

The albumin binding polypeptide variants PEP07911 and PEP08185 were conjugated with Mal-DOTA before the RPC-purification step, as follows. The buffer of the flow-through fraction from the IMAC-FT purification step was exchanged to 0.2 M NaAc, pH 5.5, using a disposable PD-10 desalting column (GE Healthcare). Maleimido-mono-amide-DOTA (Macrocyclics, cat. no. B-272) was added at 5-fold molar excess and incubated for 60 minutes at 30° C. under continuous shaking. The resulting polypeptide were denoted PEP07968 and PEP08296, respectively.

Purification of Albumin Binding Polypeptide-Variants Without His$_6$-Tag

Frozen cell pellets harboring soluble albumin binding polypeptide variants PEP06923 (SEQ ID NO:154), PEP07271 (SEQ ID NO:155), PEP07554 (SEQ ID NO:156) and PEP07844 (SEQ ID NO:161) were suspended in 20 mM Tris-HCl, pH 8 and disrupted by ultrasonication. For each of the polypeptide variants, the ultrasonicated suspension was clarified by centrifugation (30 min, 32000×g, 4° C.) and the supernatant was loaded onto a HSA-Sepharose column (GE Healthcare). After washing with TST-buffer (25 mM Tris-HCl, 1 mM EDTA, 200 mM NaCl, 0.05% Tween 20, pH 8.0), followed by 5 mM NH$_4$Ac, pH 5.5, bound albumin binding polypeptide variant was eluted with 0.5 M HAc, pH 3.2.

The albumin binding polypeptide variants were further purified by reversed phase chromatography (RPC), as follows. For each of the variants, the eluate from the HSA-affinity purification step was loaded on 1 ml Resource 15 RPC column (GE Healthcare), previously equilibrated with RPC A Buffer (0.1% TFA in water). After column wash with 10 CV RPC A Buffer, bound polypeptides were eluted with a linear gradient of 0-50% RPC B Buffer (0.1% TFA in acetonitrile) during 10 CV. The flow rate was 2 ml/min and the absorbance at 280 nm was monitored. Fractions containing pure albumin binding polypeptide variants were identified by SDS-PAGE analysis and pooled. Finally, the buffer was exchanged to 1×PBS (2.68 mM KCl, 137 mM NaCl, 1.47 mM KH$_2$PO$_4$, 8.1 mM Na$_2$HPO$_4$, pH 7.4) using a disposable PD-10 desalting column (GE Healthcare).

Characterization of Purified Albumin Binding Polypeptide-Variants

The concentration was assessed by measuring the absorbance at 280 nm using a NANODROP ND-1000 Spectrophotometer. The proteins were further analyzed with SDS-PAGE and LC-MS.

For the SDS-PAGE analysis, approximately 10 μg of each albumin binding polypeptide variant was mixed with NuPAGE LDS Sample Buffer (Invitrogen), incubated at 70° C. for 15 min and loaded onto NuPAGE 4-12% Bis-Tris Gels (Invitrogen). The gels were run with NuPAGE MES SDS Running Buffer (Invitrogen) in an XCell II SureLock Electrophoresis Cell (Novex) employing the Sharp Prestained Standard (Invitrogen) as molecular weight marker and using PhastGel BlueR (GE Healthcare) for staining.

To verify the identity of the albumin binding polypeptide variants, LC/MS analyses were performed using an Agilent 1100 LC/MSD system, equipped with API-ESI and a single quadruple mass analyzer. Approximately 10 μg of each of the purified albumin binding polypeptide variants was loaded on a Zorbax 300SB-C8 Narrow-Bore column (2.1× 150 mm, 3.5 μm, Agilent Technologies) at a flow-rate of 0.5 ml/min. Polypeptides were eluted using a linear gradient of 10-70% solution B for 15 min at 0.5 ml/min. The separation was performed at 30° C. The ion signal and the absorbance at 280 and 220 nm were monitored. The molecular weights of the purified albumin binding polypeptide variants were confirmed by MS.

Results

The expression levels of the albumin binding polypeptide variants were 10-30 mg product/g cell pellet, as estimated from SDS-PAGE analysis.

For all variants, the purity, as determined by SDS-PAGE analysis, exceeded 95% and the LC/MS analysis verified the correct molecular weights. After purification, between 1 and 8 mg of pure polypeptide was obtained for each of the ten albumin binding polypeptide variants.

Example 2

Affinity Determination for Albumin Binding Polypeptides

In this example, PEP06923 (SEQ ID NO:154), PEP07271 (SEQ ID NO:155), PEP07844 (SEQ ID NO:161), PEP07912 (SEQ ID NO:157), PEP07913 (SEQ ID NO:153), PEP07914 (SEQ ID NO:158) and PEP07968, (DOTA-conjugated PEP07911, SEQ ID NO:159), synthesized or expressed and purified in Example 1 were characterized for affinity to human serum albumin (HSA) using a Biacore instrument. PEP07913 corresponds to the amino acid sequence of G148-GA3 with addition of a N-terminal glycine residue, whereas PEP07271, PEP07844, PEP07912, PEP07914 and PEP07968 correspond to the albumin binding polypeptides of PP001 (SEQ ID NO:1), PP043 (SEQ ID NO:43), PP007 (SEQ ID NO:7), PP013 (SEQ ID NO:13) and PP037 (SEQ ID NO:37) with different N-terminal amino acid additions.

Material and Methods

Biosensor analysis on a Biacore2000 instrument (GE Healthcare) was performed with HSA (ALBUCULT, Novozymes), immobilized by amine coupling onto the carboxylated dextran layer of the surfaces of CM-5 chips (research grade; GE Healthcare) according to the manufacturer's recommendations. Surface 1 of the chip was activated and deactivated and used as a reference cell (blank surface) during injections, whereas surface 2 comprised HSA immobilized to 731 resonance units (RU) and surface 4 comprised HSA immobilized to 955 RU. The purified albumin binding polypeptide variants were diluted in running buffer HBS-EP (GE Healthcare) to 2.5 nM, 10 nM and 40 nM, and injected at a constant flow-rate of 50 μl/min for 5 minutes, followed by injection of HBS-EP for 60 minutes. The surfaces were regenerated with one injection of 25 μl HCl, 10 mM. The affinity measurements were performed in two sets; in the first set HBS-EP, PEP06923, PEP07271, PEP07912, PEP07913, PEP07914 and PEP07968 were injected (chip surface 2), and in the second set HBS-EP, PEP06923, PEP07844, PEP07912 and PEP07914 were injected (chip surface 4). PEP06923 was injected twice in each run as a control. The results were analyzed with a BIAEvaluation software (GE Healthcare). Curves of the blank surface were subtracted from the curves of the ligand surfaces.

Results

Figure 2:
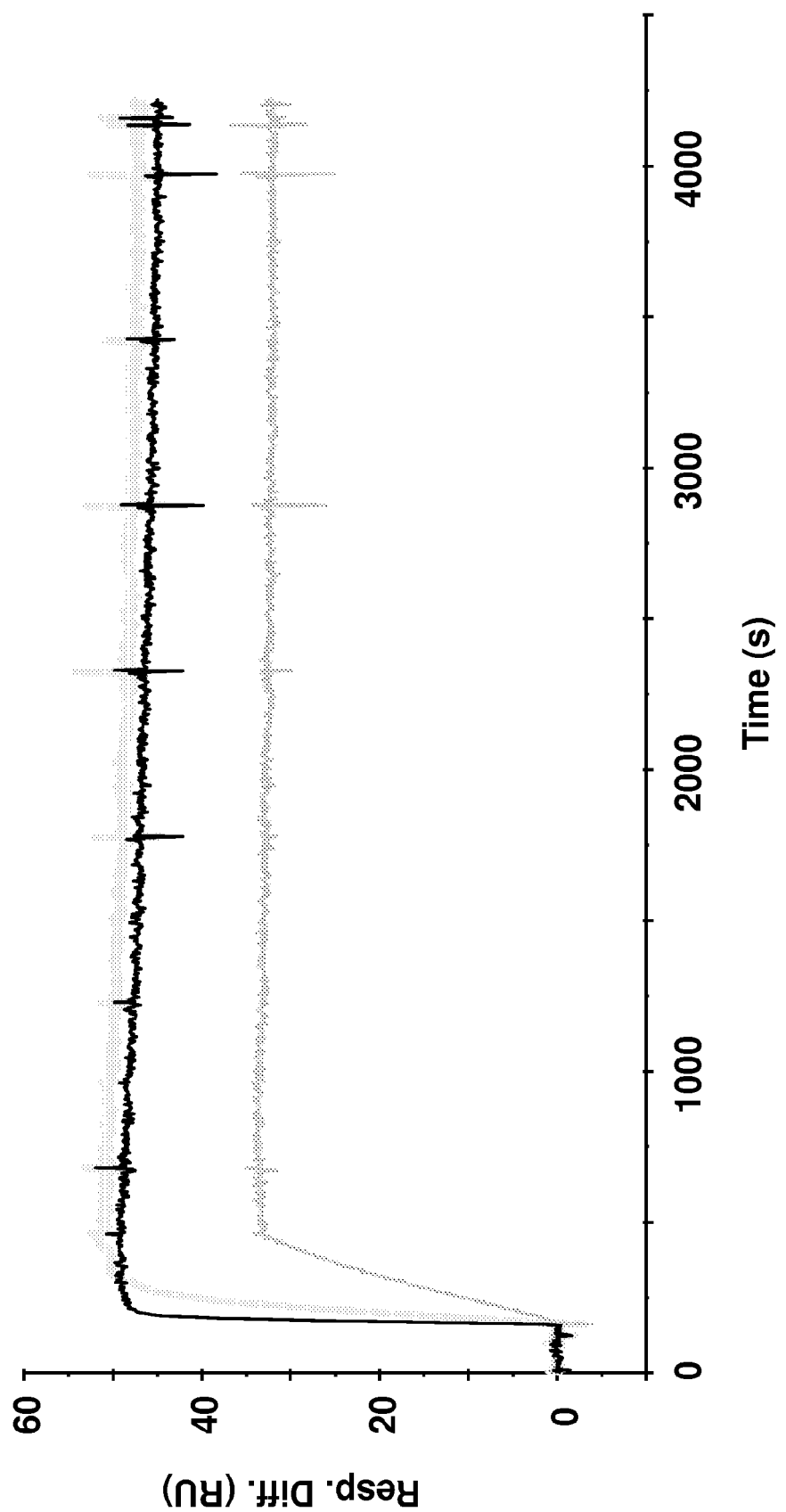
FIG. 2 shows the result of binding analysis performed in a Biacore instrument for investigating the binding of the albumin binding polypeptide PEP07912 (SEQ ID NO:157) to human serum albumin. Three different concentrations of purified protein (40 nM, fat gray line; 10 nM, black line; and 2.5 nM, gray line) were injected over a surface with 955 RU of immobilized human serum albumin.

The Biacore 2000 instrument has a technical limitation, hindering measurements of very high affinity. Hence, the purpose of the Biacore study was not to determine the exact kinetic parameters of the albumin binding polypeptide variants' affinity for HSA. However, the results provide a quantitative estimation of the relative affinities of these polypeptides for albumin. After subtraction of reference surface and buffer injection, curves were fitted to a 1:1 (Langmuir) binding model using BIAevaluation software with correction for mass transfer and with RUmax set as a local parameter. Curves are shown in FIG. 2. The relative $K_D$, $k_a$ ($k_{on}$) and $k_d$ ($k_{off}$) values were estimated and are presented in the Tables below.

TABLE 1

Kinetic parameters ($k_a$, $k_d$ and $K_D$) of albumin binding polypeptides to HSA, 1st set

|  | $k_a$ (Ms$^{-1}$) | $k_d$ (s$^{-1}$) | $K_D$ (M) |
|---|---|---|---|
| PEP07913 | 5.7 × 10$^5$ | 9.3 × 10$^{-4}$ | 1.6 × 10$^{-9}$ |
| PEP06923 (1) | 2.9 × 10$^7$ | 2.9 × 10$^{-5}$ | 9.9 × 10$^{-13}$ |
| PEP06923 (2) | 2.6 × 10$^7$ | 2.8 × 10$^{-5}$ | 1.1 × 10$^{-12}$ |
| PEP07271 | 3.9 × 10$^6$ | 2.9 × 10$^{-5}$ | 7.5 × 10$^{-12}$ |
| PEP07912 | 4.6 × 10$^6$ | 2.8 × 10$^{-5}$ | 6.2 × 10$^{-12}$ |
| PEP07914 | 3.5 × 10$^6$ | 2.5 × 10$^{-5}$ | 7.2 × 10$^{-12}$ |
| PEP07968 | 3.0 × 10$^6$ | 2.7 × 10$^{-5}$ | 9.0 × 10$^{-12}$ |

TABLE 2

Kinetic parameters ($k_a$, $k_d$ and $K_D$) of albumin binding polypeptides to HSA, 2nd set

|  | $k_a$ (Ms$^{-1}$) | $k_d$ (s$^{-1}$) | $K_D$ (M) |
|---|---|---|---|
| PEP06923 (1) | 2.0 × 10$^7$ | 2.6 × 10$^{-5}$ | 1.3 × 10$^{-12}$ |
| PEP06923 (2) | 2.1 × 10$^7$ | 2.5 × 10$^{-5}$ | 1.2 × 10$^{-12}$ |
| PEP07912 | 5.4 × 10$^6$ | 2.8 × 10$^{-5}$ | 5.2 × 10$^{-12}$ |
| PEP07914 | 3.8 × 10$^6$ | 2.6 × 10$^{-5}$ | 6.9 × 10$^{-12}$ |
| PEP07844 | 5.4 × 10$^6$ | 2.3 × 10$^{-5}$ | 4.4 × 10$^{-12}$ |

As shown in Tables 1 and 2, PEP07271 (SEQ ID NO:155), PEP07844 (SEQ ID NO:161), PEP07912 (SEQ ID NO:157), PEP07914 (SEQ ID NO:158) and PEP07968 (DOTA-conjugated PEP07911, SEQ ID NO:159) all seem to have approximately the same affinity for HSA, widely exceeding the affinity of the parent G148-GA3 (PEP07913; SEQ ID NO:153). The HSA affinity of these polypeptides is slightly lower compared to PEP06923 (SEQ ID NO:154), despite similar off-rate.

Example 3

Determination of Melting Temperature (Tm) for Albumin Binding Polypeptides

In this example, the albumin binding polypeptide variants PEP07913 (SEQ ID NO:153), PEP06923 (SEQ ID NO:154), PEP07271 (SEQ ID NO:155), PEP07554 (SEQ ID NO:156), PEP07912 (SEQ ID NO:157), PEP07914 (SEQ ID NO:158), PEP07968 (DOTA-conjugated PEP07911, SEQ ID NO:159), PEP07844 (SEQ ID NO:161) and PEP07986 (SEQ ID NO:163), expressed and purified as described in Example 1, and the albumin polypeptide variant PEP07975 (DOTA-conjugated PEP07834, SEQ ID NO:160), produced as described in Example 5, were analyzed by CD analysis. PEP07913 corresponds to the sequence of G148-GA3 having an N-terminal glycine residue, PEP06923 is an engineered high affinity derivative previously described by Jonsson et al, supra, whereas PEP07271, PEP07554, PEP07912, PEP07914, PEP07968, PEP07844 and PEP07975 are examples of the albumin binding polypeptides of PP001 (SEQ ID NO:1), PP007 (SEQ ID NO:7), PP013 (SEQ ID NO:13), PP037 (SEQ ID NO:37) and PP043 (SEQ ID NO:43) having different N-terminal amino acid additions according to the present disclosure.

Material and Methods

Purified albumin binding polypeptide variants were diluted in 1×PBS, to final concentrations between 0.4 and 0.5 mg/ml. Circular dichroism (CD) analysis was performed on a Jasco J-810 spectropolarimeter in a cell with an optical path-length of 1 mm. In the variable temperature measurements, the absorbance was measured at 221 nm from 20° C. to 90° C., with a temperature slope of 5° C./min.

Results

The melting temperatures (Tm) of the different albumin binding polypeptide variants were calculated by determining the midpoint of the transition in the CD vs. temperature plot. The results are summarized in Table 3 below.

TABLE 3

Determined Tm values of tested albumin binding polypeptide variants

| Variant | SEQ ID NO:# | N-terminal sequence[3] | Tm (° C.) |
|---|---|---|---|
| PEP07913 | SEQ ID NO: 153 | GL | 61 |
| PEP06923 | SEQ ID NO: 154 | GSSL | 57 |
| PEP07271 | SEQ ID NO: 155 | GSSL | 65 |
| PEP07554 | SEQ ID NO: 156 | GSSL | 58 |
| PEP07912 | SEQ ID NO: 157 | GL | 53 |
| PEP07914 | SEQ ID NO: 158 | GL | 59 |
| PEP07968 | SEQ ID NO: 159[1] | GL | 53 |
| PEP07975 | SEQ ID NO: 160[1, 2] | AL | 50 |
| PEP07844 | SEQ ID NO: 161 | GSSL | 65 |
| PEP07986 | SEQ ID NO: 163 | GSL | 61 |

[1]The peptide is conjugated with maleimide-DOTA at the cysteine
[2]The peptide is amidated at the C-terminus
[3]Leucine (underlined) is the residue in position 1 of the amino acid sequence of the albumin binding polypeptide as defined in the first aspect of the present disclosure The polypeptide PEP07968 is identical to PEP07912, except for the former having a cysteine residue in position 14 conjugated with maleimide DOTA, and the latter a serine residue. Thus, the DOTA modification should not affect the melting temperature. Also PEP07975 is conjugated with DOTA using $C_{14}$, and is identical to PEP07968 except for the C-terminal amide (resulting from the peptide synthesis in Example 5) and for having an N-terminal alanine instead of a glycine. Furthermore, comparing PEP07912 and PEP07554 reveals that an N-terminal serine gives a higher melting temperature than a glycine in the same position (5° C. difference in Tm). Thus, all albumin binding polypeptide variants according to the present disclosure show Tm above 55° C., except PEP07912 and DOTA-conjugated variants. Taking into consideration the importance of the N-terminal portion, all the tested albumin binding polypeptides are superior to the prior art derivative of Jonsson et al, i.e. PEP06923.

Example 4

Serum Response Analysis

The percentage of human serum containing IgG, capable of binding to a set of albumin binding polypeptides as disclosed herein was analyzed by ELISA. In total, 149 serum samples corresponding to 127 individuals were screened.

Material and Methods

ELISA plates (96-well, half area plates (Costar, cat. No. 3690)) were coated with 50 µl/well of ALBUCULT (Novozymes) diluted to 8 µg/ml in coating buffer (Sigma, cat. No. 3041). The plates were coated over night for three days at 4° C. On the day of analysis, the plates were washed twice with tap water and blocked for 2 hours with 100 µl of phosphate buffered saline (PBS) containing 0.05% casein (PBSC). The plates were emptied and 50 µl/well of the albumin binding polypeptides PEP07913 (SEQ ID NO:153), PEP06923 (SEQ ID NO:154), PEP07271 (SEQ ID NO:155), PEP07912 (SEQ ID NO:157), PEP07554 (SEQ ID NO:156), PEP07914 (SEQ ID NO:158), PEP07968 (DOTA-conjugated PEP07911, SEQ ID NO:159) and PEP07844 (SEQ ID NO:161), diluted to 2 µg/ml in PBSC were added according to a pre-made plate layout. After incubation for two hours at room temperature (RT), the plates were washed in PBSC four times using an automated ELISA washer. The 149 serum samples from 129 individuals were diluted 50 times in PBSC by adding 24 µl serum to 1174 µl PBSC. 50 µl of the diluted sera was added per well according to the pre-made plate layout. Each serum sample was tested as a singlet. Positive and negative controls were included on each plate and for each albumin binding polypeptide. Albumin binding antibodies (50 µl, 0.5 µl/ml immunoglobulin solution prepared in house from sera from primates immunized with PEP06923 (SEQ ID NO: 154)) was added as a positive control and 50 µl PBSC was used as a negative control. The plates were incubated for one hour at RT and subsequently washed four times in PBSC using an automated ELISA washer. The bound IgG was detected with 50 µl/well of anti-human IgG (Southern Biotech, cat no 2040-05) diluted 10 000 times in PBSC. After washing four times in PBSC using an automated ELISA washer, 50 µl/well of substrate was added (Pierce cat. No. 34021). The reaction was stopped after 10-15 minutes by the addition of 50 µl $H_2SO_4$ to each well, prior to measuring the absorbance using a multi-well plate reader (Victor3, Perkin Elmer).

Results

Of the 149 sera screened for IgG binding to the albumin binding polypeptides, 23 were negative for all eight polypeptides (OD-value<0.1), i.e. showed no IgG bound to the polypeptides. The analysis was performed with the 126 sera that were positive for one or more albumin binding polypeptides. The average absorbance was calculated (FIG. 3A) and the percentage of sera with OD-values values either <0.15 (FIG. 3B) or >1.0 (FIG. 3C). The highest average OD-value and the highest percentage of serum with IgG binding were obtained with PEP07913 (SEQ ID NO:153), PEP06923 (SEQ ID NO:154) and PEP07844 (SEQ ID NO:161), whereas least reactivity was found against PEP07968 (DOTA-conjugated PEP07911, SEQ ID NO:159), PEP07914 (SEQ ID NO:158) and PEP07554 (SEQ ID NO:156).

Thus, the most reactive albumin binding polypeptides were the parental G148-GA3 (PEP07913, SEQ ID NO:153) and the previously affinity improved derivative (PEP06923, SEQ ID NO:154), having helix 1 retained from G148-GA3. The third of the more reactive polypeptides (PEP07844, SEQ ID NO:161) contains the original lysine in position 14 in helix 1. This residue is intended for conjugation, and will therefore not be exposed in the final context. The identical albumin binding polypeptide variant, except for having an alanine in position 14 (PEP07554, SEQ ID NO:156), is one of the least reactive.

Example 5

Chemical Synthesis of a DOTA-Conjugated Albumin Binding Polypeptide

Material and Methods

The albumin binding polypeptide PEP07834 (SEQ ID NO:160) was synthesized by solid phase peptide synthesis (SPPS, as described by Quibell, M. & Johnson, T., in Fmoc Solid Phase Peptide Synthesis-A Practical Approach, W. C. Chan, P. D. White Eds, Oxford University Press 2000, 115-135) in a 433 A Peptide Synthesizer reactor (Applied Biosystems, Foster City, Calif.) on a 0.1 mmol scale, i.e. with a theoretical possible yield of 0.1 mmol peptide, using standard Fmoc chemistry. An acid-labile Fmoc amide resin was used as solid support throughout the synthesis (Rink Amide MBHA Resin LL (100-200 mesh), loading 0.39 mmol amide/g resin (Novabiochem)).

47 amino acid residues according to the sequence below were coupled to the amide resin by acylation reactions in the reactor for 10 minutes at room temperature (RT) and mixing. The acylation reactions were performed with a ten-fold molecular excess of Fmoc protected amino acids in NMP (N-methylpyrrolidone, Merck), activated with 1 eq of 2-(1H-benzotriazole-1-yl)-1,1,3,3-tetramethylaminium hexafluorophosphate (HBTU, IRIS Biotech), 1 eq of 1-hydroxybenzotriazole (HOBt, IRIS Biotech) and 2 eq of diisopropylethylamine (DIEA, Applied Biosystems). In addition, all reactive amino acid side chains were protected with standard side chain protection groups (tert-butyl (tBu) for Asp, Glu, Ser, Thr and Tyr, tert-butyloxycarbonyl (Boc) for Lys, 2,2,4,6,7-pentamethyldihydrobenzofuran-5-sulfonyl (Pbf) for Arg, and trityl (Trt) for Asn and Cys) prior to activation and coupling. In order to diminish the amount of incomplete couplings leading to truncated peptides, a minor amount of selected amino acid residues were subjected to coupling by acylation twice, without Fmoc deprotection as described below between the first and second coupling. The amino acid sequence of the synthesized albumin binding polypeptide PEP07834 was ALASAKEAA<u>N</u> AELD C<u>Y</u>GVSD F<u>YKRLI</u>DKAK TVEGVEALKD A<u>I</u>LAALP-NH$_2$ (SEQ ID NO:160-NH$_2$).

The underlined amino acid residues were double coupled. Any remaining unreacted amino groups on the resin bound peptides were capped with acetic anhydride (0.5 M acetic anhydride (AlfaAesar), 0.125 M DIEA, 0.015 M HOBt in NMP) for 5 min. Following every coupling, deprotection of the N-terminal Fmoc group on the resin bound peptides were performed by treatment with 20% piperidine (Sigma-Aldrich) in NMP for 10 min.

After completed synthesis, the peptides were cleaved from the solid support and simultaneously the side chain protection groups were cleaved off by treatment with TFA/EDT/H$_2$O/TIS (94:2.5:2.5:1) (TFA: trifluoroacetic acid (Apollo), EDT: 1,2-ethanedithiol (Aldrich), TIS: triisopropylsilane (Aldrich)) at RT for 2 h with occasional mixing. After TFA treatment, the peptides were extracted three times using 20% acetonitrile (Merck) in water and tert-butyl methyl ether (Merck). The aqueous phases were combined, filtered and lyophilized.

The crude peptides were analyzed and purified by semi-preparative RP-HPLC (Reprosil GOLD C18 300, 250*10 mm, 5 µm particle size) and a gradient of 32-55% B (A: 0.1% TFA-H$_2$O; B: 0.1% TFA-CH$_3$CN) during 25 min at a flow rate of 2.5 ml min$^{-1}$, followed by lyophilization.

The synthetic yield was determined by calculation of the integrated areas under the peaks from the 220 nm signal from the crude analysis on RP-HPLC. The correct molecular weight was verified using liquid chromatography electrospray ionization mass spectrometry (LC-ESI-MS) on a 6520 Accurate Mass Q-TOF LC/MS (Agilent Technologies). The purity of the product was verified using RP-HPLC (Reprosil GOLD C18 300, 250*4.6 mm, 3 µm particle size) using a gradient of 35-55% B over 25 min at a flow rate of 1.0 ml min$^{-1}$.

DOTA Conjugation 3 mg of PEP07834-amide (SEQ ID NO:160-amide) was reduced with 20 mM DTT at 40° C. for 30 minutes. Excess DTT was removed by buffer exchange on a PD-10 column (GE Healthcare) to 0.2 M ammonium acetate, pH 5.5. The coupling was performed with a 5-fold molar excess of chelator, maleimido-mono-amide-DOTA (Macrocyclics, Cat. No. B-272) solution in water (1 mg/ml). The mixture was incubated for 1 hour at 30° C. under continuous shaking. Purification from non-conjugated chelators was made on a semi-preparative RPC column (Zorbax 300SB C18, 9.4×250 mm, 5 µm). The coupling degree of the purified material was analyzed by HPLC-MS on a Zorbax 300SB C8 150×2.1 mm, 3.5 µm analytical column. Only maleimide-DOTA-conjugated PEP07834, denoted PEP07975, was detected by the method.

Results

Based on the elution profile of the crude material, the synthetic yield of the albumin binding polypeptide PEP07834-amide (SEQ ID NO:160-amide) was determined to be 8%. The found molecular weight was 4952.9 Da, which is in good agreement with the theoretical molecular weight calculated to 4952.6 Da. When analyzing the purified product, approximately 10-15% of the protein was found to be a disulfide linked homodimer (FIGS. 4 and 5). The binding activity of the DOTA-conjugated peptide (PEP07975) was confirmed as described in Example 2 (data not shown), and the melting temperature determined as described in Example 3.

Example 6

Immunogenicity Testing of Albumin Binding Polypeptides

PEP07913 (SEQ ID NO:153), PEP07912 (SEQ ID NO:157), PEP07914 (SEQ ID NO:158), and PEP07968 (DOTA-conjugated PEP07911, SEQ ID NO:159) were screened for their ability to induce T cell proliferation in peripheral blood mononuclear cells (PBMC) from 52 human Caucasian individuals (obtained from CRI-Labo Medische Analyse, Gent, Belgium). PEP07913 corresponds to the sequence of G148-GA3 having an N-terminal glycine residue, whereas PEP07912, PEP07914 and PEP07968 are examples of the albumin binding polypeptides of PP007 (SEQ ID NO:7), PP013 (SEQ ID NO:13) and PP037 (SEQ ID NO:37) having different N-terminal amino acid additions according to the present disclosure.

Materials and Methods

PBMCs, prepared according to standard cell biological methods, were added to a tissue culture (TC) treated 96-well round bottom plate (Falcon) in an amount of 300 000 PBMCs/well. The cells were stimulated by addition of 100 µl/well of albumin binding polypeptides PEP07913, PEP07912, PEP07914 and PEP07968 in AIMV medium (Invitrogen) additionally containing 900 µg/ml (3-fold molar excess) of recombinant human albumin (ALBUCULT, Novozymes). This corresponded to a final concentration of albumin binding polypeptide of 30 µg/ml. The stimulation was done in eight-plicates, i.e. the same albumin binding polypeptide were added to eight wells in identical amounts and under the same conditions. In positive control wells, the cells were stimulated with either 30 µg/ml Keyhole Limpet Hemocyanin (KLH, Calbiochem) or 30 µg/ml tetanus toxoid (TT, Statens Serum Institut). In negative control wells, only AIMV medium with or without 900 µg/ml of albumin were added.

Cell proliferation was assessed after seven days of culturing using Alexa Fluor 488 Click-iT EdU flow cytometry assay kit (Invitrogen). 1 µM/well of EdU incorporation marker was added on day six. On day seven, cells were washed, dissociated from the plate, washed again and stained for 30 minutes with anti-CD3-PerCP reagent (Becton Dickinson) and anti-CD4-Alexa647 reagent (Becton Dickinson). Following staining, the cells were washed, fixed (BD cellfix, BD biosciences), permeabilized (using saponin) and stained for EdU by addition of Click-iT reagent according to the manufacturer's protocol (Invitrogen). After completed staining, cells were washed again and analyzed using flow cytometry (FACSCantoII, BD Biosciences). To assess the number of proliferating cells, a fixed number of fluospheres (Invitrogen) was added to each well before analysis. All staining procedures and washes were performed directly in the 96-well plate.

The raw FACSCantoII data were gated hierarchically on $CD3^+$ $CD4^+$ T cells and the number of gated cells as well as their fluorescence intensity of EdU-Alexa Flour 488 incorporation marker were recorded. The mean values of the number of proliferating cells/eight-plicate of protein treated wells were compared to the positive and negative controls and the resulting ratios, described as stimulation indices (SI), were calculated. Based on the SI and the variation between replicates, threshold SI-values were set to 2.0 and 0.5 for stimulation and inhibition, respectively.

Results

The albumin binding polypeptides PEP07913, PEP07912, PEP07914 and PEP07968 were assessed for their immunogenic potential in the presence of 3-fold excess of recombinant human albumin in a target human population using an in vitro PBMC proliferation assay. Compared to the albumin control, PEP07913 induced $CD3^+$ $CD4^+$ T cells proliferation in 6 of 52 donors, PEP07912 in 5 of 52 donors and PEP07914 and PEP07968 in 1 of 52 donors (FIG. 6A).

The mean stimulation index (SI) for all 52 donors was not significantly different for PEP07914 and PEP07968 compared to the negative control containing recombinant human albumin (p=0.79 and 0.48 respectively, FIG. 6B). The SI for PEP07913 was significantly higher (p=0.002) whereas the SI for PEP07912 was higher but not significant (p=0.03, FIG. 6B).

As compared to buffer only, the number of responding individuals was 10 for PEP07912, 7 for PEP07912, 2 for PEP07914, 1 for PEP07968, 2 for recombinant human albumin, and 49 and 51 for the two positive controls TT and KLH, respectively (FIG. 6C). The albumin binding polypeptides were ranked according to their immunogenicity in the following order: PEP07913>PEP07912>PEP07914>PEP07968. Both PEP07914 and PEP07968 were defined as non-immunogenic. The above results thus demonstrate that the immunogenic potential of the albumin binding polypeptides of the present disclosure is low, as compared to the positive controls.

Example 7

Albumin Binding Polypeptides' Affinity to Albumin from Different Species

In this example, PEP06923 (SEQ ID NO:154), PEP07986 (SEQ ID NO:163) and PEP08296, (DOTA-conjugated PEP08185, SEQ ID NO:148), expressed and purified as described in Example 1, were characterized for affinity to albumin from human (HSA), cynomolgus monkey (CSA), rat (RSA), mouse (MSA) and dog (DSA) using a Biacore instrument.

Material and Methods

Biosensor analysis on a Biacore2000 instrument (GE Healthcare) was performed with HSA (ALBUCULT, Novozymes), CSA (purified in-house from cynomolgus serum), RSA (Sigma-Aldrich, Cat. No. A6272), MSA (Sigma-Aldrich, Cat. No. A3559) and DSA (MP Biomedicals, Cat. No. 55925), immobilized by amine coupling onto the carboxylated dextran layer of the surfaces of CM-5 chips (research grade; GE Healthcare) according to the manufacturer's recommendations.

On chip 1, surface 1 was activated and deactivated and used as a reference cell (blank surface) during injections, whereas surface 2 comprised HSA immobilized to 1130 resonance units (RU), surface 3 comprised CSA immobilized to 1046 RU, surface 4 comprised RSA immobilized to 831 RU. On chip 2, surface 1 was used as blank surface, whereas surface 3 comprised MSA immobilized to 858 RU. On chip 3, surface 1 was used as blank surface, whereas surface 2 comprised DSA immobilized to 1053 RU. For analysis of affinity for HSA, CSA, and RSA (chip 1), the purified albumin binding polypeptide variants were diluted in running buffer HBS-EP (GE Healthcare) to 40 nM, 10 nM and 2.5 nM; for analysis of affinity for MSA (chip 2) the albumin binding polypeptide variants were diluted to 1280 nM, 640 nM, 160 nM and 40 nM and for analysis of affinity for DSA (chip 3) albumin binding polypeptide variants were diluted to 1280 nM, 640 nM, 160 nM, 40 nM and 10 nM. The albumin binding polypeptides were injected at a constant flow-rate of 50 µl/min for 5 minutes, followed by injection of HBS-EP for 60 minutes. The surfaces were regenerated with one injection of 25 µl HCl, 10 mM. All samples were run in duplicates.

The results were analyzed with a BIAevaluation software (GE Healthcare). Curves of the blank surface were subtracted from the curves of the ligand surfaces.

Results

The Biacore 2000 instrument has a technical limitation, hindering measurements of very high affinity. Hence, the purpose of the Biacore study was not to determine the exact kinetic parameters of the albumin binding polypeptide variants' affinity for HSA, CSA, RSA, MSA and DSA respectively. However, the results provide a quantitative estimation of the relative affinities of the enclosed polypeptides for albumin from these different species. After subtraction of reference surface and buffer injection, curves were fitted to a 1:1 (Langmuir) binding model using BIAevaluation software with correction for mass transfer and with RUmax set as a local parameter. Representative binding curves are shown in FIG. 7.

PEP07986 and PEP08296 (DOTA-conjugated PEP08185) bind with high affinity ($K_D$ in the range from below picomolar to below nanomolar) to human serum albumin as well as to albumin from the frequent preclinical model species rat, cynomolgus monkey, mouse and dog. The relative affinities for the different species can be ranked as RSA≥HSA/CSA>MSA/DSA, i.e. the $K_D$ values ranked as $K_{D\text{-}RSA} \leq K_{D\text{-}HSA}/K_{D\text{-}CSA} < K_{D\text{-}MSA}/K_{D\text{-}DSA}$. The affinities in terms of $K_D$ values are the same or slightly lower (but in the same order of magnitude) as the affinity obtained for PEP06923 (non-inventive polypeptide).

Example 8

In Vitro Activity of Protein Z Variants Fused to an Albumin Binding Polypeptide

In this example, polypeptides comprising cytokine-specific protein Z (derivative of domain B of staphylococcal protein A) variants genetically fused to the albumin binding polypeptide variant PP013 (SEQ ID NO:13) were tested for their functionality, this being to block cytokine-induced proliferation of TF-1 cells in the presence of human serum albumin. Proliferation of TF-1 cells is dependent of the presence of any of several different types of cytokines and the proliferative response can be inhibited by blocking reagents such as the corresponding cytokine-specific protein Z variant. PP013 fused to a protein Z variant with specificity for an irrelevant protein was used as negative control.

Materials and Methods
Cloning of Z-PP013 Fusion Proteins

Gene fragments of protein Z variants with specificity for cytokine X or Y respectively, or for an irrelevant protein (negative control), were amplified by PCR using primers adding PstI and AccI specific endonuclease sites. The fragments were cleaved with PstI and AccI, purified and ligated into an expression vector, the plasmid pAY02747, restricted with the same enzymes. pAY02747 contains an origin of replication from pBR322, a kanamycin resistance gene and a T7 promoter for expression of the gene of interest. The cloning site is preceded by a sequence encoding the amino acids MGSSLQ and succeeded by a sequence encoding VDSS-PP013, where PP013 is the disclosed albumin binding polypeptide with SEQ ID NO:13. Ligation, transformation and sequence verification were performed as described above. The encoded proteins were:

1) MGSSLQ-$Z_X$-VDSS-PP013 (denoted $Z_X$-PP013) (SEQ ID NO:210)
2) MGSSLQ-$Z_Y$-VDSS-PP013 (denoted $Z_Y$-PP013) (SEQ ID NO:211)
3) MGSSLQ-$Z_{neg}$-VDSS-PP013 (denoted $Z_{neg}$-PP013) (SEQ ID NO:212)

Protein Expression $Z_X$-PP013, $Z_Y$—PP013 and $Z_{neg}$-PP013 were expressed in E. coli BL21 (DE3) cells. Colonies from the transformations of each fusion variant were used to inoculate starter cultures of 50 ml TSB+YE medium supplemented with kanamycin to a concentration of 50 µg/ml. The cultures were grown at 37° C. over night with agitation, 100 rpm. The starter cultures were then used to inoculate 900 ml TSB+YE medium supplemented with kanamycin to a concentration of 50 µg/ml. The cultures were grown for approximately 1.5 h to an OD600 of >1.1, upon which IPTG was added to a final concentration of 0.2 mM. Cultivation was continued for five hours. Cell pellets were harvested by centrifugation (15600 g, 4° C., 20 minutes) and stored at −20° C. until purification.

Protein Purification

Frozen cell pellets harboring soluble fusion protein variants $Z_X$-PP013, $Z_Y$—PP013 and $Z_{neg}$-PP013 were resuspended in 50 mM Tris-HCl, 150 mM NaCl, pH 8 and 1000 U BENZONASE (Merck Cat. No. 1.01654.0001) was added. The cells were disrupted by ultrasonication and for each of the fusion protein variants, the ultrasonicated suspension was clarified by centrifugation (15 min, 37000 g, 4° C.). 20×TST-buffer (20×[25 mM Tris-HCl, 1 mM EDTA, 200 mM NaCl, 0.05% Tween 20, pH 8.0]) was added at a volume resulting in 1×TST buffer in the clarified suspension. Each sample of fusion protein variant was loaded onto a HSA-Sepharose column (GE Healthcare). After washing with TST-buffer, followed by 5 mM NH$_4$Ac, pH 5.5, bound fusion protein variant was eluted with 0.5 M HAc, pH 2.5.

The fusion protein variants were further purified by reversed phase chromatography (RPC), as follows. For each of the variants, the eluate from the HSA-affinity purification step was loaded on a 1 ml Resource 15 RPC column (GE Healthcare) previously equilibrated with RPC A Buffer (0.1% TFA in water). After column wash with 10 CV RPC A Buffer and 5 CV of RPC B Buffer (0.1% TFA in acetonitrile), bound fusion proteins were eluted with a linear gradient of 10-50% RPC B Buffer over 20 CV. The flow rate was 2 ml/min and the absorbance at 280 nm was monitored. Fractions containing pure fusion protein variants were identified by SDS-PAGE analysis and pooled. Finally, the buffer was exchanged to 1×PBS (2.68 mM KCl, 137 mM NaCl, 1.47 mM KH$_2$PO$_4$, 8.1 mM Na$_2$HPO$_4$, pH 7.4) using a disposable PD-10 desalting column (GE Healthcare). To verify the identity of the fusion protein variants, SDS-PAGE and LC/MS analyses were performed as described in Example 1.

In Vitro Cell Assay of Z-PP013 Fusion Proteins

The cell line TF-1 (CLS Cat. No. 300434) was propagated as recommended by the provider in RPMI 1640 medium+10% fetal calf serum (Gibco) with the addition of 2 ng/ml of rhGM-CSF (Miltenyi). At the day of experiment, the cells were washed in RPMI 1640 medium+10% fetal calf serum to remove GM-CSF.

The ability of $Z_X$-PP013 and $Z_Y$—PP013 to block cytokine induced proliferation was analyzed by mixing the molecules $Z_X$-PP013, $Z_Y$-PP013 and $Z_{neg}$-PP013 with cytokines X and Y respectively, and with a five times molar excess of HSA (ALBUCULT, Novozymes). The molecules were titrated in a 2-fold dilution series with a fixed concentration of cytokine (4.9 µM) and a five times molar excess of HSA. The titration was performed in 96-well plates in a volume of 100 µl. 25 000 cells were added per well (100 µl) and plates were incubated at 37° C., 5% CO$_2$ for three days. To measure the proliferation, 19 µl of CCK-8 cell proliferation reagent (Sigma) diluted two times in RPMI 1640 medium+10% fetal calf serum, was added per well. The color reaction was monitored after 4 hours using 96-well plate reader (Victor3; PerkinElmer).

Results

As shown in FIG. 8, both $Z_X$-PP013 and $Z_Y$—PP013 inhibited the respective cytokine induced proliferation in the presence of HSA whereas $Z_{neg}$-PP013, the negative control, did not affect proliferation of TF-1. Thus, the experiment shows that the function of the Z molecules was retained when incorporated into a fusion protein containing the albumin binding polypeptide, and also when the fusion proteins were bound to albumin.

Example 9

Long-Term Stability of an Albumin Binding Polypeptide

In this example, the stability of PEP07986 (SEQ ID NO:163), expressed and purified as described in Example 1, was investigated after storage at 4, 25, and 40° C. for up to three months. The status of the polypeptide after storage was investigated by measuring its binding to HSA using a Biacore instrument.
Material and Methods Lyophilized PEP07986 was dissolved in sterile NaPi buffer (20 mM sodium phosphate, 150 mM sodium chloride, pH 7.2) at a concentration of 2 mg/ml. A reference sample (time=0) was removed and stored at −80° C. Aliquots of 105 µl were stored in sterile screw-cap eppendorf tubes sealed with parafilm at 4, 25, and 40° C. After one week, two weeks, one month and three months, a sample stored at each temperature was cooled to 4° C., centrifuged for 5 min at 13000 rpm and then stored at −80° C. awaiting Biosensor analysis.

Biosensor analysis was performed essentially as described in Example 2 but with HSA (ALBUCULT, Novozymes), immobilized to 704 resonance units (RU) and the albumin binding polypeptide variant was diluted to 10 nM and injected at a constant flow-rate of 20 µl/min for 10 minutes, followed by injection of HBS-EP for 10 minutes.
Results The binding to HSA of PEP07986 (SEQ ID NO:163) was retained after storage at 4, 25, and 40° C. for at least three months. The maximum binding responses to HSA obtained for PEP07986 stored at the various conditions are shown in FIG. 9.

Example 10

Stability of an Albumin Binding Polypeptide Under Extreme Conditions

In this example, biosensor and circular dichroism (CD) analysis of the albumin binding polypeptide PEP08296 (DOTA-conjugated PEP08185, SEQ ID NO:148) after heat treatment (90° C.) in low pH (~40) buffer is described. Since such extreme reaction conditions have to be used for example for $^{68}$Ga labeling of DOTA-modified proteins, the influence of high heat and low pH treatment on the structural identity of the polypeptide and its capacity to bind HSA was investigated by measuring the melting temperature (Tm), refolding properties and binding to HSA.
Material and Methods
Biosensor Analysis of Heat Stability Biosensor analysis on a Biacore 2000 instrument (GE Healthcare) was performed with HSA (ALBUCULT, Novozymes) immobilized by amine coupling onto the carboxylated dextran layer of the surfaces of CM-5 chip (research grade; GE Healthcare) according to the manufacturer's recommendations. Surface 1 of the chip was activated and deactivated and used as a reference cell (blank surface) during injections, whereas surface 2 comprised HSA immobilized to 724 resonance units (RU). PEP08296 (50 µl, 100 µg) in a 15 ml Falcon tube was diluted with 450 µl 0.2 M sodium acetate (NaAc) pH 5.5 to a final peptide concentration of 0.2 mg/mL. After addition of 1.5 ml 0.05 M HCl (resembling the conditions and volume used for eluting a $^{68}$Ge/$^{68}$Ga generator) the sample was incubated for 10 minutes at 90° C. or RT (control) and then transferred to RT. 6 ml 0.1 M sodium citrate was added to neutralize the pH. The heat treated PEP08296 (0.8 and 4 nM) was injected at a constant flow-rate of 50 µl/min for 5 minutes, followed by dissociation in HBS-EP for 15 minutes. The surfaces were regenerated with one injection of 25 µl 10 mM HCl. The results were analyzed with BIAevaluation software (GE Healthcare). Curves of the blank surface were subtracted from the curves of the ligand surfaces.
Determination of the Melting Temperature (Tm)

PEP08296 was dissolved in PBS to a final concentration of 0.5 mg/ml. PBS with a pH of approximately 4.0 was prepared by adding 9.5 µl 100 mM HCl to 100 µl PBS. Circular dichroism (CD) analysis was performed as described in Example 3.
CD Analysis of Heat Stability To investigate structural reversibility of PEP08296 after heat treatment, two CD spectra between 195 and 250 were recorded per sample at 20° C. After the first spectrum, a VTM cycle with heating to 90° C. was run as described above followed by collection of the second CD spectrum between 195 and 250 nm at 20° C. In addition, PEP08296 was incubated in PBS pH 4.0 buffer or PBS pH 7.2 buffer for 12 minutes at 90° C. in a thermomixer (500 rpm, interval mixing 10 s on, 30 s off). After incubation, the samples were cooled on ice followed by centrifugation at 13000 rpm for 1 minute, and a CD spectrum between 195 and 250 nm was recorded at 20° C.
Results Biosensor analysis was used to investigate if heat treatment in combination with low pH, i.e. common conditions needed for $^{68}$Ga-labeling of polypeptide, would affect the capacity of PEP08296 to bind to HSA. FIG. 10 shows the result of this binding analysis performed with a Biacore 2000 instrument. Two different concentrations of PEP08296, 0.8 nM and 4 nM, were injected over a surface with 724 RU of immobilized human serum albumin. Heat treatment for 10 min at 90° C., pH 4.0, slightly reduced the binding capacity of PEP08296 to HSA, indicating a potential structural change of the molecule.

CD was used to further investigate the potential structural change of the molecule. Similar CD spectra before and after heating would prove a sample to be structurally reversible. In the first experiment, the samples were heated with a temperature gradient from 20° C. to 90° C. The CD spectra before and after heat treatment were similar in the Tm determination experiment with the typical minima at 207 and 221 nm indicating α-helicity, i.e. short time heating to 90° C. in either pH 4 or pH 7.2 buffer had no effect on the structure of PEP08296.

However, pretreatment of PEP08296 for 12 minutes at 90° C. showed a slightly reduced alpha helix content of PEP08296 if incubated at pH 4.0, but no change in alpha helix content if incubated at pH 7.2. Typical overlays of two CD spectra before and after heating are shown in FIG. 11.

The results from the melting temperature (Tm) determination are summarized in Table 4.

TABLE 4

Tm of PEP08296

| Designation | Tm (° C.) |
|---|---|
| PEP08296 at pH 7.2 | 59 |
| PEP08296 at pH 4.0 | 62 |

Example 11

Blood Pool Imaging Using a $^{68}$Ga-Labeled Albumin Binding Polypeptide

In the experiments making up this example, whole body distribution of $^{68}$Ga-labeled PEP08296 (DOTA-conjugated PEP08185, SEQ ID NO:148) in rats was followed by dynamic imaging over 1.5 hours. Due to the strong association between the labeled polypeptide and serum albumin, the labeled polypeptide can be used for example to study blood pool and tissue permeability.

Material and Methods $^{68}$Ga-Labeling of PEP08296

$^{68}$Ga was eluted as $^{68}$GaCl$_3$ from the $^{68}$Ge/$^{68}$Ga generator (Obninsk, Russia) with 0.1 M HCl, converted to $^{68}$GaCl$_4$— with concentrated HCl, trapped on an anionic exchange column (Chromafix-HCO$_3$) and subsequently eluted with 18 MO water, as previously described (Velikyan et al (2008), Nucl Med Biol 35:529-536).

The labeling was performed essentially as described in Tolmachev et al. (EJNMMI 37:1356-1367, 2010). The concentrated $^{68}$Ga-eluate (150-200 µl) was added to PEP08296 (100 µg in 0.2 M sodium acetate buffer pH 5.5) and the pH was adjusted to 3.5-4 using sodium acetate (1.25 M) or HCl (0.1 M). The labeling mixture was incubated at 90° C. for 15 min before cooling, and the labeled protein was isolated by size exclusion purification on a NAP-5 column eluted with physiologically buffered saline.

The radiochemical purity and identity of the $^{68}$Ga-labeled protein was assessed by radio-HPLC using UV (210 nm) and radioactivity detectors in series and a Superdex Peptide 10/300 GL column (GE Healthcare) eluted with physiologically buffered saline.

Small Animal PET

A rat (277 g) was anesthetized with isoflurane (initially 5%, then 2% blended with 7:3 air/O$_2$), controlled by an E-Z vaporizer using Microflex non-rebreather masks from Euthanex Corporation, and was kept on a heating pad (37° C.) while lying within a microPET Focus120 system (Siemens, CTI Concorde Microsystems). $^{68}$Ga-PEP08296, 33 MBq, was dispensed in a syringe, diluted with saline to 0.5 ml and injected via the tail vein. Data were acquired from the whole body by moving the bed in a constant bed motion protocol for 1.5 h. Data were processed with MicroPET Manager and corrected for randoms, dead time and decay. Images were reconstructed by standard 2D filtered back projection using a ramp filter and evaluated using Inveon Research Workplace (Siemens Medical Solutions) software.

Results

Basic distribution patterns (FIG. 12) for PEP08296 were very similar to that of albumin labeled with radioisotopes such as $^{68}$Ga-DOTA, $^{64}$Cu-DOTA and $^{11}$C (see e.g. Hoffend et al (2005), Nucl Med Biol 32:287-292 and Lu et al (2008), "[1-$^{11}$C]Butanol and [Methyl-$^{11}$C]Albumin for Blood Flow and Blood Pool Imaging", poster at the XIth Turku PET Symposium, 24-27 May 2008). In brief, high radioactivity concentrations were observed in major blood vessels throughout the scan. Organs with large blood volumes (liver, spleen and kidney) were also clearly delineated, as was the cardiac blood pool radioactivity. Radioactivity in the urinary bladder increased during the observation period, this observation of renal elimination being consistent with previous observations with labeled albumin-based tracers and with that of the metabolism of albumin itself.

The general distribution pattern of radioactivity and very slow plasma clearance after intravenous injection of $^{68}$Ga-PEP08296 is consistent with its expected very rapid and strong binding to albumin. These results therefore support further applications of the radiotracer as an in vivo blood pool imaging agent for use with positron emission tomography studies of tissue permeability, both during the development of disease and during therapeutic intervention.

Example 12

Solubility of an Albumin Binding Polypeptide

The solubility of PEP07986 (SEQ ID NO:163) in physiological buffer was investigated by consecutive concentrations of the sample using ultrafiltration, followed by concentration measurement and investigation of aggregation status. Concentrations determined by direct absorbance readings at 280 nm were consistent with concentrations determined by gel filtration, showing a solubility of more than 42 mg/ml with no aggregates detected.

Material and Methods

Lyophilized PEP07986 was dissolved in NaPi buffer (20 mM sodium phosphate, 150 mM sodium chloride, pH 7.2) at a concentration of 3 mg/ml. Amicon Ultra centrifugal filter units, cut off of 3 kDa, (Millipore, Cat. No. UFC800324) were prerinsed with 2 ml NaPi buffer by centrifugation at 4000 g for 20 min in a swinging bucket rotor centrifuge (Multifuge, Heraeus). 1620 µl of 3 mg/ml PEP07986 was applied to a first centrifugal filter unit and centrifugation was performed at 4000 g, 20° C., for 7 min. A 25 µl sample was removed (UF sample 1) for further analysis and the rest of the sample was transferred to a second centrifugal filter unit. The centrifugation and sample removal were repeated three times with spinning times of 8, 9 and 20 min respectively (UF sample 2, 3 and 4 respectively). Absorbance readings were performed using a NANODROP ND-1000 Spectrophotometer and by diluting UF samples 1-4 in NaPi buffer 2, 4, 6 and 12 times respectively. The concentrations were calculated using the extinction coefficient 1 Abs 280=1.955 mg/ml. Gel filtration was performed on a 1100 HPLC system (Agilent Technologies) using a Superdex75 10/300 GL column (GE Healthcare) which had been equilibrated in NaPi buffer. 10 µl of each UF sample were applied to the column; NaPi buffer was used as running buffer and the flow rate was 0.5 ml/min. A chromatogram of the molecular weight standard ovalbumin (GE Healthcare), injected at a concentration of 5 mg/ml was collected as well. Concentrations were determined by integrating the area under the curve.

Results

Concentrations determined by direct absorbance readings at 280 nm and concentrations determined by gel filtration are shown in Table 5. The solubility of PEP07986 (SEQ ID NO:163) is at least 42 mg/ml in physiological buffer (20 mM sodium phosphate, 150 mM sodium chloride, pH 7.2). No aggregates were detected by gel filtration, as shown by FIG. 13.

TABLE 5

Concentrations determined after consecutive concentration of PEP07986 (SEQ ID NO: 163)

| Sample | Concentrations (mg/ml) determined by | |
|---|---|---|
| | Spectrophotometer | Gel filtration |
| UF2 | 12.1 | 12.4 |
| UF3 | 22.2 | 22.1 |
| UF4 | 42.7 | 42.6 |

The invention claimed is:

1. An albumin binding polypeptide comprising the amino acid sequence selected from:

i)
(SEQ ID NO: 204)
LAX$_3$AKX$_6$X$_7$ANX$_{10}$ ELDX$_{14}$YGVSDF YKRLIX$_{26}$
KAKTVEGVEALKX$_{39}$X$_{40}$ILX$_{43}$X$_{44}$LP wherein independently of each other
X$_3$ is selected from E, S and Q;
X$_6$ is selected from E and S;
X$_7$ is selected from A and S;
X$_{10}$ is selected from A, S and R;
X$_{14}$ is selected from A, S, C and K;
X$_{26}$ is selected from D and E;
X$_{39}$ is selected from D and E;
X$_{40}$ is selected from A and E;
X$_{43}$ is selected from A and K;
X$_{44}$ is selected from A, S and E;
L in position 45 is present or absent; and
P in position 46 is present or absent; and
ii) an amino acid sequence which has at least 95% identity to the full-length sequence defined in i) with the proviso that X$_7$ is neither L, E nor D;
wherein the albumin binding polypeptide does not comprise a hormone polypeptide.

2. The albumin binding polypeptide according to claim 1, wherein X$_6$ is E.

3. The albumin binding polypeptide according to claim 1, wherein X$_3$ is S.

4. The albumin binding polypeptide according to claim 1, wherein X$_3$ is E.

5. The albumin binding polypeptide according to claim 1, wherein X$_7$ is A.

6. The albumin binding polypeptide according to claim 1, wherein X$_{14}$ is S.

7. The albumin binding polypeptide according to claim 1, wherein X$_{14}$ is C.

8. The albumin binding polypeptide according to claim 1, wherein X$_{10}$ is A.

9. The albumin binding polypeptide according to claim 1, wherein X$_{10}$ is S.

10. The albumin binding polypeptide according to claim 1, wherein X$_{26}$ is D.

11. The albumin binding polypeptide according to claim 1, wherein X$_{26}$ is E.

12. The albumin binding polypeptide according claim 1, wherein X$_{39}$ is D.

13. The albumin binding polypeptide according to claim 1, wherein X$_{39}$ is E.

14. The albumin binding polypeptide according to claim 1, wherein X$_{40}$ is A.

15. The albumin binding polypeptide according to claim 1, wherein X$_{43}$ is A.

16. The albumin binding polypeptide according to claim 1, wherein X$_{44}$ is A.

17. The albumin binding polypeptide according to claim 1, wherein X$_{44}$ is S.

18. The albumin binding polypeptide according to claim 1, wherein L in position 45 is present.

19. The albumin binding polypeptide according to claim 1, wherein P in position 46 is present.

20. The albumin binding polypeptide according to claim 1, which binds to albumin such that the k$_{off}$ value of the interaction is at most $5 \times 10^{-5}$ s$^{-1}$.

21. The albumin binding polypeptide according to claim 20, which binds to albumin such that the k$_{off}$ value of the interaction is at most $5 \times 10^{-6}$ s$^{-1}$.

22. The albumin binding polypeptide according to claim 1, whose wherein the amino acid sequence is selected from the group consisting of SEQ ID NO:1-144 and SEQ ID NO:164-203.

23. The albumin binding polypeptide according to claim 22, wherein the amino acid sequence is selected from the group consisting of SEQ ID NO:4-5, SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:41-42, SEQ ID NO:49-50, SEQ ID NO:164-170 and SEQ ID NO:192-203.

24. The albumin binding polypeptide according to claim 22, wherein the amino acid sequence is selected from the group consisting of SEQ ID NO:1-144.

25. The albumin binding polypeptide according to claim 24, wherein the amino acid sequence is selected from the group consisting of SEQ ID NO:4-5, SEQ ID NO:7-8, SEQ ID NO:10-11, SEQ ID NO:13-14, SEQ ID NO:16-17, SEQ ID NO:19-20, SEQ ID NO:22-23, SEQ ID NO:25-26, SEQ ID NO:28-29, SEQ ID NO:31-32, SEQ ID NO:34-35, SEQ ID NO:37-38, SEQ ID NO:41-42 and SEQ ID NO:49-50.

26. The albumin binding polypeptide according to claim 1, further comprising one or more additional amino acid residues positioned at the N- and/or the C-terminal of the sequence defined in i).

27. The albumin binding polypeptide according to claim 26, in which the additional amino acids comprise at least one serine residue at the N-terminal of the polypeptide.

28. The albumin binding polypeptide according to claim 26, in which the additional amino acids comprise a glycine residue at the N-terminal of the polypeptide.

29. The albumin binding polypeptide according to claim 26, in which the additional amino acids comprise a cysteine residue at the N-terminal of the polypeptide.

30. The albumin binding polypeptide according to claim 26, in which the additional amino acids comprise a lysine residue at the C-terminal of the polypeptide.

31. The albumin binding polypeptide according to claim 26, in which the additional amino acids comprise a glycine residue at the C-terminal of the polypeptide.

32. The albumin binding polypeptide according to claim 26, in which the additional amino acids comprise a cysteine residue at the C-terminal of the polypeptide.

33. The albumin binding polypeptide according to claim 26, wherein the amino acid sequence is selected from any one of SEQ ID NO: 145-150 and SEQ ID NO:162-163.

34. The albumin binding polypeptide according to claim 1, comprising no more than two cysteine residues.

35. The albumin binding polypeptide according to claim 34, comprising no more than one cysteine residue.

36. The albumin binding polypeptide according to claim 1, which binds to human serum albumin.

37. A fusion protein or conjugate comprising
    i) a first moiety consisting of the albumin binding polypeptide according to claim 1; and
    ii) a second moiety consisting of a polypeptide having a desired biological activity, wherein the fusion protein or conjugate does not comprise a hormone polypeptide.

38. The fusion protein or conjugate according to claim 37, in which the second moiety having a desired biological activity is a therapeutically active polypeptide.

39. The fusion protein or conjugate according to claim 38, in which the second moiety having a desired biological activity is selected from the group consisting of human endogenous enzymes, growth factors, chemokines, cytokines and lymphokines.

40. The fusion protein or conjugate according to claim 39, in which the second moiety is selected from the group consisting of interleukin-2 (IL-2), interleukin-1 receptor antagonist (IL-1RA), keratinocyte growth factor (KGF), ancestim, cytotoxic T lymphocyte-associated protein 4 (CTLA-4), Factor VII, Factor VIII and Factor IX.

41. The fusion protein or conjugate according to claim 38, in which the second moiety having a desired biological activity is a non-human biologically active protein selected from the group consisting of bacterial toxins, enzymes and activating proteins.

42. The fusion protein or conjugate according to claim 37, in which the second moiety having a desired biological activity is a binding polypeptide capable of selective interaction with a target molecule.

43. The fusion protein or conjugate according to claim 42, in which the binding polypeptide is selected from the group consisting of antibodies and fragments and domains thereof retaining antibody binding activity; microbodies, maxybodies, avimers, other small disulfide-bonded proteins; binding proteins derived from a scaffold selected from the group consisting of staphylococcal protein A and domains thereof, domain GM of protein G from Streptococcus strain G148, lipocalins, ankyrin repeat domains, cellulose binding domains, γ crystallines, green fluorescent protein, human cytotoxic T lymphocyte-associated antigen 4, protease inhibitors, Kunitz domains, PDZ domains, SH3 domains, peptide aptamers, staphylococcal nuclease, tendamistats, fibronectin type III domain, transferrin, zinc fingers and conotoxins.

44. The fusion protein or conjugate according to claim 43, in which said target molecule is selected from the group consisting of amyloid β (Aβ) peptide; toxins, bacterial toxins, snake venoms; blood clotting factors, von Willebrand factor; interleukins, interleukin-13 (IL-13); myostatin; pro-inflammatory factors, tumor necrosis factor alpha (TNF-α), TNF-α receptor, IL-1, IL-23, IL-8; complement factors, complement component 3 (C3), C5; hypersensitivity mediators, histamine, immunoglobulin E (IgE); tumor antigens, cluster of differentiation molecule 19 (CD19), CD20, CD22, CD30, CD33, CD40, CD52, CD70, oncogene MET (cMet), epidermal growth factor receptor 1 (HER1), HER2, HER3, HER4, carbonic anhydrase IX (CAIX), carcinoembryonic antigen (CEA), IL-2 receptor, mucin 1 (MUC1), prostate-specific membrane antigen (PSMA), tumor-associated glycoprotein 72 (TAG-72), granulocyte-colony stimulating factor (G-CSF), granulocyte-macrophage colony-stimulating factor (GM-CSF), growth hormone (GH), insulin, and somatostatin.

45. The fusion protein or conjugate according to claim 37, comprising a further moiety consisting of a polypeptide having a further, desired biological activity, which may be the same as or different from that of the second moiety.

46. The fusion protein or conjugate according to claim 45, wherein the second moiety is a therapeutically active polypeptide, and the further moiety is a binding polypeptide capable of selective interaction with a target molecule.

47. The fusion protein or conjugate according to claim 37, in which the second moiety is conjugated to the albumin binding polypeptide via the thiol group of any cysteine residue present at position $X_{14}$ of the polypeptide.

48. The albumin binding polypeptide, according to claim 1, further comprising a cytotoxic agent.

49. The albumin binding polypeptide according to claim 48, wherein the cytotoxic agent is selected from calicheamycin, auristatin, doxorubicin, maytansinoid, taxol, ecteinascidin, geldanamycin, methotrexate and their derivatives, and combinations thereof.

50. The albumin binding polypeptide, according to claim 1 further comprising a label.

51. The albumin binding polypeptide, according to claim 50, in which said label is selected from the group consisting of fluorescent dyes and metals, chromophoric dyes, chemiluminescent compounds and bioluminescent proteins, enzymes, radionuclides and particles.

52. The albumin binding polypeptide, according to claim 51, comprising a chelating environment provided by a polyaminopolycarboxylate chelator conjugated to the albumin binding polypeptide via a thiol group of a cysteine residue or an amine group of a lysine residue.

53. The albumin binding polypeptide, according to claim 52, wherein the polyaminopolycarboxylate chelator is 1,4,7,10-tetraazacyclododecane-1,4,7,10-tetraacetic acid or 1,4,7,10-tetraazacyclododecane-1,4,7-tris-acetic acid-10-maleimidoethylacetamide.

54. The albumin binding polypeptide, according to claim 52, wherein the polyaminopolycarboxylate chelator is diethylenetriaminepentaacetic acid.

55. A polynucleotide encoding the albumin binding polypeptide according to claim 1.

56. A method of producing a polypeptide, comprising expressing the polynucleotide according to claim 55.

57. An expression vector comprising the polynucleotide according to claim 55.

58. A host cell comprising the expression vector according to claim 57.

59. A method of producing the albumin binding polypeptide according to claim 1 by non-biological peptide synthesis using amino acids and/or amino acid derivatives having protected reactive side-chains, the non-biological peptide synthesis comprising
  step-wise coupling of the amino acids and/or the amino acid derivatives to form the albumin binding polypeptide, deprotecting the protected reactive sidechains of the albumin binding polypeptide, and folding of the albumin binding polypeptide in aqueous solution.

60. The method of producing a polypeptide according to claim 59, further comprising conjugating the albumin binding polypeptide with a therapeutically active polypeptide.

* * * * *

UNITED STATES PATENT AND TRADEMARK OFFICE
CERTIFICATE OF CORRECTION

PATENT NO. : 10,329,331 B2
APPLICATION NO. : 14/955647
DATED : June 25, 2019
INVENTOR(S) : Caroline Ekblad and Lars Abrahmsen Page 1 of 1

It is certified that error appears in the above-identified patent and that said Letters Patent is hereby corrected as shown below:

On the Title Page

Please replace item (63) with the following --Continuation of application No. 13/808,713 filed on Aug. 20, 2013, now Pat. No. 9,211,344 filed as PCT application No. PCT/EP/2011/061623 on Jul. 8, 2011--

In the Claims

Column 142, Line 50, (approx.), Claim 22, please replace "claim 1, whose wherein the amino" with --claim 1, wherein the amino--

Column 144, Line 4, (approx.), Claim 43, please replace "domain GM of protein G" with --domain GA3 of protein G--

Signed and Sealed this
Twenty-ninth Day of October, 2019

Andrei Iancu
*Director of the United States Patent and Trademark Office*